US00RE41408E

(19) United States
(12) Reissued Patent
Reder et al.

(10) Patent Number: US RE41,408 E
(45) **Date of Reissued Patent: *Jun. 29, 2010**

(54) METHOD OF PROVIDING SUSTAINED ANALGESIA WITH BUPRENORPINE

(75) Inventors: Robert F. Reder, Greenwich, CT (US); Robert F. Kaiko, Weston, CT (US); Paul D. Goldenheim, Wilson, CT (US)

(73) Assignee: Purdue Pharma L.P., Stamford, CT (US)

( * ) Notice: This patent is subject to a terminal disclaimer.

(21) Appl. No.: 11/799,608

(22) Filed: May 1, 2007

Related U.S. Patent Documents

Reissue of:
(64) Patent No.: 6,231,886
Issued: May 15, 2001
Appl. No.: 09/311,997
Filed: May 14, 1999

U.S. Applications:

(63) Continuation of application No. 11/033,107, filed on Jan. 11, 2005, now abandoned, which is a continuation of application No. 08/939,068, filed on Sep. 29, 1997, now Pat. No. 5,968,547.
(60) Provisional application No. 60/038,919, filed on Feb. 24, 1997.

(51) Int. Cl.
*A61F 13/00* (2006.01)
*A61K 9/70* (2006.01)

(52) U.S. Cl. ..... 424/449; 424/443; 424/446; 424/447

(58) Field of Classification Search ..... 424/449, 424/443, 446, 447, 489
See application file for complete search history.

(56) References Cited

U.S. PATENT DOCUMENTS

| | | | | |
|---|---|---|---|---|
| 3,996,934 | A | | 12/1976 | Zaffaroni |
| 4,058,599 | A | | 11/1977 | Bauer et al. |
| 4,060,084 | A | | 11/1977 | Chandrasekaran et al. |
| 4,119,713 | A | | 10/1978 | Carosio |
| 4,262,003 | A | | 4/1981 | Urquhart et al. |
| 4,379,454 | A | | 4/1983 | Campbell et al. |
| 4,582,835 | A | | 4/1986 | Lewis et al. |
| 4,588,580 | A | | 5/1986 | Gale et al. |
| 4,673,679 | A | | 6/1987 | Aungst et al. |
| 4,784,855 | A | | 11/1988 | Yamashita et al. |
| 4,806,341 | A | | 2/1989 | Chien et al. |
| 4,879,297 | A | | 11/1989 | Mahjour et al. |
| 4,906,463 | A | | 3/1990 | Cleary et al. |
| 4,908,027 | A | | 3/1990 | Enscore et al. |
| 4,938,759 | A | | 7/1990 | Enscore et al. |
| 4,945,103 | A | | 7/1990 | Cohen |
| 4,956,171 | A | | 9/1990 | Chang |
| 4,983,395 | A | | 1/1991 | Chang et al. |
| 4,994,278 | A | | 2/1991 | Sablotsky et al. |
| 5,026,556 | A | | 6/1991 | Drust et al. |
| 5,028,435 | A | | 7/1991 | Katz et al. |
| 5,069,909 | A | | 12/1991 | Sharma et al. |
| 5,075,341 | A | | 12/1991 | Mendelson et al. |
| 5,090,405 | A | | 2/1992 | Jansen et al. |
| 5,091,186 | A | | 2/1992 | Miranda et al. |
| 5,132,115 | A | | 7/1992 | Wolter |
| 5,149,538 | A | * | 9/1992 | Granger et al. ..... 424/449 |
| 5,176,916 | A | | 1/1993 | Yamanaka et al. |
| 5,225,199 | A | | 7/1993 | Hidaka et al. |
| 5,225,440 | A | * | 7/1993 | London et al. ..... 514/535 |
| 5,236,714 | A | | 8/1993 | Lee et al. |
| 5,238,933 | A | | 8/1993 | Catz et al. |
| 5,240,711 | A | | 8/1993 | Hille et al. |
| 5,272,149 | A | | 12/1993 | Stalling |
| 5,306,503 | A | | 4/1994 | Muller et al. |
| 5,336,210 | A | | 8/1994 | Hidaka et al. |
| 5,342,623 | A | | 8/1994 | Enscore et al. |
| 5,344,656 | A | | 9/1994 | Enscore et al. |
| 5,352,457 | A | | 10/1994 | Jenkins |
| 5,462,745 | A | | 10/1995 | Enscore et al. |
| 5,486,362 | A | | 1/1996 | Kitchell et al. |
| 5,580,876 | A | * | 12/1996 | Crain et al. ..... 514/282 |
| 5,613,958 | A | | 3/1997 | Kochinke et al. |
| 5,635,203 | A | | 6/1997 | Gale et al. |
| 5,683,711 | A | | 11/1997 | Fischer et al. |
| 5,700,480 | A | | 12/1997 | Hille et al. |
| 5,732,717 | A | | 3/1998 | Watanabe et al. |
| 5,785,991 | A | | 7/1998 | Burkoth et al. |
| 5,814,032 | A | | 9/1998 | Hori et al. |
| 5,817,665 | A | | 10/1998 | Dante et al. |
| 5,830,505 | A | | 11/1998 | Fischer et al. |
| 5,834,010 | A | | 11/1998 | Quan et al. |
| 5,837,289 | A | | 11/1998 | Grasela et al. |

(Continued)

FOREIGN PATENT DOCUMENTS

| | | | |
|---|---|---|---|
| DE | 3526339 | | 1/1992 |
| DE | 3546830 | | 7/1995 |
| DE | 19840758 | A1 * | 3/2000 |
| EP | 0368409 | | 5/1990 |
| EP | 430019 | * | 6/1991 |
| EP | 432945 | * | 6/1991 |
| EP | 819438 | * | 1/1998 |
| EP | 821957 | * | 2/1998 |

(Continued)

OTHER PUBLICATIONS 7.2 Buprenorphine, MNH/PAD/87.11, pp. 29–63 (1987).
BTDS List of Studies (Mar. 30, 2000).

(Continued)

*Primary Examiner*—Blessing M Fubara
(74) *Attorney, Agent, or Firm*—Duane Morris LLP

(57) ABSTRACT

A method of effectively treating pain in humans is achieved by administering buprenorphine in accordance with first order kinetics over an initial three-day dosing interval, such that a maximum plasma concentration from about 20 pg/ml to about 1052 pg/ml is attained, and thereafter maintaining the administration of buprenorphine for at least an addition two-day dosing interval in accordance with substantially zero order kinetics, such that the patients experience analgesia throughout the at least two-day additional dosing interval.

18 Claims, 5 Drawing Sheets

U.S. PATENT DOCUMENTS

| | | | |
|---|---|---|---|
| 5,843,468 | A | 12/1998 | Burkoth et al. |
| 5,900,420 | A | 5/1999 | Cole |
| 5,919,473 | A | 7/1999 | Elkhoury |
| 5,942,530 | A | 8/1999 | Panetta |
| 5,968,547 | A | 10/1999 | Reder et al. |
| 5,989,585 | A | 11/1999 | Bracher |
| 6,004,969 | A | 12/1999 | Hu |
| 6,024,974 | A | 2/2000 | Li |
| 6,024,976 | A | 2/2000 | Miranda et al. |
| 6,096,756 | A | 8/2000 | Crain et al. |
| 6,165,499 | A | 12/2000 | Kleinsorgen et al. |
| 6,210,699 | B1 | 4/2001 | Acharya et al. |
| 6,231,886 | B1 | 5/2001 | Reder et al. |
| 6,242,456 | B1 | 6/2001 | Shuster et al. |
| 6,264,980 | B1 | 7/2001 | Hille |
| 6,280,766 | B1 | 8/2001 | Becher et al. |
| 6,344,212 | B2 | 2/2002 | Reder et al. |
| 6,391,294 | B1 | 5/2002 | Dettmar et al. |
| 6,436,977 | B1 | 8/2002 | Thompson |
| 6,554,851 | B1 | 4/2003 | Palasis et al. |
| 6,595,956 | B1 | 7/2003 | Gross et al. |
| 6,787,149 | B1 | 9/2004 | El Khoury et al. |
| 6,865,444 | B2 | 3/2005 | Howard |
| 7,011,843 | B2 | 3/2006 | Becher et al. |
| 7,056,527 | B2 | 6/2006 | Maruo et al. |
| 7,270,830 | B2 | 9/2007 | Reidenberg |
| 2001/0051186 | A1 | 12/2001 | Acharya et al. |
| 2002/0137761 | A1 | 9/2002 | Crain et al. |
| 2003/0104976 | A1 | 6/2003 | Davar et al. |
| 2003/0114475 | A1 | 6/2003 | Fox et al. |
| 2004/0146547 | A1 * | 7/2004 | Marcenyac et al. |
| 2004/0241218 | A1 * | 12/2004 | Tavares |

FOREIGN PATENT DOCUMENTS

| | | | |
|---|---|---|---|
| EP | 1422230 | * | 5/2004 |
| GB | 2165148 | | 5/1989 |
| PL | 166095 | * | 3/1995 |
| WO | 9619975 | | 12/1994 |
| WO | 95/01167 | | 1/1995 |
| WO | 95/20393 | | 8/1995 |
| WO | 96/19975 | | 7/1996 |
| WO | 1997-004835 | * | 2/1997 |
| WO | 97/48380 | | 12/1997 |
| WO | 1998-026780 | * | 6/1998 |
| WO | 98/36728 | | 8/1998 |
| WO | 1999-012529 | * | 3/1999 |
| WO | 1999-032120 | * | 7/1999 |
| WO | 2000-035456 | * | 6/2000 |
| WO | 2002-070524 | * | 9/2002 |
| WO | 2002-085268 | * | 10/2002 |
| WO | 2003-079945 | * | 10/2003 |
| WO | 2004-103317 | * | 12/2004 |
| WO | 2005-011579 | * | 2/2005 |

OTHER PUBLICATIONS

Buprenorphine prescription withdrawn in Norway, available at http://www.drugscope.org.uk (Sep. 21, 2001).

Buprenorphine TDS Pre–NDA Meeting. Flux rate analysis of Buprenorphine transdermal delivery systems (BTDS) (Jun. 9, 1999).

Lasseter et al., Systemic pharmacokinetic (PK) study of buprenorphine (B) in mild to moderate chronic hepatic impairment (CHI). Amer Soc for Clin Phamcol and Therapeut. PI–4. (Feb. 2001).

Rigas et al., "Transdermal fentanyl: Practical use in the hospital and the home" ASHP *Midyear Clinical Meeting* v. 27 (1992).

The Safety of High Doses of Buprenorphine. Tables of Contents and Introduction (Feb. 22, 2002).

Cymbalta® ((duloxetine hydrochloride) Delayed–release Capsules) *Physician's Desk Reference* 59$^{th}$ ed., 2005.

Opana® ER ((Oxymorphone Hydrochloride) Extended Release Tablets) *Physician's Desk Reference* 61$^{st}$ ed., 2007.

Cranmer K., Laudau CJ, Friedman My Turner NG, Ripa SR. The Safety and tolerability 0 of 7–day buprenorphine TDS in the analgesic management of pain in the elderly—a six–month evaluation. www.ASCP.com/education/postersandpapersam05.com. Poster 34. (Study BUP3002S) (Nov. 2005).

Definition of "Aldehyde," printed on Sep. 1, 2009 from Answers.com.

Definition of "Photoinitiator," printed on Sep. 1, 2009 from Answers.com.

Definition of "Polymerize," printed on Sep. 1, 2009 from Answers.com.

Definition of "Tannin," printed on Sep. 1, 2009 from Wikipedia.org, the free cncyclopedia..

Bauer, KH (ed.) *Pharmaceutische Technologie* pp. 362–365 (1993).

Budd, K., *Experience with partial agonists in the treatment of cancer pain* in: Doyle, D (ed.), *Opioids in the Treatment of Cancer Pain*, Royal Society of Medicine Services International Congress and Symposium Series No. 146 (1990).

Burke et al., "Increased rates of drug abuse and dependence after onset of mood or anxiety disorders in adolescence" *Hospital & Community Psychiatry* 45(5): 451–455 (1994) (Abstract only).

Curran et al., "Recognition and management of depression in a substance use disorder treatment population" *American Journal of Drug & Alcohol Abuse* 33(4): 563–569 (2007) (Abstract only).

Currie et al., "Comorbidity of major depression with substance use disorders" *Canadian Journal of Psychiatry* 50(10): 660–666 (2005).

Davis et al., "Major despression and comorbid substance use disorders" *Current Opinions in Psychiatry* 21(1): 14–18 (2008).

Declaration of Prof. Jonathan Hadgraft dated Apr. 22, 2009.

Declaration of Prof. Jonathan Hadgraft dated Jul. 9, 2004.

Declaration of Prof. Jonathan Hadgraft dated Oct. 8, 2004.

Declaration of Prof. Jonathan Hadgraft dated Oct. 11, 2007.

Driscoll, CE *Primary Care*14(2): 337–352 (1987).

Excerpt of Review for Approval issued Aug. 7, 1990 by the FDA for Duragesic®.

Grond, S et al. *Pain* 69: 191–198 (1997).

Heilman, N *Therapcutische Systeme*, 4$^{th}$ ed., Stuttgart: Enke pp. 67–77 and 83–86 (1984).

Heilman, N *Therapcutische Systeme*, 4$^{th}$ ed., Stuttgart: Enke pp. 104–106 (1984).

Introduction to the Pharmacology of Opioids (Apr. 23, 2009).

Jin–Jie, G. "Synthesis of biodegradable polyurethane foams from condensed tannin and bark of Acacia mearnsii" *Bull. Kyushu Univ. For.* 79: 21–85 (1998).

Landau, CJ et al., "Buprenorphine transdermal delivery system in adults with persistent noncancer–related pain syndromes who require opioid therapy: a multicenter, 5–week run–in and randomized, double–blind maintenance–of–analgesia study" *Clinical Therapeutics* 29(10): 2179–2193 (2007).

Markou et al., "Neurobiological similarities in depression and drug dependence: a self–medication hypothesis" *Neuropsychopharmagology* 18(3): 135–174 (1998).
Mongan, Mary Louise Hack *The Effects of Low Dose Buprenorphine on Selected Psychiatric Patients* San Francisco State University, San Francisco, CA. 1992, 105 ppg.
Nagle, CJ et al., *Current Anaesthesia and Care* 1: 247–252 (1990).
Office Actions dated Sep. 19, 2008 and Feb. 9, 2009, issued in the prosecution of U.S. Appl. No. 10/394,425 to Kaiko et al., filed Mar. 20, 2003.
Office Actions dated Dec. 15, 2008, Feb. 18, 2009 and Apr. 6, 2009, issued in the prosecution of U.S. Appl. No. 10/476,601 to Tavares et al., filed Nov. 20, 2003.
*Physician's Desk Reference* 49$^{th}$ ed., 1995, entry on Duragesic®.
*Physician's Desk Reference* 50$^{th}$ ed., 1996, entry on Duragesic®.
Product Monograph for Duragesic® (2008).
Regier et al., "Comorbility of mental disorders with alcohol and other drug abuse. Results from the Epidemiological Catchment Area (ECA) Study" JAMA 264(19): 2549–2550 (990) (Abstract only).
Roy, SD et al., *J. Pharmaceutical Sciences* 83: 1723–1728 (1994).
Sorrell, DC *Nursing* 24:30 (1994).
Southam, MA *Anti–Cancer Drugs* 6(suppl. 3): 29–34 (1995).
Steiner, D et al., "The efficacy and safety of buprenorphine transdermal system (BTDS) in subjects with moderate to severe low back pain" Presentation #305, PowerPoint Presentation at American Pain Society Annual Meeting, May 6–9, 2009, San Diego, CA.
Subramaniam et al., "Baseline depressive symptoms predict poor substance use outcome following adolescent residential treatment" *Journal of the American Academy of Child & Adolescent Psychiatry* 46(8): 1062–1069 (2007) (Abstract only).
Swendsen et al., "The comorbidity of depression and substance use disorders" *Clin. Psychol. Rev.* 20(2): 173–189 (2000) (Abstract only).
Wall, PD, et al., *Textbook of Pain* 2$^{nd}$ ed., New York: Churchill Livingstone, pp. 686–701 (1989).
Woodroffe, MA et al., *Canadian Family Physician* 43: 268–272 (1997).
Hexal AG Opposition against EP–B–964677, dated May 15, 2007. (in German, w/ Engl. translation).
Novosis AG Opposition against EP–B–964677, dated May 15, 2007. (in German, w/ Engl. translation).
Letter from counsel for Purdue Pharma LP, dated Dec. 20, 2007, to EPO re EP–B–964677 opposition proceedings (English).
Summons to attend oral proceedings pursuant to Rule 115(1) EPC re EP–B–964677 opposition proceedings dated Dec. 29, 2008.
Letter from counsel for Acino AG (previously Novosis AG), dated Apr. 17, 2009, to EPO re EP–B–964677 opposition proceedings. (in German, w/ Engl. translation).
Letter from counsel for Purdue Pharma LP, dated Apr. 23, 2009, to EPO re EP–B–964677 opposition proceedings (English).
Letter from counsel for Purdue Pharma LP, dated Jun. 4, 2009, to EPO re EP–B–964677 opposition proceedings (English).
Minutes of the oral proceedings before the Opposition Division held Jun. 23, 2009 re: EP–B–964677.
Decision revoking the European Patent EP–B–964677, dated Jul. 24, 2009.
Japanes Supreme Court, Third Petty Branch decision dated Jan. 16, 2007. (English translation).
Abse et al., "The poppy: therapeutic potential in cases of dementia with depression" *Ann. NY Acad. Sci.* 398: 79–83 (1982).*
Ahmedzai, S, "New approached to pain control in patients with cancer" *Eur. J. Cancer* 33(Suppl. 6): S8–S14 (1997).*
Akatsuka et al., "The relief of postoperative pain by suppositories of buprenorphine or NSAID" *Masui* 45(3): 298–303 (1996). (Abstract).*
Al–Gommer O. Sexual dysfunctions in male opiate users: A comparative study of heroin, methadone, and buprenophine. *Addictive Disorders and their Treatment* 2007; 6(3):137–43.*
Ang–Lee K. Single dose of 24 milligrams of buprenorphine for heroin detoxification: An open–label study of five inpatients. *Journal of psychoactive drugs* 2007; 38(4):505–12.*
*Bates' Guide to Physical Examination and History Taking*, 6th ed., Bickley t al., eds., Lippincott Williams & Wilkins Publishers, 1995, pp. 276–280.*
Bellamy N, Buchanan W W, Goldsmith CH, Campbell J, Stitt LW. Validation study of WOMAC: a health status instrument for measuring clinically important subject relevant outcomes to antirheumatic drug therapy in subjects with osteoarthritis of the hip or knee. *J Rheumatol* 1988; 15:1833–1840.*
Bellamy N, Campbell J, Hill J, Band P. A comparative study of telephone versus onsite completion of the WOMAC: 3.0 Osteoarthritis Index. *J Rheumatol* 2002; 29:783–786.*
Bellamy N. *WOMAC Osteoarthritis Index. a user's guide*. London, Ontario, Canada: Victoria Hospital Corporation, 1995.*
Bentley et al., "Age and fentanyl pharmacokinetics" *Anesth. Analg.* 61: 968–971 (1982).*
Berrocoso et al., "Differential role of 5–HT1A and 5–HT1B receptors on the antinociceptive and antidepressant effect of tramadol in mice" *Psychopharmacology* 188(1): 111–118 (2006).*
Bodkin et al., "Buprenorphine treatment of refractory depression" *J. Clin. Psychopharmacology*, 15(1): 49–57 (1995).*
Bonica, JJ, "Past and current status of pain research and therapy" *Semin. Anesth.* 5:82–99 (1986).*
Brema et al., "Oral tramadol and buprenorphine in tumor pain. An Italian multicentre trial" *Int. J. Clin. Pharm. Rex.* 16(⁴⁄₅): 109–116 (1996).*
Brenn et al., "Epidural analgesia in children with cerebral palsy" 45(12): 1156–1161 (1998).*
Buchwald et al., "Quantitative structure–metabolism relationships: Steric and non–steric effects in the enzymatic hydrolysis of noncongener carboxylic esters" *J. Med. Chem.* 42:5160–5168 (1999).*
Bundgaard, H (ed.) *Design of Prodrugs* Elsevier: Amsterdam, New York 1985.
Callaway, E., "Buprenorphine for depression: The un–adoptable orphan" *Biol. Psychiatry* 39: 989–990 (1996).
Callesen et al., "Prospective study of chronic pain after groin hernia repair" *Br. J. Surg.* 86: 1528–1531 (1999).

Capogna et al., "Intrathecal buprenorphine for postoperative analgesia in the elderly patient" *Anaesthesia* 43: 128–130 (1988).
Cathelin et al., "Comparison between the side–effects of buprenorphine and morphine in conscious man" *Anesth. Analg.* (Paris) 37(5–6): 283–293 (1980). English abstract. (Original in French).
Cherny, J., "New strategies in opioid therapy for cancer pain" *J. Oncol. Management* 9: 8–15 (2000).
Cirado et al., "Reduction of isoflurane MAC with buprenorphine and morphine in rats" *Laboratory Animals* 34(3): 252–9 (2000).
Cleeland CS, Ryan KM. Pain assessment: global use of the Brief Pain Inventory. *Ann Acad Med* 1994;23(2):129–138.
Coli et al., "Evaluation of the effectiveness of NSAIDs in the prevention of postoperative pain. Comparison between pre– and postoperative administration of sodium naproxen in orthopedic surgery" *Minerva Anestesiol.* 59(10): 531–535 (1993). (Abstract).
Crook et al., "The prevalence of pain complaint in a general population" *Pain* 18: 299–314 (1984).
Daut RL, Cleeland,CS, Flanery RC. Development of the Wisconsin Brief Pain Questionnaire to assess pain in cancer and other diseases. *Pain* 1983; 17:197–210.
Davids et al., "Buprenorphine in the treatment of opioid dependence" *European Neuropsychopharmacology* 14: 209–216 (2004).
Dayer et al., "Pharmacology of tramadol" *Drugs* 53(Suppl. 2): 18–24 (1997). English abstract. (Original in French).
Dean et al., "Depressive symptoms during buprenorphine vs. methadone maintenance: Findings from a randomized, controlled trial in opioid dependence" *European Psychiatry* 19: 510–513 (2004).
Desjardins et al., "The injectable cyclooxegenase–2 specific inhibitor parecoxib sodium has analgesic efficacy when administered preoperatively" *Anesth. Analg.* 93: 721–727 (2001).
Dionne et al., "Evaluation of preoperative ibuprofen for postoperative pain after removal of third molars" *Oral Surgery* 45: 851–856 (1978).
Dionne et al., "Suppression of postoperative pain by preoperative administration of ibuprofen in comparison to placebo, acetaminophen, and acetaminophen plus codeine" *J. Clin. Pharmacol.* 23: 37–43 (1983).
Dum et al., "Opioids and Motivation" *Interdisciplinary Science Reviews* 12(2): 180–190 (1987).
Eder et al., "Buprenorphine in der Schwangerschaft" *Psychiat. Prax.* 28: 267–269 (2001). (XP009068360). (Abstract).
Eke et al., "An open comparative study of dispersible piroxicam versus soluble acetylsalicylic acid for the treatment of osteoarticular painful attack during sickle cell crisis" *Tropical Medicine and International Health* 5(2): 81–84 (2000).
Emrich et al. "Antidepressant effects of buprenorphine" *Lancet* 2: 709 (1982).
Emrich et al., "Current perspectives in the pharmacopsychiatry of depression and mania" *Neuropharmacology* 22(3 Special No.): 385–388 (1983).
Emrich et al., "Possible antidepressive effects of opioids: action of buprenorphine" *Ann. NY Acad. Sci.* 398: 108–112 (1982).
Emrich, HM, in: "Typical and Atypical Antidepressant: Clinical Practice" Costa et al., (Eds.), Raven Press: New York, 1982 pp. 77 et seq.
Holloway, M. (Erickson, D.), "Rx for addiction" *Sci. Am.* 264(3): 94–103 (1991).
Etchepare F, Coutaux A, Edel Y, Bourgeois P. *Enterobacter cloacae* spondylodiscitis through misuse of high–dose intravenous buprenorphine. *La Presse Medicale* 2005; 34(10):729–731.
Everhart et al., "Subnanogram–concentration measurement of buprenorphine in human plasma by electron–capture capillary gas chromatography: application to pharmacokinetics of sublingual buprenorphine" *Clin. Chem.* 43(12): 2292–2302 (1997).
Extein et al., "Deficient prolactin response to morphine in depressed patients" *Am. J. Psychiatry* 137: 845–846 (1980).
Extein et al., "Methadone and morphine in depression" *Psychopharmacol. Bull.* 17(1): 29–33 (1981).
Faponle, AF, "Management of pain after surgery—A Short Review " *Nigerian Journal of Medicine* 10(3): 112–115 (Jul./Sep. 2001).
Feinberg et al., "The effect of morphine on symptoms of endogenous depression" in: Harris,(ed.) *Problems of Drug Dependence,* 1982 *National Institute on Drug Abuse Research Monograph* 43 pp. 245–250 (1982).
Ferrell et al., "Principles of pain management in older people" *Compr. Ther.* 17: 53–58 (1991).
Ferrell, BA, "Pain avaluation and management in the nursing home" *Ann. Int. Med.*123(9): 681–687 91995).
Fischer et al., "Treatment of opioid–dependent pregnant women with buprenorphine" *Addiction* 95(2): 239–244 (2000). (Abstract).
Fletcher D, "Prevention of postoperative pain" *Ann. Fr. Anesth. Reanim.* 17(6): 622–632 (1998). (Abstract).
Gautschi OP, Zellweger R. Images in emergency medicine. Extensive groin abscess and myositis after intravenous cubital buprenorphine injection. *Annals of Emergency Medicine* 2006; 48(6): 656–659.
Gerra et al., "Buprenorphine treatment outcome in dually diagnosed heroin dependent patients: A retrospective study" *Progress in Neuro–Psychopharmacology & Biological Psychiatry* 30: 265–272 (2006).
Gerra et al., "Buprenorphine versus methadone for opioid dependence: predictor variables for treatment outcome" *Drug and Alcohol Dependence* 75: 37–45 (2004).
Glasper et al., "Induction of patients with moderately severe methadone dependence onto buprenorphine" *Addiction Biology* 10: 149–155 (Jun. 2005).
Gold et al., "Antimanic, antidepressant, and antipanic effects of opiates: clinical, neuroanatomical, and biochemical evidence" *Ann. NY Acad. Sci.* 398: 140–150 (1982).
Gold et al., "Clinical evidence of antidepressant and antipanic effects of opiates" *Am. J. Psychiatry* 136: 982–983 (1979).
Goldstein, "Methadone for depression" *Biol. Psychiatry* 19: 1272–1273 (1984).
Golianu, B., "Pediatric acute pain management" *Pediatr. Clin. North Am.* 47(3): 559–587 (2000).
Goodman & Gilman's *The Pharmacological Basis of Therapeutics Hardman, JG (ed.) McGraw–Hill Professional Publishing*, 2001, p. 586.
Goodman & Gilman's *The Pharmacological Basis of Therapeutics* Hardman, JG (ed.) McGraw–Hill Professional Publishing, 2001, pp. 31–32.
Goodman & Gilman's *The Pharmacological Basis of Therapeutics* Hardman, JG (ed.) Mc–Graw–Hill Professional Publishing, 2001, pp. 530–532.

Griffin et al., "High–dose intravenous methylprednisolone therapy for pain in children and adolescents with sickle cell disease" *N. Engl. J. Med.* 330(11): 733–737 (1994).
*Guideline for Industry—Clinical Safety Data management: Definitions and Standards for Expedited Reporting* ICH–E2A, Mar. 1995, pp. 5–7.
Hambrook JM, Rance MJ. The interaction of buprenorphine with opiate receptor: lipophilicity as a determining factor in drug–receptor kinetics. In: Kosterlitz HW, editor. *Opiates and endogenous opioid peptides*. Amsterdam: Elsevier/North Holland, Biomedical Press; 1976. p. 295–301.
Hannibal et al., "Preoperative wound infiltration with bupivacaine reduces early and late opioid requirement after hysterectomy" *Anesth. Analg.* 83: 376–381 (1996).
Heel et al., *Curr. Ther.* 5: 29–33 (1979).
Hoffman D, Friedman M, Colucci S, Richards, P, Zhang P. Validation of the Brief Pain Inventory for subjects with osteoarthritis. *J Pain* 2002; 3(2):(Suppl)3.
Huang et al., "Atmospheric pressure ionization mass spectrometry" *Anal. Chem.* 62(13): 713A–725A (1990).
Inagaki et al., "Mode and site of analgesic action of epidural buprenorphine in humans" *Anesth. Analg.* 830: 530–536 (1996).
International Search Report, PCT/US2003/039793, dated Mar. 31, 2004, 2ppgs.
Jacobsen et al., "Age–related changes in sebaceous wax ester secretion rates in men and women" *J. Invest. Dermatol.* 85: 483–485 (1985).
Jakobovits SL, Mcdonough M, Chen RY. Buprenorphine–associated gastroparesis during in–patient heroin detoxification. *Addiction* 2007, 101:490–491.
Jernite et al., "Buprenorphine and pregnancy. Analysis of 24 cases" *Arch. Pediatr.* 6:1179–1185 (1999).
Juhlin–Dannfelt et al., "Premedication with sublingual buprenorphine for out–patient arthroscopy: Reduced need for postoperative pethidine but higher incidence of nausea" *Acta Anaesthesio. Scand.* 39: 633–636 (1995).
Kaliha H. A prospective study on buprenorphine use during pregnancy: Effects on maternal and neonatal outcome. *Acta Obstetricia et Gynecologica Scandinavica* 2007; 86(2): 185–90.
Kaliha H. Brain magnetic resonance imaging of infants exposed prenatally to buprenorphine. *Acta Radiologica* 2007; 48(2): 228–31.
Kakinohana et al., "Pre–emptive analgesia with intravenous ketamine reduces postoperative pain in young patients after appendectomy: A randomized control study" *Masui* 49(10): 1092–1096 (2000). (Abstract).
Kalbfleisch JD, Prentice RL. *The statistical analysis of failure time data.* New York: John Wiley and Sons (2nd edition). 2002, pp. 22–23.
Kenny et al., *Clin. Geriatr.* 8: 1–4 (2000).
Kinney et al., AACN's Clinical Reference Clinical Reference for Critical Care Nursing, Mosby, 4th ed., 1998, pp. 285–287.
Kokki et al., "Comparison of pre–and postoperative administration of ketoprofen for analgesia after tonsillectomy in children" *Pediatric Anesthesia* 12(2): 162–167 (2002).
Kosten et al., "Depressive symptoms during buprenorphine treatment of opioid abusers" *Journal of Substance Abuse Treatment* 7: 51–54 (1990).
Lehmann et al., "Treatment of depression with dexedrine and demerol" *Curr. Therapeutic Res. Clin. Exp.* 13(1): 42–49 (1971).
Lichtenstein et al., "Disaggregating pain and its effect on physical functional limitations" *J. Gerontol* 53(5): M361–M371 (1998).
Lintzeris N. Interactions on mixing diazepam with methadone or buprenorphine in maintenance patients. *Journal of clinical psychopharmacology* 2006; 26(3):274–283.
Lovell et al., "Type I and III collagen content and fibre distribution in normal human skin during ageing" *Br. J. Dermatol.* 117: 419–328 (1987).
Luukinen et al., "Prognosis of diastolic and systolic orthostatic hypotension in older persons" *Arch. Int. Med.* 159: 273–280 (1999).
Marek, GJ "Behavioral evidence for μ–opioid and 5–HT2A receptor interactions" *European Journal of Pharmacology* 474: 77–83 (2003).
Markowitz et al., "Venlafaxine–tramadol similarities" *Med. Hypotheses* 51(2): 167–168 (1998).
Maruyama S, Nomura Y, Fukushige T, Eguchi T, Nishi J, Yoshinaga M, Kawano Y. Suspected Takotsubo cardiomyopathy caused by withdrawal of buprenorphine in a child. *Circulation Journal* 2006; 70:509–511.*
Matussek et al., "Investigations with the specific μ–opiate receptor antagonist fentanyl in depressive patients: Growth hormone, prolactin, cortisol, noradrenaline and euphoric responses" *Neuropsychobiology* 21: 1–8 (1989).*
McCance–Katz EF. Interaction between buprenorphine and atazanavir/ritonavir. *Drug and Alcohol Dependence* 2007; 91(2–3):269–78.*
Mello et al., "Buprenorphine treatment of opirate and cocaine abuse: Clinical and Preclinical studies" *Harvard Rev. Psychiatry* 1: 168–183 (1993).*
Melon et al., "Buprenorphine. Haemodynamic study" *Anesth. Analg.* (*Paris*) 37(3–4): 121–125 (1980). English abstract. (Original in French.).*
Mendelson et al., "Dose proportionality of 4, 8, 16 and 32 mg sublingual buprenorphine solutions" *American Society for Clinical Pharmacology and Therapeutics* 65(2): 154 Abstract P11–28 (1999).*
Mercadante et al., "Alternatives to oral opioids for cancer pain" *Oncology* 13(2): 215–220 (1999).*
Mercadante, "Opioid rotation in cancer pain: rationale and clinical aspects" *Cancer* 86:1 1856–66 (1999).*
Mobily et al., "An epidemiologic analysis of pain in the elderly" *J. Aging Health* 6: 139–154 (1994).*
Mongan et al., "Buprenorphine responders" *Biol. Psychiatry* 28: 1078–1080 (1990).*
Moragas et al., "Image analysis of dermal collagen changes during skin aging" *Analyt. Quant. Cytol. Histol.* 20: 493–499 (1998).*
Nanovskaya et al., "Transplacental transfer and metabolism of buprenorphine" *J. Pharmacol. Exp. Ther.* 300(1): 26–33 (2002).*
Noble et al., "Protection of endogenous enkephalin catabolism as natural approach to novel analgesic and antidepressant drugs" *Expert Opinion on Therapeutic Targets* 11(2): 145–159 (Nov. 2007).*
Nolan et al., "Anaesthesia and pain management in cerebral palsy" *Anaesthesia* 55:(1): 32–41 (2000).*
Nyhuis et al., "Opiate receptors in ECT—resistant depression" *European Neuropsychopharmacology* 15(3): S420 (2005).*
Oda et al., "Fentanyl inhibits metabolism of midazolam: competitive inhibition of CYP3A4 in vitro" *Br. J. Anaesthesia* 82(6): 900–903 (1999).*

Oliveto et al., "Desipramine, amantadine, or fluoxetine in buprenorphine–maintained cocaine users" *Journal of Substance Abuse Treatment* 12(6): 423–428 (1995).*

Paetzold et al., "Buprenorphine: therapeutical use in opioid–dependence, depression and schizophrenia" *Nervenheilkunde* 19(3): 143–150 (2000). (w/ English abstract).*

Pani et al., "Buprenorphine: A controlled clinical trial in the treatment of opioid dependence" *Drug and Alcohol Dependence* 60: 39–50 (2000).*

Parmelee et al., "Assessment of pain in the elderly" *Annual Review of Gerontology and Geriatrics* 14: 281–301 (1994).*

Pereira et al., "Analgesic effects of diclofenac suppository and injection after postoperative administration" *Int. J. Clin. Pharm. Res.* 19(2): 47–51 (1999).*

Perttunen et al., "Chronic pain after thoracic surgery: a follow–up study" *Acta Anaesthesiol. Scand.* 43: 563–567 (1999).*

Pickar et al., "Behavioral and biological effects of acute beta–endorphin injection in schizophrenic and depressed patients" *Am. J. Psychiatry* 138: 160–166 (1981).*

Potter, *Fundamentals of Nursing,* Mosby, 4th ed., 1997, p. 633.*

Reddy L, Kranjnik M, Zylicz Z. Transdermal buprenorphine may be effective in the treatment of pruritus in primary biliary cirrhosis. *Journal of Pain and Symptom Management* 2007; 34(5):455–456.*

Romero et al., "Opioid peptide receptor studies. 12. Buprenorphine is a potent and selective μ/κantagonist in the [$^{35}$S]–GTP–γ–S functional binding assay" *Synapse* 34: 83–94 (1999).*

Rooke et al., "Maximal skin blood flow is decreased in elderly men " *J. Appl. Physiol.* 77: 11–14 (1994).*

Rothman et al., "An open–label study of a functional opiod κ antagonist in the treatment of opioid dependence" *Journal of Substance Abuse Treatment* 18: 277–281 (2000).*

Russo and Brose, *Ann. Rev. Med.* 49: 123–133 (1998).*

Schriek P. Treatment of cancer–related pain with transdermal buprenorphine: a report of three cases. *European Support Care Cancer* 2004; 12:882–884.*

Seet RCS, Lim ECH. Intravenous use of buprenorphine tablets associated with rhabdomyolysis and compressive sciatic neuropathy. *Annals of Emergency Medicine* 2006; 47(4):396–397.*

Seet RCS, Rathakrishnan R, Chan BP, Lim ECH. Diffuse cystic leucoenphalopathy after buprenorphine injection. *Journal of Neurology, Neurosurgery and Psychiatry* 2005; 76(6):890–891.*

Seidenari et al., "Echographic evaluation with image analysis of normal skin: variation according to age and sex" *Skin Pharmacol.* 7:201–209 (1994).*

Seifert et al., "Detoxification of opiate addicts with multiple drug abuse: a comparison of buprenorphine vs. methadone" *Pharmacopsychiatry* 35: 159–164 (2000).*

Seifert et al., "Mood and affect during detoxification of opiate addicts: A comparison of buprenorphine versus. methadone" *Addiction Biology* 10: 157–164 (Jun. 2005).*

Shapira et al., "Treatment of refractory major depression with tramadol monotherapy" *Am. J. Psychiatry* 62(3): 205–206 (2001).*

Ssheikh et al., "Geriatric Depression Scale: Recent evidence and development of a shorter version" *Clin. Gerontol.* 5: 165–173 (1986).*

Singh J, Grover S, Basu D. Very high–dose intravenous buprenorphine dependence: A case report. *German J Psychiatry* 2004; 7:58–59.

Soyka M, Penning R, Wittchen U. Fatal poisoning in methadone and buprenorphine treated patients—are there differences? *Pharmacopsychiatry* 2006; 39:85–87.

Spyker et al., *Clin. Pharmacol. Ther.* 67(2): 145, Abstract P11–12.

Stanway, GW, "A preliminary investigation comparing pre–operative morphine and buprenorphine for postoperative analgesia and sedation in cats" *Veterinary Anaesthesia and Analgesia* 29: 29–35 (2002).

Stewart et al., eds., "Medical Outcomes Study Pain Evaluation" in: *Measuring Functioning and Well–Being—The Medical Outcomes Study Approach,* Durham and London: Duke University Press, 1992.

Stinchcomb et al., "A solubility and related physicochemical property comparison of buprenorphine and its 3–alkyl esters" *Pharmaceutical Research* 12(10): 1526–1529 (1995).

Supplementary partial European Search Report for EP Application No. 03721427, dated Mar. 31, 2006.

Tanaka et al., "Preoperative fluribiprofen provides pain relief after laparascopic cholecystectomy" *Masui* 46(5): 679–683 (1997). Abstract).

Tauzin–Fin et al., "Effect of balanced analgesia with buprenorphine on pain response and general anesthesia requirement during lithotripsy procedures" *European Journal of Anaesthesiology* 15: 147–152 (1998).

Thompson et al., "Perioperative pharmacokinetics of transdermal fentanyl in elderly and young adult patients" *Br. J. Anaesth.* 81: 152–154 (1998).

Torrens et al., "Buprenorphine versus heroin dependence: Comparison of toxicologic and psychopathologic characteristics" *Am. J. Psychiatry* 150(5): 822–824 (1993).

Varga et al., "The effect of codeine on involutional and senile depression" *Ann. NY Acad. Sci.* 398: 103–105 (1982).

Verhaeverbeke et al., "Drug–induced orthostatic hypotension in the elderly: avoiding its onset" *Drug Safety* 17: 108–118 (1997).

Vibbert et al., eds., "Modified Brief Pain Inventory," in: *The 1995 Medical Outcomes and Guidelines Sourcebook,*New York: Faulkner & Gray, Inc., 1994, pp. 269–270.

Walsh et al., "Acute administration of buprenorphine in humans: Partial agonist and blockade effects" *The Journal of Pharmacology and Experimental Therapeutics* 274(1): 361–372 (1995).

Weber et al., "Current and historic concepts of opiate treatment in psychiatric disorders" *Int. Clin. Psychopharmacology* 3: 255–266 (1988).

Weiss et al., "Analysis of the diminished skin perfusion in elderly people by laser doppler flowmetry" *Age Ageing* 21: 237–241 (1992).

Williams et al., "Case–finding for depression in primary care: a randomized trial" *Am. J. Med.* 106(1): 36–43 (1999).

Woods et al., "Efficacy of nalbuphine as a parenteral analgesic for the treatment of painful episodes in children with sickle cell disease" *J. Assoc. Acad. Minor Phys.* 1(3): 90–92 (1990).

Yashiki et al., "Dual mass spectrometry of trifluoroacetyl derivatives of opioid bases" *GC–MS News* 13(4): 101–106 (1985).

Yassen A. Mechanism–based pharmacokinetic–pharmacodynamic modeling of the reversal of buprenorphine–induced respiratory depression by naloxone: a study in healthy volunteers. *Clinical Pharmacokinetics* 2007; 46(11):965–80.
Yaster et al., "Epidural analgesia in the management of severe vaso–occlusive sickle cell crisis" *Pediatrics* 93(2): 310–315 (1994).
Yaster et al., "The management of pain in sickle cell disease" *Pediatr. Clin. North Am.* 47(3): 699–710 (2000).
Office Actions issued in the prosecution of U.S. Appl. No. 08/939,068 to Reder et al., filed Sep. 29, 1997.
Office Actions issued in the prosecution of U.S. Appl. No. 09/311,997 to Reder et al., filed Jun. 14, 1999.
Office Actions issued in the prosecution of U.S. Appl. No. 09/756,419 to Reder et al., filed Jan. 18, 2001.
Office Actions issued in the prosecution of U.S. Appl. No. 10/033,056 to Reder et al., filed Dec. 27, 2001.
Office Actions issued in the prosecution of U.S. Appl. No. 10/394,425 to Kaiko et al., filed Mar. 27, 2003.
Office Actions issued in the prosecution of U.S. Appl. No. 10/402,288 to Reder et al., filed Mar. 28, 2003.
Office Actions issued in the prosecution of U.S. Appl. No. 10/476,601 to Tavares et al., filed Nov. 20, 2003.
Office Actions issued in the prosecution of U.S. Appl. No. 10/736,043 to Reidenberg et al., filed Dec. 15, 2003.
Office Actions issued in the prosecution of U.S. Appl. No. 10/736,049 to Reidenberg et al., filed Dec. 15, 2003.
Office Actions issued in the prosecution of U.S. Appl. No. 11/033,106 to Reder et al., filed Jan. 11, 2005.
Office Actions issued in the prosecution of U.S. Appl. No. 11/033,107 to Reder et al., filed Jan. 11, 2005.
Office Actins issued in the prosecution of U.S. Appl. No. 11/033,108 to Reder et al., filed Jan. 11, 2005.
Catapres TTS® Product Information, Physicians' Desk Reference 1998, pp. 610–612.
Climara® Product Information, Physicians' Desk Reference 1998, pp. 672–6.
Kuhlman, Jr., et al., Human pharmacokinetics of intravenous, sublingual, and buccal buprenorphine. J Anal Toxicol. Oct. 1996;20(6):369–78.
McQuinn, R.L. et al., Sustained oral mucosal delivery in human volunteers of buprenorphine from a thin non–croding mucoadhesive polymeric disk. Journal of Controlled Release 1995, 34:243–50.
Roy et al., Transdermal Delivery of Buprenorphine through Cadaver Skin. J Pharma Sci 1994, 83(2):126–30.
Sadee et al., Buprenorphine: Differential interaction with opiate receptor subtypes in vivo. The Journal of Pharmacology and Experimental Therapeutics, Copyright © 1982, 223(1):157–62.
Van Buskirk et al, Scale–up of adhesive transdermal drug delivery systems. Pharmaceutical Research 1997, 14(7).
Wilding et al., Pharmacokinetic evaluation of transdermal buprenorphine in man. International Journal of Pharmaceutics 1996, 132:81–7.
Ashcroft et al., Buprenorphine TDS: Comparison with sublingual buprenorphine in osteoarthritic pain. 10$^{th}$ World Congress on Pain, Aug. 19, 2002 Abstract 510–P144.
Becker et al., Transdermal buprenorphine: Abuse potential assessment in non–opioid–dependent volunteers. CPDD Jun. 16–21, 2001 Abstract 40 (w/ PowerPoint presentation).
Boas et al., Clinical actions of fentanyl and buprenorphine the significance of receptor binding. Br. J. Anaesth. 1985, 57:192–6.
Buprenorphine Product Photo, Norspan™ 5, 10 & 20.
Capurso et al., Matrix transdermal technology: focus on a buprenorphine transdermal system. ASHP Midyear Clinical Meeting, Dec. 2001, p. 231D Abstract (w/ PowerPoint presentation).
Colucci, History of Buprenorphine. PowerPoint presentation presented in Dec. 2002.
El–Tahtawy et al., 7–Day bioavailability of buprenorphine from a novel transdermal system in demographic subgroups. 13$^{th}$ Annual ACCP Meeting Abstracts, Sep. 23–25, 2001, p. 1027, Abstract 56 (w/ PowerPoint presentation).
Friend et al., Simple alkyl esters as skin permeation enhancers. J. Controlled Release 1988 9:33–41.
Friend et al., Transdermal delivery of levonorgestrel I: Alkanols as permeation enhancers in vitro, Controlled Release 1988 7:243–50.
Hale et al., Analgesic efficacy of buprenorphine transdermal system vs. Oxy/APAP in patients with chronic low back pain. The Gerontologist, vol. 41, Special Issue Oct. 1, 2001, Program Abstracts from the Gerontological Society of America 54$^{th}$ Annual Scientific Meeting, Nov. 15–18, 2001, p. 25 (w/ PowerPoint presentation first presented on May 7, 2002 and revised on Oct. 30, 2002).
Hale et al., Dose proportionality and the dose response of buprenorphine transdermal system in patients with chronic pain. 13$^{th}$ Annual ACCP Meeting Abstracts, Sep. 23–25, 2001, p. 1027, Abstract 58 (w/ PowerPoint presentation).
Hale et al., Long–term use of buprenorphine transdermal system (BTDS) in patients with chronic pain. PowerPoint presentation presented May 2002.
Hale et al., Treatment of patients with chronic low back pain with buprenorphine transdermal systems (BTDS) compared with hydrocodone/acetaminophen. National Clinical Symposium of the American College of Nurse Practitioners, Oct. 20, 2001 Abstract (w/ PowerPoint presentation).
Jaffe et al., Opioid Analgesics and Antagonists. The Pharmacological Basis of Therapeutics (8$^{th}$ ed. Pergamon Press) 1990, Chap. 21, pp. 485–521.
Jeal et al., Transdermal fentanyl. A review of its pharmacological properties and therapeutic efficacy in pain control. Drugs, Jan. 1997, 53(1):109–38. Review.
Kaiko et al., Transdermal buprenorphine. Memorial Sloan Kettering Manuscript, Chapter 15 (w/ PowerPoint Final presentation presented May, 2, 2003).
Lasseter et al., Systemic pharmacokinetic (PK) Study of buprenorphine (B) in mild to moderate chronic hepatic impairment (CHI). Amer. Society for Clinical Pharmacology and Therapeutics 69(2) 2 (P1–4) Feb. 2001 Abstract (w/ PowerPoint presentation presented Mar. 2001).
Marquardt et al., Fentanyl remaining in a transdermal system following three days of continuous use. Ann Pharmacother Oct. 1995, 29(10):969–71.
Müller et al., Intra—and postoperative interactions between the 2 opioid fentanyl and buprenorphine. Anaesthesist. Apr. 1986, 35(4):219–25 (in German, w/ English abstract).
Noveck et al., Pharmacokinetics of buprenorphine transdermal system (BTDS 10) employing the LPS pyrogen model. Clinical Pharmacology & Therapeutics 69(2):3 200 2001 Abstract P1–7 (w/ PowerPoint presentation).
Payne et al., Guidelines for the clinical use of transdermal fentanyl. Anticancer Drugs. Apr. 6, 1995, Suppl 3:50–3.
Peng et al., A review of the use of fentanyl analgesia in the management of acute pain in adults. Anaesthesiology 1999, 90:576–99.

Reidenberg et al., Absolute bioavailability of a novel buprenorphine transdermal system (BTDS) applied for 7 days. J. Clin Pharmacol. 41(9) 2001 Abstract 55 (w/ PowerPoint presentation presented in the ACCP Meeting, Sep. 2001).
Reidenberg et al., Daily pharmacokinetic performance of a buprenorphine transdermal system (BTDS) for up to 7 days. Abstract 13th Annual ACCP Meeting, Sep. 23–25, 2001, p. 1027 Abstract 57 (w/ PowerPoint presentation).
Reidenberg et al., Pharmacokinetics and safety of buprenorphine transdermal system (BTDS) for 7–Day application comparing healthy elderly and young adult subjects. Am Pain Soc, 19th Ann. Sci. Meet., Nov. 2–5, 2000 Abstract 776 (w/ PowerPoint presentation).
Reidenberg et al., Physiologic effects of buprenorphine transdermal system (BTDS) dose escalation in the young, healthy elderly and elderly hypertensive subjects, FASEB J. 15(4), Mar. 2001 Abstract 457.3 (w/ PowerPoint presentation presented Apr. 2001).
Roy et al., "Controlled transdermal delivery of fentanyl: characterization of pressure–sensitive adhesives for matrix patch design," J Pharm Sci. May 1996, 85(5):491–5.
Sandler et al., A Double–blind, placebo—controlled trial of transdermal fentanyl after abdominal hysterectomy. Analgesic, respiratory, and pharmacokinetic effects, Anesthesiology Nov. 1994, 81(5):1169–80; discussion 26A.
Spyker et al., Effectiveness and safety of buprenorphine transdermal system (BTDS) compared with hydrocodone/acetaminophen in the treatment of patients with chronic back pain. J. Pain 2002 3(Suppl. 1):14 Abstract 653 (w/ PowerPoint presentation).
Spyker et al., Effectiveness of buprenorphine transdermal system (BTDS) compared with oxycodone/acetaminophen and placebo in the treatment of patients with chronic back pain. Morial Convention Center, Oct. 15, 2001 Abstract (w/ PowerPoint presentation).*
Spyker et al., Transdermal buprenorphine system (BTDS) in patient–controlled Analgesia (PCA). PowerPoint presentation presented Mar. 2000.*
Spyker et al., Analgesic efficacy and safety of buprenorphine transdermal system (BTDS) in patients with osteoarthritis. The Journal of Pain 3(2, Suppl. 1):12 Abstract 645(w/ PowerPoint presentation).*
Spyker et al., Effect Size (ES) Meta–analysis Approach to Noninferioity Clinical Pharmacology & Therapeutics 69(2):33 Abstract PII–3 (w/ PowerPoint presentation presented Mar. 5, 2001). 0.*
Transtec Summary of Product Characteristics, Oct. 2003.*
Ashcroft et al., Buprenorphine TDS: Comparison with sublingual buprenorphine in osteoarthritic pain. 10th World Congress on Pain, Aug. 19, 2002 Abstract 510–P144.*
Becker et al., Transdermal buprenorphine: Abuse potential assessment in non–opioid–dependent volunteers. CPDD Jun. 16–21, 2001 Abstract 40 (w/ PowerPoint presentation).*
Boas et al., Clinical actions of fentanyl and buprenorphine the significance of receptor binding. Br. F. Anaesth. 1985, 57:192–6.*
Hale et al., Analgesic efficacy of buprenorphine transdermal systems vs. Oxy/APAP in patients with chronic low back pain. The Gerontologist from the Gerontological Society of America 54th Annual Scientic Meeting, Nov. 15–18, 2001, p. 25 (w/ PowerPoint presentation first presented on May 7, 2002 and revised on Oct. 30, 2002).*
Kaiko et al., Transdermal burenorphine. Memorial Sloan Kettering Manuscript, Chapter 15 (w/ PowerPoint Final presentation presented May, 2, 2003).*
Lasseter et al., Systemic pharmacokinetic (PK) Study of burenorphine (B) in mild to moderate chronic hepatic impairment (CHI). Amer. Society for Clinical Pharmacology and Therapeutics 69(2) 2 (P1–4) Feb. 2001 Abstract (w/ PowerPoint presentation presented Mar. 2001).*
Noveck et al., Pharmacokinetics of burenorphine transdermal system (BTDS 10) employing the LPS pyrogen model. Clinical Pharmacology & Therapeutics 69(2):3 200 2001 Abstract P1–7 (w/ PowerPoint presentation).*
Reidenberg et al., Daily pharmacokinetic performance of a burenorphine transdermal system (BTDS) for up to 7 days. Abstract 13th Annual ACCP Meeting, Sep. 23–25, 2001, p. 1027 Abstract 57 (w/ PowerPoint presentation).*
Sandler et al., A double–blind, placebo–controlled trial of transdermal fentanyl after abdominal hysterectomy. Analgesic, respiratory, and pharmacokinetic effects. Anesthesiology Nov. 1994, 81(5): 1169–80; discussion 26A.
Spyker et al., Analgesic efficacy and safety of buprenorphine transdermal system (BTDS) in patients with osteoarthritis. The Journal of Pain 3(2, Suppl. 1):12 Abstract 645(w/ PowerPoint presentation).
Spyker et al., Effectiveness of buprenorphine transdermal system (BTDS) compared with oxycodone/acetaminophen and placebo in the treatment of patients with chronic back pain. Morial Convention Center, Oct. 15, 2001 Abstract (w/ PowerPoint presentation).
Spyker et al., Effectiveness and safety of buprenorphine transdermal system (BTDS) compared with oxycodone/acetaminophen and placebo in the treatment of patients with chronic back pain. J. Pain 2002 3(Suppl. 1):14 Abstract 653(w/ PowerPoint presentation).
Spyker et al., Effect Size (ES) Meta–analysis Approach to Noninferioity Clinical Trials. Clinical Pharmacology & Therapeutics 69(2):33 Abstract PII–3 (w/ PowerPoint presentation presented Mar. 5, 2001).
Adriaensen et al., A long–term open, clinical and pharmacokinetic assessment of sublingual buprenorphine in patients suffering from chronic pain. Acta Anaesthesiol Belg. Mar. 1985;36(1):33–40.
Amass et al. A preliminary investigation of outcome following gradual or rapid buprenorphine detoxification. J Addict Dis. 1994; 13:33–45.
Amass et al., Alternate–day dosing during buprenorphine treatment of opioid dependence. Life Sci. 1994;54:1215–28.
Amass et al., Detectability of buprenorphine dose alternations in opioid–dependence humans. NIDA Res Monogr. 1993; 132–335.
Arditti et al., [Buprenorphine abuse in a series of 50 drug addicts hospitalized at a drug dependence evaluation hospital center of Marseille] Therapie. 1992; 47:561–2. [in French w/ English transl].
Banerjee et al., Haematological changes in buprenorphine–treated mice. Folia Biol (Krakow). 1997;45(3–4):157–62.
Banks. Overdosage of buprenorphine: case report. N Z Med J. 1979; 89:255–6.
Banys et al. An open trial of low dose buprenorphine in treating methadone withdrawal. J Subst Abuse Treat. 1994; 11:9–15.
Barrett et al. The pharmacokinetics and physiological effects of buprenorphine infusion in premature neonates. Br J Clin Pharmacol. Sep. 1993;36(3):215–9.

Barron et al. Prenatal buprenorphine exposure and sexually dimorphic nonreproductive behaviors in rats. Pharmacol Biochem Behav. Oct. 1997;58(2):337–43.

Basu et al. Buprenorphine dependence: a new addiction in India. Disabil Impair. 1990: 3:142–6.

Baumevieille et al. Abuse of prescription medicines in southwestern France. Ann Pharmacother 1997: 31:847–50.

Bedi et al. Abuse Liability of Buprenorphine—A study Among Experienced Drug Users. Indian J Physiol. Pharmacol. 1998;42(1), 95–100.

Benos. [A case of secondary buprenorphine (Temgesic®) dependence] Der Nervenarzt. 1983;54:259–61. [in German w/ English transl].

Biagini et al., Evaluation of cutaneous responses and lung function from exposure to opiate compounds among ethical narcotics–manufacturing workers. J Allergy Clin Immunol. Jan. 1992;89(1 Pt 1):108–18.

Bickel et al. A clinical trial of buprenorphine: comparison with methadone in the detoxification of heroin addicts. Clin Pharmacol Ther. 1988;43:72–8.

Bickel et al. A clinical trial of buprenorphine: 1. Comparison with methadone in the detoxification of heroin addicts. II. Examination of its opioid blocking properties. NIDA Res Monogr. 1987;76:182–8.

Bickel et al. Buprenorphine: dose–related blockade of opioid challenge effects in opioid dependent humans. J Pharmacol Exp Ther. Oct. 1988;247(1):47–53.

Bickel et al. Buprenorphine treatment of opioid dependence: a review. Exp Clin Psychopharmacology 1995; 3:477–89.

Bickel et al. Effects of adding behavioral treatmment to opioid detoxification with buprenorphine. J Consult Clin Psychol. Oct. 1997;65(5):803–10.

Bigelow (w/ Introduction by Blaine). Assessment of buprenorphine in a drug discrimination procedure in humans. Buprenorphine: An alternative Treatment for Opioid Dependence. NIDA Res Monogr. 1992;121:28–37.

Bigelow et al. Abuse liability assessment of buprenorphine–naloxone combinations. NIDA Res Monogr. 1987;76:145–9.

Bigelow. Buprenorphine: Combatting drug abuse with a unique opioid. 1995;(Foreword):xi–xiii.

Bigelow. Human drug abuse liability assessment: opioids and analgesics. Br J Addict. 1991; 86: 1615–23.

Blaine. Introduction. NIDA Res. Monogr. 1992; 1–4.

Budd. High dose buprenorphine for postoperative analgesia. Anaesthesia. Sep. 1981;36(9):900–3.

Bullingham et al. Buprenorphine kinetics. Clin Pharmacol Ther. Nov. 1980;28(5):667–72.

Bullingham et al. Clinical phamacokinetics of narcotic agonist–antagonist drugs. Clin Pharmacokinet. Jul.–Aug. 1983;8(4):332–43.

Bullingham et al. Sublingual buprenorphine used postoperatively: ten hour plasma drug concentration analysis. Br J Clin Pharmacol. May 1982;13(5):665–73.

Buprenorphine is now a controlled drug. Drug Ther Bull. Oct. 16, 1989;27(21):84.

Buprenorphine RTECS Info. In: RTCES Registry No. 52485–79–7. Jan. 13, 2000.

Buprenorphine RTECS Record. In: RTCES Registry No. 52485–79–7. Apr. 25, 2000.

Carl et al. Pain relief after major abdominal surgery: a double–blind controlled comparison of sublingual buprenorphine, intramuscular buprenorphine, and intramuscular meperidine. Anesth Analg. Feb. 1987;66(2): 142–6.

Cervera et al. [Addiction to buprenorphine] Rev Clin Esp 1989;184:159. Letter. [in Spanish w/ English transl].

Cheskin et al. A controlled comparison of buprenorphine and clonidine for acute detoxification from opioids. Drug Alcohol Depend 1994;36:115–21.

Clausen et al. Legal opioid consumption in Denmark 1981–1993. Eur. J Clin Pharmacol. 1995;48(5):321–5.

Cowan et al. Agonist and antagonist properties of buprenorphine, a new antinociceptive agent. Br J Pharmacol. Aug. 1977;60(4):537–45.

Cowan et al. The animal pharmacology of buprenorphine, an oripavine analgesic agent. Br J Pharmacol. Aug. 1977;60(4)547–54.

Cowan. Update on the general pharmacology of buprenorphine. Buprenorphine: Combatting Drug Abuse with a Unique Opioid. 1995;31–47.

D'Arcy. [Drug reactions and interactions after drug reactions and interactions] J Pharm Belg. Sep.–Oct. 1988;43(5):401–4. [in French w/ partial English transl].

Davies et al. Pharmacokinetics of opioids in renal dysfunction. Clin Pharmacokinet. Dec. 1996;31(6):410–22.

Dertwinkel et al. Clinical status of opioid tolerance in long–term therapy of chronic noncancer pain. In: Progress in Pain Research and Management. Opioid Sensitivity of Chronic Noncancer Pain. Kalso et al., eds. 1999; 14:129–41.

Diamant et al. Outpatient opiate detoxification treatment with buprenorphine. Preliminary investigation. Eur Addict Res. 1998;4:198–202.

Dini et al. [Controlled study of the analgesic effect and tolerability of buprenorphine in cancer patients] Minerva Med. Jan. 28, 1986;77(3–4):93–104. [in Italian w/ English abstract].

Dum et al. In vivo receptor binding of the opiate partial agonist, buprenorphine, correlated with its agonistic and antagonistic actions. Br J Pharmacol. Nov. 1981;74(3):627–33.

Eissenberg et al. Buprenorphine's physical dependence potential: antagonist–precipitated withdrawal in humans. J Pharmacol Exp Ther. 1996: 276:449–59.

Eissenberg et al. Controlled opioid withdrawal evaluation during 72 h dose omission in buprenorphine–maintained patients. Drug Alcohol Depend. Apr. 14, 1997;45(1–2):81–91.

Faroqui et al. Buprenorphine, benzodiazepines and respiratory depression. Anaesthesia. Oct. 1983;38(10):1002.

Fincham. Cardiopulmonary arrest and subsequent death after administration of buprenorphine in an elderly female: a case report. J. Geriatric Drug Ther. 1989;3(3):103–5.

Fischer et al. Buprenorphine maintenance in pregnant opiate addicts. Eur Addict Res. 1998;4(Suppl 1):32–6.

Forth. [Another analgesic unmasked as an addictive substance: a vicious circle] MMW Munch Med Wochenschr. Sep. 30, 1983;125(39):834. [in German w/ English transl].

Francaviglia et al. Subarachnoid buprenorphine administered by implantable micropumps. Acta Neurochir (Wien). 1990;102(1–2):62–8.

Franklin et al. Risk assessment in dermatotoxicology. In: Marzulli et al. (Eds.) Dermatotoxicology ($4^{th}$ ed.) 1991. 1991;30:713–47.

Fraser. Clinical toxicology of drugs used in the treatment of opiate dependency. Clinics in Laboratory Medicine. Jun. 1990;10(2):375–86.

Fudala et al. A multi–site efficacy evaluation of a buprenorphine/naloxone product for opiate dependence treatment. NIDA Res Monogr. Problems of Drug Dependent: Proceedings of the 60th annual Scientific Meeting; 1998:105.
Fudala et al. Clinical efficacy studies of buprenorphine for the treatment of opiate dependence. Buprenorphine: Combatting Drug Abuse with a Unique Opioid. 1995: 213–39.
Fudala et al. Outpatient comparison of buprenorphine and methadone maintenance. II. Effects on cocaine usage, retention time in study and missed clinic visits. NIDA Res Monogr. 1991;105:587–8.
Fudala et al. Use of buprenorphine in the treatment of opioid addiction. II.Physiologic and behavioral effects of daily and alternate–day administration and abrupt withdrawal. Clin Pharmacol Ther. 1990; 47:525–34.
Fujimura et al. Influences of bathing and hot weather on the pharmacokinetics of a new transdermal clonidine. M–5041T. J Clin Pharmacol. Oct. 1996;36(10):892–6.
Fullerton et al. Prolonged nauseca and vomiting associated with buprenorphine. Pharmacotherapy 1991;11:90–93.
Gebhart et al. Opiod modulation of visceral pain. In: Progress in Pain Research and Management. Opioid Sensitivity of Chronic Noncancer Pain. Kalso et al., eds. 1999;225–35.
Gould. Buprenorphine causes pulmonary edema just like all othr mu–opioid narcotics. Upper airway obstruction, negative alveolar pressure. Chest. May 1995;107(5):1478.
Gourlay. Different opioids—same actions? In: Progress in Pain Research and Management. Opioid Sensitivity of Chronic Noncancer Pain. Kalso et al., eds. 1999; 14:97–115.
Grond et al. Clinical pharmacokinetics of transdermal opioids: focus on transdermal fentanyl. Clin Pharmacokinet. Jan. 2000;38(1):59–89.
Guilbaud et al. Antinociceptive effect of opioid substances in different models of inflammatory pain. In: Progress in Pain Research and Management. Opioid Sensitivity of Chronic Noncancer Pain. Kalso et al., eds. 1999; 14:201–23.
Hand et al. Buprenorphine disposition in patients with renal impairment: single and continuous dosing, with special reference to metabolites. Br J Anaesth. Mar. 1990;64(3):276–82.
Hand et al. Radioimmunoassay of buprenorphine in urine: studies in patients and in a drug clinic. J Anal Toxicol. Mar.–Apr. 1989;13(2):100–4.
Heel et al. Buprenorphine: a review of its pharmacological properties and therapeutic efficacy. Drugs. 1979;17:81–110.
Henrion. [Assessment of the effectiveness of measures taken in France to reduce the risk of intravenous heroin addiction] Bull Acad Natl Med. Jun–Jul. 1997; 181(6):1177–85; discussion 1186–9. [in French w/ English transl].
Hernandez–Mora et al. [Paroxysmal atrial fibrillation after ingestionof buprenorphine.] Rev Clin Esp. Jun. 1988;183(2):99–100. [in Spainish w/ English transl].
Hirschauer et al. [Is buprenorphine hepatotoxic?] Gastroenterol Clin Biol. Jun. 1989;13(6–7):636. [in French w/ English transl].
Holdsworth et al. Transdermal fentanyl disposition in elderly subjects. Gerontology. 1994;40(1):32–7.
Holmes. Buprenorphine side effects. N Z Med J. Mar. 14, 1984;97(751):166.
Hoskin et al. Opioid agonist–antagonist drugs in acute and chronic pain states. Drugs 1991;41:326–44.
Huguet–Levet. [Buprenorphine: its ambiguity] Ann Pharm Fr. 1995;53(3):124–30. [in French w/ English transl].
Jamison. Comprehensive pretreatment and outcome assessment for chronic opioid therapy in nonmalignant pain. J Pain Symptom Manage. Apr. 1996;11(4):231–41.
Jasinski et al. Abuse liability assessment in human subjects. Trends Pharmacol Sci. 1984;5:196–200.
Jasinski et al. Human pharmacology and abuse potential of the analgesic buprenorphine: a potential agent for treating narcotic addiction. Arch Gen Psychiatry. 1978:35:501–16.
Jasinski et al. Laboratory studies of buprenorphine in opioid abusers. In: Cowan A, Lewis J W, eds. Buprenorphine: combatting drug abuse with a unique opioid. New York: Wiley–Liss. 1995:189–211.
Jasinski et al. Progress report from the NIDA Addiction Research Center, Baltimore, Maryland. NIDA Res Monogr. Mar. 1984;49:69–76.
Jasinski et al. Progress report of the NIDA Addiction Research Center. NIDA Res Monogr. 1982;41:45–52.
Jasinski et al. Progress report of the NIDA Addiction Research Center. Baltimore, Maryland, 1982. NIDA Res Monogr. Apr. 1983;43:92–8.
Jasinski et al. Sublingual versus subcutaneous buprenorphine in opiate abusers. Clin Pharmacol Ther. 1989;45:513–9.
Johnson et al. A controlled trial of buprenorphine treatment for opioid dependence. JAMA. 1992;267:2750–5.
Kalso. Route of opioid administration—does it make a difference ? In: Progress in Pain Research and Management. Opioid Sensitivity of Chronic Noncancer Pain. Kalso et al., eds. 1999; 14:117–28.
Kareti et al. Effects of buprenorphine, a new narcotic agonist–antagonist analgesic on the EEG, power spectrum and behavior of the rat. Neuropharmacology. Feb. 1980;19(2):195–201.
Keup et al. [Potential for buprenorphine abuse] MMW Munch Med Wochenschr. Sep. 30, 1983:125(39):835–7. [in German w/ English transl].
Keup. [Buprenorphine (Temgesic®) abuse and dependence] Suchtgefahren. 1983;29:193–4. [in German w/ English transl].
Lange et al. Safety and side–effects of buprenorphine in the clinical management of heroin addiction. Drug Alcohol Depend. Aug. 1990;26(1):19–28.
Law et al. The feasibility of abrupt methadone–buprenorphine transfer in Bitish opiate addicts in an outpatient setting. Addition Bio. 1997;2:191–200.
Leander. Buprenorphine has potent kappa opioid receptor antagonist activity. Neuropharmacol. 1987;26:1445–7.
Leander. Buprenorphine is a potent kappa–opioid receptor antagonist in pigeons and mice. Eur J Pharmacol. Jul. 14, 1988;151(3):457–61.
Lewis et al. Buprenorphine—background to its development as a treatment for opiate dependence. NIDA Res Monogr. 1992;121:5–11.
Lewis. Buprenorphine. Drug Alcohol Depend. 1985. 14:363–72.
Lewis. Clinical pharmacology of buprenorphine in relation to its use as an analgesic. Buprenorphine: Combatting Drug Abuse with a Unique Opioid. 1995;151–63.
Lewis et al. The Pharmacology and abuse potential of buprenorphine: a new antagonist analgesic. Advances in substance abuse 1983;3:103–54.
Ling et al. A controlled trial comparing buprenorphine and methadone maintenance in opioid dependence. Arch Gen Psychiatry. May 1996;53(5):401–7.

Ling et al. Buprenorphine maintenance treatment of opiate dependence, a multicenter, randomized clinical trial. Addiction. 1998;93:475–86.

Ling et al. Methadyl acetate and methadone as maintenance treatments for heroin addicts. A veterans administration cooperative study. Arch Gen Psychiatry. Jun. 1976;33(6):709–20.

Ling et al. Substitution pharmacotherapies for opioid addiction: from methadone to LAAM and buprenorphine. J Psychoactive Drugs. Apr.–Jun. 1994;26(2):119–28.

Litchfield. Buprenorphine in oral surgery. A comparison with fentanyl. SAAD Dig. Oct. 1986;6(8):182–6.

Liu et al. Rapid detoxification of heroin dependence by buprenorphine. Acta Pharmacol Sin. 1997;18:112–4.

Lizasoain et al. Buprenorphine: bell–shaped dose–response curve for its antagonist effects. Gen Pharmacol. 1991;22(2):297–300.

Lloyd–Jones et al. Plasma concentration and disposition of buprenorphine after intravenous and intramuscular doses to baboons. Eur J Drug Metab Pharmacokinet. 1980;5(4):233–9.

Macdonald et al. Psychomotor effects of ketorolac in comparison with buprenorphine and diclofenac. Br J Clin Pharmacol. 1989;27:453–9.

Mackenzie et al. Influence of pretreatment with a monoamine oxidese inhibitor (Phenelzine) on the effects of buprenorphine and pethidine in the conscious rabbit. Br J Anaesth. 1988;60:216–21.

Marquet et al. Buprenorphine withdrawal syndrome in a newborn. Clin Pharmacol Ther. 1997;62:569–71.

Marquet et al. [In utero exposure to Subutex induces no or mild withdrawal syndromes in the newborn] Therapie. 1998;53:178. [in German w/ English abstract].

Martin. History and development of mixed opioid agonist, partial agonist and antagonists. Br J Clin Pharmacol. 1979;7:273S–9S.

Martin et al. The effects of morphine–and nalorphine–like drugs in the nondependent and morphine–dependent chronic spinal dog. J Pharmacol Exp Ther. 1976;197:517–32.

Max et al. Single–dose analgesic comparisons. Advances in pain research and therapy. 1991;18:55–95.

McQuay et al. Buprenorphine kinetics. Advances in Pain Res and Ther. 1986. 8:271–83.

McQuay et al. Buprenorphine kinetics in humans. In: Buprenorphine: Combatting Drug Abuse with a Unique Opioid. 1995;137–47.

McQuay et al. Clinical effects of buprenorphine during and after operation. Br J Anaesth. Oct. 1980;52(10):1013–9.

McQuay et al. Delayed respiratory depression. A case report and a new hypothesis. Acta Anaesthesiol Belg. 1979;30 Suppl:245–7.

Mello et al. Behavioral pharmacology of buprenorphine. Drug Alcohol Depend. Feb. 1985;14(3–4):283–303.

Mello et al. Buprenorphine effects on human heroin self–administration: an operant analysis. J Pharmacol Exp Ther. 1982:223:30–9.

Mello et al. Buprenorphine self–administration by rhesus monkey. Pharmacol Biochem Behav. 1981;15:215–25.

Mello et al. Buprenorphine suppresses cocaine self–administration by rhesus monkeys. Science. 1989;245:859–62.

Mello et al. Buprenorphine suppresses heroin use by heroin addicts. Science. 1980;207:657–9.

Mello et al. Buprenorphine's effects on cocaine self–administration: preclinical studies. In: Buprenorphine Combatting Drug Abuse With A Unique Opioid. 1995;249–50.

Mendelson et al. Bioavailability of sublingual buprenorphine. J Clin Pharmacol. 1997;37:31–7.

Mendelson et al. Buprenorphine and naloxone interactions in methadone maintenance patients. Biol Psychiatry. 1997;41:1095–101.

Mendelson et al. Buprenorphine attenuates the effects of cocaine on adrenocorticotropin (ACTH) secretion and mood states in man. Neuropsychopharmacology. 1992;7:157–62.

Mendelson et al. Buprenorphine and naloxone interactions in opiate–dependent volunteers. Clin Pharmacol Ther. Jul. 1996;60(1):105–14.

Mendelson et al. Human laboratory studies of buprenorphine. NIDA Res Monogr. 1992;121:38–60.

Mitaka et al. Comparison of hemodynamic effects of morphine, butorphanol, buprenorphine and pentazocine on ICU patients. Bull Tokyo Med Dent Univ. Jun. 1985;32(2):31–9.

Moa et al. Sublingual buprenorphine as postoperative analgesic: a double–blind comparison with pethidine. Acta Anaesthesiol Scand. 1990;34:68–71.

Mok et al. Multidose/observational, comparative clinical analgetic evaluation of buprenorphine. J Clin Pharmacol. Jul. 1981;21(7):323–9.

Moore et al. Reversal of postoperative hyperglycaernia by buprenorphine. Lancet. Sep. 13, 1980;2(8194):597–8.

Morrison. Psychoactive substance use and related behaviours of 135 regular illicit drug users in Scotland. Drug Alcohol Depend. 1989;23:95–101.

Mukhtar et al. Cutaneous cytochrome P–450. Drug. Metabolism Revs. 1989;20(204):657–73.

Mukhtar et al. Cytochrome P–450 dependent metabolism of testosterone in rat skin. Biochem Biophys Res Commun. Jun. 15, 1987;145(2):749–53.

Nasar et al. An open study of sub–lingual buprenorphine in the treatment of chronic pain in the elderly. Curr Med Res Opin. 1986;10(4):251–5.

Nigam et al. Buprenorphine in opiate withdrawal: a comparison with clonidine. J Subst Abuse Treat. Jul.–Aug. 1993;10(4):391–4.

Nizamie et al. Buprenorphine abuse: a case report. Indian J Psychiatry. 1990;32:198–200.

O'Brien. Drug adiction and abuse. In: Goodman & Gilman's The Pharmacological Basis of Therapeutics. $9^{th}$ ed. 1996;Chp. 24:557–577.

O'Connor et al. Buprenorphine abuse among opiate addicts Brit J Addict. 1988; 83:1085–7.

O'Connor et al. Rapid and ultrarapid detoxification techniques. JAMA 1998;279:229–34.

O'Connor et al. Three methods of opioid detoxification in a primary care setting: a randomized trial. Ann Intern Med. 1997;127:526–30.

O'Neill. The cognitive and psychomotor effects of opioid drugs in cancer pain management. Cancer Surv. 1994;21:67–84.

Obel et al. Buprenorphine–supplemented anaesthesia. Influence of dose on duration of analgesia after cholecystectomy. Br J Anaesth. Mar. 1985;57(3):271–4.

Ohtani et al. Kinetics of respiratory depression in rats induced by buprenorphine and its metabolite, norbuprenorphine, J Pharmacol Exp Ther. Apr. 1997;28(1):428–33.

Olley et al. Plasma levels of opioid material in man following sublingual and intravenous administration of buprenorphine: exogenous/endogenous opioid interaction? J Pharm Pharmacol. 1988;40:666–7.
Opioid agonist–antagonist analgesics. In: WHO Expert Committee on Drug Dependence. 25th Report, Geneva: World Health Oarganization Technical Report Series; 1989:775 16–24.
Orwin et al. A double blind comparision of buprenorphine and morphine in conscious subjects following administration by the intramuscular route. Acta Anaesthesiol Belg. 1976;27:171–81.
Orwin. Pharmacological aspects in man. Pain:vNew Perspect. Meas. Manage. (Symp) 1977:141–59.
Ouellette et al. Comparison of buprenorphine and morphine: a multicenter, multidose study in patients with severe postoperative pain. Contemp. Surg. 1986; 28:55,57–59,62–64.
Ouellette. Buprenorphine and morphine efficacy in postoperative pain: a double–blind multiple–dose study. J Clin Pharmacol. Apr. 1982;22(4):165–72.
Ouellette. Comparison of analgesic activity of buprenorphine hydrochloride and morphine in patients with moderate to severe pain postoperatively. Surg Gynecol.Obstet. Sep. 1984;159(3):201–6.
Overweg—Van Kintz et al. [Failing pain suppression during sublingual use of buprenorphine] Ned Tijdschr Geneeskd. 1987;131(44)1973–4. [in Dutch w/ English transl].
Parran et al. A buprenorphine stabilization and rapid–taper protocol for the detoxification of opioid dependent patients. Am J Addict. 1994;3:306–13.
Pathre et al. Generalised seizure following sublingual buprenorphine. J Assoc Physicians India. Apr. 1994;42(4):327–8.
Pausawasdi et al. A comparison of buprenorphine and morphine for immediate postoperative pain relief in Thai patients. J Med Assoc Thai. May 1984;67(5):284–9.
Pechnick et al. The effects of the acute administration of buprenorphine hydrochloride on the release of anterior pituitary hormones in the rat: evidence for the involvement of multiple opiate receptors. Life Sci. Nov. 18, 1985;37(20):1861–8.
Pedersen et al. Peroperative bupronorphine: do high dosages shorten analgesia postoperatively? Acta Anaesthesiol Scand. Nov. 1986;30(8):660–3.
Petti. Postoperative pain relief with pentazocine and acetaminophen: comparison with other analgesic combinations and placebo. Clin Ther. 1985;8(1):126–33.
Ponsoda et al. The effects of buprenorphine on the metabolism of human hepatocytes. Toxic. In vitro. 1991;5(3):219–24.
Pontani et al. Disposition in the rat of buprenorphine administered parenterally and as a subcutaneous implant. Xenobiotica. Apr. 1985;15(4):287–97.
Preston et al. Abuse liability studies of opioid agonist–antagonists in humans. Drug Alcohol Depend. 1991;28:49–82.
Preston et al. Abuse potential and pharmacological comparison of tramadol and morphine. Drug Alcohol Depend. Jan. 1991;27(1):7–17.
Preston et al. Diazepam and methadone interactions in methadone maintenance. Clin Pharmacol Ther. Oct. 1984;36(4):534–41.
Preston et al. Discrimination of agonist–antagonist opioids in humans trained on two–choice saline–hydromorphone discrimination. J Pharmacol Exp Ther. 1992;261:62–71.
Preston et al. Drug discrimination assessment of agonist–antagonist opioids in humans: a three–choice saline–hydromorphone–butorphanol procedure. J Pharmacol Exp Ther. 1994;271:48–60.
Preston et al. Drug discrimination in human postaddicts: agonist–antagonist opioids. J Pharmacol Exp Ther. 1989;250:184–96.
Preston et al. Effects of sublingually given naloxone in opioid–dependent human volunteers. Drug Alcohol Depend. 1990;25:27–34.
Price et al. A psychophysical analysis of experimential factors that selectively influence the affective dimension of pain. Pain. Apr. 1980;8(2):137–49.
Quigley et al. A case of buprenorphine abuse. Med J Aust. 1984; 140:425–6.
Rainey. Abuse of buprenorphine. N Z Med J. 1986; 99:72.
Regini et al. [Buprenophine withdrawal syndrome in a neonate. Which treatment?] Ped Med Chir. 1998; 20:67–9. [in Italian with English transl].
Reisine et al. Opioid analgesics and antagonists. In: Molinoff PB, Ruddon RW, Gilman AG, editors. Goodman and Gilman's The pharmacological basis of therapeutics. 9th ed. 1996; Chp. 23:521–55.
Reisinger. [Value of comparing buprenorphine with methadone] Ann Med Interne (Paris). Nov. 1994;145 Suppl 3:23–5. [in French w/ English transl].
Reisinger. Buprenorphine as new treatment for heroin dependence. Drug Alcohol Depend. Dec. 1985;16(3):257–62.
Reisinger. Results from experience with buprenorphine replacement in outpatients in Belgium. Ann. Med. Interne. 1994;145(Supp.3):46–47.
Reisinger. Treatment of four pregnant heroin addicts with buprenorphine: history and outcome. NIDA Res Monogr 1995;162–261.
Report of the commission on the evaluation of pain. In: Soc. Security Bull. 1986.
Reynaud et al. Six deaths linked to concomitant use of buprenorphine and benzodiazepines. Addiction 1998;93:1385–92.
Richard et al. [Virtiginous syndrome: side effect of buprenorphine?] Cah Anesthesiol. 1988; 36:641–2. [in French with English transl].
Richert et al. [Drug dependence on buprenorphine] MMW Munch Med Wochenschr 1983; 125:1195–8. [in German w/ English transl].
Risbo et al. Sublingual buprenorphine for premedication and postoperative pain relief in orthopaedic surgery. Acta Anaesthesiol Scand. Feb. 1985;29(2):180–2.
Robbie. A trial of sublingual buprenorphine in cancer pain. Br J Clin Pharmacol. 1979;7 Suppl 3:315S–317S.
Robertson et al. Buprenorphine: dangerous drug or overlooked therapy? Br Med J. 1986:292–1465.
Robinson et al. The misuse of buprenorphine and a buprenorphine–naloxone combination in Wellington. new Zealand. Drug Alcohol Depend. 1993; 33:81–6.
Rolandi et al. Changes in pituitary secretion induced by an agonist–antagonist opioid drug. Acta Endocrinol (Copenh). Nov. 1983;104(3):257–60.
Rosen et al. Buprenorphine: duration of blockade of effects of intramuscular hydromorphine. Drug Alcohol Depend. 1994;35:141–9.

Rosen et al. Effects of acute buprenorphine on responses to intranasal cocaine: a pilot study. Am J Drug Alcohol Abuse. 1993;19:451–64.

Rosenfeldt et al. Haemodynamc effects of buprenorphine after heart surgery. Br Med J. Dec. 9, 1978;2(6152):1602–3.

Rothman et al. Buprenorphine: a review of the binding literature. In: Buprenorphine: Combatting Drug Abuse with a Unique Opioid. 1995;19–29.

Saarialho–Kere et al. Psychomotor, respiratory, and neuroendocrinological effects of buprenorphine and amitriptyline in healthy volunteers. Eur J Clin Pharmacol. 1987; 33:139–46.

Sakol et al. Buprenorphine and temazepam abuse by drug takers in Glasgow—an increase. Brit J Addict. 1989;84:439–41.

San et al. [Prevalence of buprenorphine consumption in heroin addicts undergoing treatment] Med Clin (Barc). 1989; 93:645–8. [in Spanish w/ English transl].

San et al. Assessment and management of opioid withdrawal symptoms in buprenorphine–dependent subjects. Br J Addict. Jan. 1992;87(1):55–62.

San et al. Consumption of buprenorphine and other drugs among heroin addicts under ambulatory treatment: results from cross–sectional studies in 1988 and 1990. Addiction. 1993; 88:1341–9.

San Molina et al. [Addiction to buprebnorphine] Rev Clin Esp. 1987;181:288–9. [in Spanish w/ English transl].

Schmidt et al. Postoperative pain relief with naloxone. Severe respiratory depression and pain after high dose buprenorphine. Anaesthesia. 1985;40:583–6.

Schottenfeld et al. Buprenorphine vs. methadone maintenance treatment for concurrent opioid dependence and cocaine abuse. Arch Gen Psychiatry. 1997;54:713–20.

Schuh et al. Buprenorphine, morphine, and naloxone effects during ascending morphine maintenance in humans. J Pharmacol Exp Ther. 1996; 278:836–46.

Sear et al. Buprenorphine for postoperative analgesia. Br J Anaesth. Jan. 1979;51(1):71.

Segal et al. Buprenorphine: what interests the national institute on drug abuse? Buprenorphine: In: Combatting Drug Abuse with a Unique Opioid. 1995;309–20.

Segui et al. [Buprenorphine comsumption, an indicator of poor prognosis in the course of drug dependencies] Actas Luso Esp Neurol Psiquiatr Cienc Afines. Jan.–Feb. 1992;20(1):17–22. [in Spanish w/ English transl].

Segui et al. [Data regarding buprenorphine consumption by drug–addicted individuals] Rev Clin Esp. 1989; 185:271–2. [in Spanish with English transl].

Segui et al. [Prevalence of buprenorphine consumption in a sample of outpatient drug abusers] Rev Clin Esp. Jun. 1991;189(1):14–7. [in Spanish w/ English transl].

Segui et al. [Subgroups of addicted buprenorphine–consuming patients] An Med Interna. Jan. 1991;8(1):18–22. [in Spanish w/ English transl].

Sekar et al. Buprenorphine, benzodiazepines and prolonged respiratory depression. Anaesthesia. 1987;42:567–8.

Seow et al. Buprenorphine: a new maintenance opiate? Med J Aust. Apr. 14, 1986; 144(8):407–11.

Sganzerla et al. Analgesia and hemodynamic effects of buprenorphine in acute infarction of the heart, Jpn Heart J. Jan. 1987;28(1):63–71.

Shannon et al. Morphine–like discriminative stimulus effects of buprenorphine and demethoxbuprenorphine in rats: quantitative antagonism by naloxone. J Pharmacol Exp Ther. 1984; 229:768–74.

Shuster. Fluoroquinolones and tendon rupture or tendinitis. Buprenorphine–induced hypertension and tachycardia: rare but serious. Hospital Pharmacy. 1996;31(1)41–2.

Singh et al. Cases of buprenorphine abuse in India. Acta Psychiatr Scand. 1992;86:46–8.

Sjovall. Use of midazolam and buprenorphine in combination anaesthesia. Ann Clin Res. Aug. 1983;15(4):151–5.

Spitzer et al. Scientific approach to the assessment and management of activity–related spinal disorders. Spine. 1987;12(7):S9–S59.

Staritz. Pharmacology of the sphineter of Oddi. Endoscopy. Aug. 1988;20 Suppl 1:171–4.

Stellato et al. Human basophil/mast cell releasability. IX. Heterogeneity of the effects of opioids on mediator release. Anesthesiology. Nov. 1992;77(5):932–40.

Stewart. Effect of scheduling of buprenorphine (Temgesic) on drug abuse pattern in Glasgow. BMJ. Apr. 20, 1991;302(6782):969.

Stinchcomb et al. Permeation of buprenorphine and its 3–alkyl–ester prodrugs through human skin. Pharm Res. Oct. 1996;13(10):1519–23.

Strain et al. Acute effects of buprenorphine, hydromorphone, and naloxone in mathadone–maintained volunteers. J Pharmacol Exp Ther. 1992:261:985–93..

Strain et al. Buprenorphine effects in methadone–maintained volunteers: effects at two hours after methadone. J Pharmacol Exp Ther. 1995;272:628–38.

Strain et al. Comparison of buprenorphine and methadone in the treatment of opioid dependence. Am J Psychiatry. 1994;151:1025–30.

Strain et al. The effects of buprenorphine in buprenorphine–maintained volunteers. Psychopharmacol. 1997;129:329–38.

Strang. Abuse of buprenorphine (Temgesic) by snorting. BMJ. Apr. 20, 1991; 302(6782):969.

Strang. Abuse of buprenorphine. Lancet. Sep. 28, 1985;2(8457):725.

Streisand. Transdermal–mucosal sedative and analgesic delivery. West. J Med. 1990;153:310.

Su. Further demonstration of κ opioid binding sites in the brain: evidence of heterogeneity. J Pharmacol Exp. Ther. 1985;232:144–8.

Summerfield et al. Buprenorphine in end stage renal failure. Anaesthesia. Sep. 1985;40(9):914.

Swain et al. Primary addiction study. UM952. In: Minutes of the Committee on Problems of Drug Dependence. Washington (DC), National Academy of Sciences, National Research Council. 1975;791.

Tallarida et al. Theory and statistics of detecting synergism between two active drugs: cocaine and buprenorphine. Psychopharmacology (Berl). Oct. 1997;133(4):378–82.

Tantucci et al. Acute respiratory effects of sublingual buprenorphine: comparison with intramuscular morphine. Int J Clin Pharmacol Ther Toxicol. Jun. 1992;30(6):202–7.

Tebbett. Analysis of buprenorphine by high–performance liquid chromatography. J Chromatogr. Nov. 22, 1985;347(3):411–3.

Teoh et al. Acute interactions of buprenorphine with intravenous cocaine and morphine: an investigational new drug phase 1 safety evaluation. Clin Psychopharmacol. 1993;13:87–99.*

Teoh et al. Buprenorphine effects on morphine–and cocaine–induced subjective responses by drug–dependent men. J Clin Psychopharmacol. Feb. 1994;14(1):15–27.*

Thammakumpee et al. Noncardiogenic pulmonary edema induced by sublingual buprenorphine. Chest. Jul. 1994;106(1):306–8.*

Tharp et al. Functional hetergeneity of human mast cells from different anatomic sites: in vitro responses to morphine sulfate. J Allergy Clin Immunol. Apr. 1987;79(4):646–53.*

Thorn et al. Prolonged respiratory depression caused by sublingual buprenorphine. Lancet. Jan. 23, 1988;1(8578):179–80.*

Tigerstedt et al. Double–blind, multiple–dose comparison of buprenorphine and morphine in postoperative pain. Acta Anaesthesiol Scand. Dec. 1980;24(6):462–8.*

Touzeau et al. Benzodiazepines and methadone: a dangerous combination?] Ann Med Interne (Paris). Nov. 1994;145 Suppl 3:19–22. [in French w/ English transl].*

Tracqui et al. [Prison, drugs and death: two deaths due to overdoses in a prison environment] J Med Leg Droit Med. 1998a;41:185–92. [in French w/ English transl].*

Tracqui et al. Buprenorphine–related deaths among drug addicts in France: a report on 20 fatalities. J Anal Toxicol. 1998c;22:430–4.*

Uehlinger et al. Comparison of buprenorphine and methadone in the treatment of opioid dependence. Swiss multicentre study. Eur Addict Res. 1998;4 Suppl 1:13–8.*

Umbricht et al. Safety of bruprenorphine: ceiling for cardio–respiratory effects at high IV doses. NIDA Res Monogr. 1998; 179:225.*

Van Loveren et al. Assessment of immunotoxicity of buprenorphine. Lab Anim. Oct. 1994;28(4):355–63.*

Vanakoski et al. Exposure to high ambient temperature increases absorption and plasma concentrations of transdermal nicotine. Clin Pharmacol Ther. Sep. 1996;60(3):308–15.*

Varey. The safety of buprenorphine (Temgesic). N Z Med J. Jan. 24, 1990;103(882):24.*

Vargas et al. Buprenorphine: a case of abuse [letter] [in Spanish]. An Med Interna. 1987; 4:366.*

Ventafridda et al. Chronic analgesic study on buprenorphine action in cancer pain. Comparison with pentazocine, Arzneimittelforschung. 1983;33(4):587–90.*

Vignau. Preliminary assessment of a 10–day rapid detoxification programme using high dosage buprenorphine. Eur. Addict Res 1998; 4 Suppl. 1:29–31.*

Villiger. Binding of buprenorphine to opiate receptors. Regulation by guanyl nucleotides and metal ions. Neuropharmacology. Mar. 1984;23(3):373–5.*

Vocci. Basis for the recommendation for rescheduling of buprenorphine into Schedule IV of the Controlled Substances Act. FDA Document 2726A; Jul. 31, 1980;1–8.*

Waal. Buprenorphine (Temgesic)—new agent of abuse. Tidsskr Nor Laegeforen 1989; 109:1326–7. [in Norwegian w/ English transl].*

Walsh et al. Clinical pharmacology of buprenorphine: ceiling effects at high doses. Clin Pharmacol Ther. 1994;55:569–80.*

Walsh et al. The acute effects of high dose buprenorphine in non–dependent humans. NIDA Res. Monogr. 1992;119:245.*

Walter et al. Absorption, distribution, metabolism, and excretion of buprenorphine in animals and humans. In: Buprenorphine: Combatting Drug Abuse with a Unique Opiod. 1995;13–35.*

Walter et al. Preclinical evaluation of buprenorphine. Research and Clinical Forums. 1997;19(2):17–23.*

Wang et al. The study of anagesics following single and repeated doses. J Clin Pharmacol. Feb.–Mar. 1981;21(2):121–5.*

Watanabe et al. Rectal absorption and mucosal irritation of rectal gels containing buprenorphine hydrochloride prepared with water–soluble dietary fibers, xanthan gum and locust bean gum. J Controlled Release. 1996;38:29–37.*

Weinberg et al. Sublingual absorption of selected opioid analgesics. Clin Pharmacol Ther. 1988;44:335–42.*

Wiesenfeld–Hallin et al. Opioid sensitivity in antinociception: Role of anti–opioid systems with emphasis on cholecystokinin and NMDA receptors. In: Progress in Pain Research and Management. Opioid Sensitivity of Chronic Noncancer Pain. Kalso et al., eds. 1999; 14:237–52.*

Woods et al. Behavioral pharmacology of buprenorphine: issues relevant to its potential in treating drug abuse. NIDA Res Monogr. 1992;121:12–27.*

Wright et al. Acute physical dependence in humans: repeated naloxone–precipitated withdrawal after a single dose of methadone. Drug Alcohol Depend. 1991; 27:139–48.*

Yanagita et al. Dependence potential of buprenorphine studied in rhesus monkeys. NIDA Res Monogr. 1982;41:208–14.*

Zacny et al. Comparing the subjective, psychomotor and physiological effects of intravenous buprenorphine and morphine in healthy volunteers. J Pharmacol Exp Ther. 1997;282:1187–97.*

Zacny et al. A review of the effects of opioids on psychomotor and cognitive functioning in humans. Experimental and Clin. Psychopharmacol. 1995:3(4):432–66.*

Zola et al. Comparative effects and analgesic efficacy of the agonist–antagonist opioids. Drug Intell Clin Pharm. Jun. 1983;17(6):411–7.

7.2. Buprenorphine, MNH/PAD/87.11, pp. 29–63 (undated).

A review of data for the scientific community in preparation for the WHO 2002 critical review of buprenorphine: Scientific, medical and policy support for the continuing control of Buprenorphine in Schedule III of the 1971 Convention on Psychotropic Substance. Dec. 13, 2001 (30 pp.).

Addendum to a review of data for the scientific community in preparation for the WHO 2002 critical review of buprenorphine: Data on reactions possibly related to abuse of Buprenorphine reported to the WHO collaborating centre for international drug monitoring. Uppsala Sweden and Data on seizures from the NFLIS. Feb. 26, 2002 (11 pp.).

Agar et al., Buprenorphine: "field trials" of a new drug. Qual Health Res. Jan. 2001;11(1):69–84.

Annual report on the state of the drugs problem in the European Union by EMCDDA. 1999 (33pp.).

Auriacombe et al., Buprenorphine prescribed by general practitoners—A safe means of increasing patient access to treatment?, in Maintenance Treatment in Heroin Addiction—Evidence at the Crossroads (Wall and Haga, eds.), 2003 (5 pp.).

Bailey et al. Package inserts and other dosage guidelines are especially useful with new analgesic and new analgesic delivery systems. Anesth Analg. Dec. 1992;75(6):873–5.
Bégaud et al., of the Joint Ministerial Mission for Combatting Drugs and Drug Addiction Information Office, Evaluation of Subutex® availability in the treatment of drug users. Summary review of the literature and available data and proposals for a research program. Jun. 1998 (83 pp.).
Brown, Jr., of American Society of American Society of Addiction Medicine, letter to DEA Administrator dated May 17, 2002 in response to notice published in the Federal Register of Mar. 21, 2002.
BTDS List of Studies (undated).
BTDS Outstanding Issues—A waiting FDA response from Oct. 2, 1999–Mar. 20, 2000.
BTDS Planned FDA Submissions/Interactions for 2000.
Buprenorphine DEA Review DocumentsScheduling under the CSA. Feb. 2002 (26 pp.).
Buprenorphine prescription withdrawn in Norway, available at http://www.drugscope.org.uk.
Buprenorphine TDS Pre–NDA Meeting, Flux rate analysis of Buprenorphine transdermal delivery systems (BTDS) (undated).
Buprenorphine transdermal system (IND 50,273) meeting minutes dated Jan. 23, 1997.
Buprenorphine transdermal system (IND 50,273) meeting minutes of Jul. 14, 1999 (8 pp.).
Buprenorphine transdermal system (IND 50,273) meeting minutes of May 16, 1996.
Buprenorphine transdermal system (IND 50,273) meeting minutes of Nov. 18, 1998.
Buprenorphine transdermal system (IND 50,273) nonclinical video conference of Feb. 24, 1997 (4 pp.).
Bushnell et al., Choosing the right analgesic. A guide to selection. Drugs. Sep. 1993;46(3):394–408.
Caplan et al., Transdermal fentanyl: An overview of clinical progress in Opioids in Anesthesia II (Estafanous, ed.), 1991(21):267–73.
Chapters 17 and 18 discussion in opioids in Anesthesia II (Estafanous, ed.)1991:223–38.
Charuvastra et al., Buprenorphine versus placebo taste test. CPDD 1994 Annual Scientific Meeting Abstract.
Clarification of pharmtox requirements for NDA (IND 50,273) meeting minutes with sponsor of Apr. 13, 1999.
Clinical chronology for BTDS NDA from May 10, 1996–Feb. 4, 2000.
CMC Chronology for BTDS NDA from Jun. 26, 1997–Mar. 2, 2000.
Cinical documentation (Part IV), vols. 6–37 Table of Contents from Grünethal GmbH as of Dec. 13, 1999.
Comparison of the analgesic efficacy and safety of buprenorphine in the form of a sublingual tablet and a transdermal therapeutic system (TTS 50) in chronic pain, Grunenthal; GmbH—Medical Department, Germany, Report No. WIS–BUP 03, May 20, 1999.
Compton et al., What dose of buprenorphine reduces opiate use? A double–blind dose–ranging study. CPDD 1994 Annual Scientific Meeting Abstracts.
Controlled Substance Staff—Background material for peripheral and central nervous system advisory committee. Risk management plans for recently approved drugs. Mar. 15, 2001.
Coop et al., Ring constrained analogs of Buprenorphine. CPDD 1994 Annual Scientific Meeting Abstract.
Determination of the absolute bioavailability of buprenorphine from a transdermal therapeutic system with 2 different loadings (20 and 40 mg) in comparison to an intravenous administration in an open 3–way crossovere trial with 24 healthy male volunteers. Gruenenthal GmbH—Research Centre, Germany. Report No. FO–PK 391, May 6, 1996.
Determination of the analgesic efficacy of three buprenorphine dosages versus placebo in a transdermal therapeutic system (TTS) in patients with tumour pain and patients with chronic pain of non–tumour–related origin. Gruenenthal GmbH—Medical Department, Germany. Report No. WIS–BUP 01, Jun. 17, 1999.
Determination of the analgesic efficacy of three buprenorphine dosages versus placebo in a transdermal therapeutic system (TTS) in patients with tumour pain and patients with chronic non–tumour–related pain. Gruenenthal GmbH—Medical Department, Germany. Report No. WIS–BUP 02, Jun. 1, 1999.
Determination of the pharmacokinetic parameters of buprenorphine from a transdermal therapeutic system with 3 different loadings (20, 30, and 40 mg) in an open, balanced 3–parallel group study in 54 healthy volunteers. Chrysalis Clin. Pharmcol Services GmbH, Germany. Final Report PK 402 Integrated PK, Jun. 30, 1997.
Determination of the plasma concentration of buprenorphine from a transdermal therapeutic system with three different loadings in a patient population. Gruenenthal GmbH—Research Centre, Germany. Report No. WIS–BUP 02 PK, Jan. 20, 1999.
Follow–up treatment with buprenorphine TTS 50 after completion of the double–blind phase of studies. Gruenenthal GmbH—Medical Department, Germany. Report No. WIS–BUP FU, May 25, 1999.
Fukaze et al., Precipitation of morphine withdrawal by buprenorphine and butorphanol in male cynomolgus monkeys. CPDD 1994 Annual Scientific Meeting Abstracts.
Gasfriend et al., Long–term effects of buprenorphine for treatment of combined opiate and cocaine dependence. CPDD 1994 Annual Scientific Meeting Abstracts.
Guo et al., Bioadhesive buccal polymer patches for buprenorphine controlled delivery: Solubility consideration. Proceed Intern Symp Control Rel Bioact Mater. 1995.
Hawks et al., Buprenorphine–naloxone combination drug for the treatment of drug addiction. CPDD 1994 Annual Scientific Meeting Abstracts.
Hayes, of FDA, Comments dated Mar. 31, 1997 regarding buprenorphine patch (IND 50,273), Mar. 31, 1997 (2 pp.).
Hogan & Hartson's supplemental filing dated Apr. 10, 2002 in support of citizen petition filed on Dec. 11, 2001.
Hogan & Hartson's response dated May 9, 2002 to 67 FR 17074 of Apr. 9, 2002.
Hogan & Hartson's comments dated May 22, 2002 to 67 FR 13114 of Mar. 21, 2002.
Human immunodeficiency virus/acquired immunodeficiency syndrome in the context of drug abuse. Report of the Executive Director, United Nations Economic and Social Council. Jan. 30, 2003 (12 pp.).
Hyman, Phelps & McNamara P.C.'s comments and objections dated Jul. 5, 2002 to the citizen petition.
Hyman, Phelps & McNamara P.C.'s comments dated May 22, 2002 on behalf of Purdue Pharma L.P. to 67 Fed. Reg. 13,114 of Mar. 21, 2002.

Hyman, Phelps & McNamara P.C.'s response dated May 9, 2002 on behalf of Purdue Pharma L.P. to 67 Fed. Reg. 17074 of Apr. 9, 2002.
Johnson et al., Daily versus alternate–day dosing of buprenorphine in the outpatient treatment of opioid dependence. CPDD 1994 Annual Scientific Meeting Abstracts.
Jones et al., Buprenorphine and naloxone interactions in heroin–dependent volunteers. CPDD 1994 Annual Scientific Meeting Abstracts.
Journal of Pain and Symptom Management. Apr. 7, 1992 (S3) (whole journal).
Kintz, Deaths involving buprenorphine: A compendium of French cases. Forensic Sci Int. Sep. 15, 2001;121(1–2):65–9.
Korte, Titration with TTS fentanyl systems for previously uncontrolled cancer pain, and Lipman's response thereto. Anesth Analg. Sep. 1994;79(3):612–4.
Kumar, Chemists selling illegal drugs to be booked in The times of India, Aug. 16, 2000.
Lasseter et al., Systemic pharmacokinetic (PK) study of buprenorphine (B) in mild to moderate chronic hepatic impairment (CHI). Amer Soc for Clin Phamcol and Therapeut. PI–4.
Liguori et al., Modification of respiratory effects of levorphanol by nalbuphine, butorphanol, and buprenorphine in rhesus monkeys. CPDD 1994 Annual Scientific Meeting Abstracts.
Mann et al., Buprenorphine alone or in combination with naltrexone for inpatient medically supervised opiate withdrawal. CPDD 1994 Annual Scientific Meeting Abstracts.
McCance–Katz, of American Academy of Addiction Psychiatry, letter to DEA Administration dated May 15, 2002 in response to proposed rule : Rescheduling of Buprenorphine from Schedule V to Schedule III, published in the Federal Register of Mar. 21, 2002.
McNeal, of FDA, Medical Review on IND 40,273, dated May 10, 1996.
McNeal, of FDA, Comments dated Aug. 30, 1996 on the protocols submitted on Aug. 5, 1996 in Serial No. #006 of IND 50,273.
McNicholas et al., Buprenorphine clinical practice guidelines. Field review draft. Nov. 17, 2000.
Mendelson et al., Buprenorphine treatment improves brain perfusion abnormalities in men with concurrent cocaine and heroin dependence: A spect brain imaging analysis. CPDD 1994 Annual Scientific Meeting Abstracts.
Miller, Memorandum to Brogden, Napp Pharmaceuticals Ltd., re Evaluation of clinical data received from Grunenthal buprenorphine TTS, Nov. 11, 1999 (5 pp.).
Non–Clinical Chronology for BTDS NDA from May 1996–Apr. 2000.
O'Connor et al., A pilot study of primary care–based buprenorphine maintenance. CPDD 1994 Annual Scientific Meeting Abstracts.
O'Keeffe, of Reckitt Benckiser Pharmaceuticals Inc. letter to DEA Administrator dated Apr. 18, 2002 in response to proposed rule : Rescheduling of buprenorphine from Schedule V to Schedule III, published in the Federal Register on Mar. 21, 2002.
Payne et al., The role of transdermal fentanyl in the management of cancer pain in Opioids in Anesthesia II (Estafanous, ed.), 1991(18):215–22.
Pharmaceuticals: Restrictions in Use and Availability, Mar. 2001 (up to p. 5 re Buprenorphine).
Pilot study on the dermal tolerability and adhesion of a buprenorphine patch and the absorption of the active substance over an application period of 72 hours in 6 healthy volunteers, Final Report, 1992.
Portenoy et al. Acute and chronic pain in Substance Abuse. A Comprehensive Textbook (Lowinson et al., eds.), 2$^{nd}$ ed. 2005. 52:691–721.
Preston et al., Abuse liability evaluation of buprenorphine in buprenorphine–treated patients. CPDD 1994 Annual Scientific Meeting Abstracts.
Report of the International Narcotics Control Board for 2001, United Nations Publication.
Rigas et al., Transdermal fentanyl: Practical use in the hospital and the home (undated).
Schuh, A comparison of buprenorphine's and naltrexone's opioid blockade abilities. CPDD 1994 Annual Scientific Meeting Abstracts.
Segal et al., A double blind, multicenter clinical trial comparing four doses of buprenorphine. CPDD 1994 Annual Scientific Meeting Abstracts.
Singh et al., Cases of buprenorphine abuse in India. Acta Psychiatr Scand. Jul. 1992;86(1):46–8.
Smith, Grunenthal buprenorphine trandermal system. Review of pharmacokinetic studies. 11/10/199 (7 pp.).
Steiberg et al., Acute toxic delirium in a patient using transdermal fentanyl. Anesth Analg. Dec. 1992;75(6):1014–6.
The Safety of High Doses of Buprenorphine. Table of Contents and Introduction (undated).
Using buprenorphine for office–based treatment of opiate addiction. Recommendations to the CSAT of the SAMHSA, from CSAT's National Advisory Council, approved by the CSAT's National Advisory Council on Sep. 15, 1999 (28 pp.).
Wang et al., Negative opiates in urine of patients on buprenorphine study. CPDD 1994 Annual Scientific Meeting Abstracts.
WHO Critical review of psychoactive substances. 33$^{rd}$ Expert Committee on Drug Dependence, Sep. 17–20, 2002.
WHO Expert Committee on Drug Dependence 25$^{th}$ Report. WHO Technical Report Series. 1989.
WHO Expert Committee on Drug Dependence 32$^{nd}$ Report. WHO Technical Report Series. 2001.
WHO Expert Committee on Drug Dependence 33$^{rd}$ Report. WHO Technical Report Series. 2003.
Wodak, Additional commentary on a proposed review of the classification of buprenorphine in Schedule III of the 1971 Convention on Psychotropic substances (undated).
Ziedonis et al., Depression in cocaine abusing opioid addicts treated with buprenorphine versus methadone. CPDD 1994 Annual Scientific Meeting Abstracts.
Bell et al., Evaluation of transdermal fentanyl for multi–day analgesia in postoperative patients. Anesth Analg. 1989; Abstract S22.
Fiset et al., Biopharmaceutics of a new transdermal fentanyl device. Anesthesiology. Sep. 1995;83(3):459–69.
Gibaldi, Prolonged–Release medication in Biopharmaceutics and Clinical Pharmacokinetics. 1984;3$^{rd}$ ed.:113–30.
Hadgraft, In vitro testing of dermal and transdermal products. Mar. 28, 2001 (6 pages).
Harvey–Clark et al., Transdermal fentanyl compared with parenteral buprenorphine in post–surgical pain in swine: a case study. Lab Anim. Oct. 2000;34(4):386–98.

Imoto et al., Transdermal prodrug concepts: permeation of buprenorphine and its alkyl esters through hairless mouse skin and influence of vehicles. Biol Pharm Bull. Feb. 1996;19(2):263–7.
Michaels et al., Drug permeation through human skin: Theory and in vitro experimental measurement. AIChE J. 1975;21(5):985–96.
New Approaches to Pain Management. Progress in Palliative Care. Meeting Report. Oct. 12–13, 2000; 100–101.
Portenoy et al., Transdermal fentanyl for cancer pain. Repeated dose pharmacokinetics. Anesthesiology. Jan. 1993;78(1):36–43.
Stinchcomb et al., Permeation of buprenorphine and its 3–alkyl–ester prodrugs through human skin. Pharm Res. Oct. 1996;13(10):1519–23.
Hihuchi, William I., Ph.D. et al., "Particle Phenomena and Coarse Dispersions" Chapter 21, p. 194.
Colloidal Dispersions, p. 267.
Climara® Product Information, Physicians' Desk Reference (1998) pp. 672–676.
Catapres TTS® Product Information, Physicians' Desk Reference (1998) pp. 610–612.
Chien, pp. 31–44, col. 8 and 9.
McQuinn, R.I., et al., "Sustained oral mucosal delivery in human volunteers of buprenorphine from a thin non–eroding mucoadhesive polymeric disk" J. Contr. Rel. (1995).
Van Buskirk, G.A. et al., "Scale–up of adhesive transdermal drug delivery systems" Pharmaceutical Research 14(7) (1997).
Sadée, W. et al., "Buprenorphine: Differential interaction with opiate receptor subtypes in vivo" J. Pharm. Exp. Ther. 223(1) 1982.
Kuhlman, J.J., et al., "Human pharmacokinetics of Intravenous, sublingual and buccal buprenorphine" J. Anal. Toxicol. v 20 (1996).
Roy, S.D. et al., Transdermal delivery of buprenorphine through cadaver skin J. Pharm. Sci. 83(2): 126–30 (1994).
Wilding, I.R. et al., "Pharmacokinetic evaluation of transdermal buprenorphine in man" Int.I J. Pharmaceutics 132:81–7 (1996).
Roy et al., "Controlled transdermal delivery of fentanyl: characterizations of pressure–sensitive adhesives for matrix patch design," J Pharm Sci. May 1996, 85(5):491–5.
Friend et al., Simple alkyl esters as skin permeation enhancers. J. Controlled Release 1988 9:33–41.
Friend et al., Transdermal delivery of levonorgestrel I: Alkanols as permeation enhancers in vitro, J. Controlled Release 1988 7:243–50.
Agin M, Kazierad DJ, Abel R, et al., Assessing QT variability in healthy volunteers. J. Clin. Phamacol. 2003; 43:1028.
Ahmadi, J. et al., Treatment of heroin dependence. German Journal of Psychiatry 2004;7(2): 1–5.
Baker JR. Effect of buprenorphine and antiretroviral agents on the QT interval in opioid–dependent patients. Annals of Pharmacotherapy 2006; 40:392–6.
Bauer, K.H. et al. Pharmazuetische Technologie, (1986) pp. 362–365.
Bigelow GE. Forward. In: Cowan A, Lewis JW, eds. Buprenorphine: Combating Drug Abuse With a Unique Opioid. New York, NY: Wiley–Liss: 1995:xi–xiii.
Bliesener N, et al., Plasma Testosterone and Sexual Function in Men Receiving Buprenorphine Maintenance for Opioid Dependence. The Journal of Clinical Endocrinology & Metabolism 90(1):203–6, 2005.
Boger RH. Renal impairment: a challenge for opioid treatment? The role of buprenorphine. Palliative medicine 2006; 20:S17–S23.
Briefing document, cardiovascular and renal drug products advisory committee. May 29, 2003. Division of reproductive and arologic drug products. Apr. 29, 2003. Available at: http://www.fda.gov/ohrms/dockets/ac/03/briefing/3956B1_01_FDA–alfuzosin.pdf.
Bruce RD. Pharmacokinetic interactions between buprenorphine and antiretroviral mediations. Clinical Infectious Diseases 2006; 43 (Suppl 4):S216–S223.
Cherny NJ, Chang V, Frager G, Ingham JM, Tiseo Pj, Popp B, Portenoy RK, Foley KM, Opioid Pharmacotherapy in the Management of Cancer Pain: A Survey of Strategies Used by Pain Physicians for the Selection of Analgesic Drugs and Routes of Administration. Cancer 1995; 76:1288–1293.
Ciraulo DA. Pharmacokinetics and pharmacodynamics of multiple sublingual buprenorphine tablets in dose–escalation trials. Journal of Clinical Pharmacology 2006;46(2):179–92.
Cranmer, K. W. et al., Transdermal buprenorphine (BTDS) on associated health outcomes in th elderly. Presented at the 11th World Congress on Pain, Sydney, Australia, Aug. 21–26, 2005; Abstr 691–P297. (Study sponsored by Purdue Pharma L.P.).
Cymbalta® ((duloxetine hydrochloride) Delayed–release Capsules) Package Insert.
Dahan A. Opioid effects on respiratory function and analgesia: New data on buprenorphine and fentanyl in a new human model [abstract]. 3rd Research Forum of the European Association for Palliative Care, Stresa, Italy, 2004.
Duragesic® [package insert]. Titusville, NJL Janssen Pharmaceutica; 2001.
Eissenberg T et al., Buprenorphine's physical dependence potential: Antagonist–precipitated withdrawal in humans. J. Pharmacol. Exp. Ther. 276: 449–459, 1996.
Escher, M. et al., Pharmacokinetics and analgesic effects of intravenous buprenorphine (abstract). Clinical Pharmacology and Therapeutics 2005; 77(2 Suppl): 51.
Fleiss JL. Statistical Methods for Rates and Proportions. 2nd ed. New York, NY: John Wiley & Sons; 1981:33–45, 272–273 (Table A.3).
Flitz J. Effects of intermittent hemodialysis on buprenorphine and norbuprenorphine plasma concentrations in chronic pain patients treated with transdermal buprenorphine. European Journal of Pain 2006;10(8):743–8.
Gaulier J–M, et al., Ingestion of High–Dose Buprenorphine by a 4 Year–Old Child. Journal of Toxicology–Clinical Toxicology 42(7):993–5, 2004.
Gerra G. Naltrexone and buprenorphine combination in the treatment of opioid dependence. Journal of psychopharmacology 2006;20(6):806–14.
Hale ME, Ahdieh H, Ma T, Rauck R, for the Oxymorphone ER Study Group. Efficacy and Safety of OPANA ER (Oxymorphone Extended Release) for Relief of Moderate to Severe Chronic Low Back Pain in Opioid–Experienced Patients: A 12–Week, Randomized, Doubleblind, Placebo–controlled Study. J Pain 2007; 8(2):175–184.
Halpern SD, Karlawish JHT, Berlin JA. The Continuing Unethical Conduct of Underpowered Clinical Trials. JAMA 2002; 288:358–362.
Heel RC, Brogden RN, Speight TM, Avery GS. Buprenorphine: a review of its pharmacological properties and therapeutic efficacy. Drugs. 1979; 17:81–110.

Heilman, K. Therapeutische Systeme (1984) pp. 26–27 and pp. 48–53.

Herve S, et al., Acute hepatitis due to buprenorphine administration. European Journal of Gastroenterology & Hepatology 16(10):1033–7, 2004.

Hoskin PJ, Hanks GW. Opioid agonist–antagonist drugs in acute and chronic pain states. Drugs. 1991; 41(3):326–344.

ICH harmonized tripartite guideline: the clinical evaluation of QT/QTc interval prolongation and proarrhythmic potential for non–antiarrhythmic drugs, E14, Final Draft May 12, 2005. Available at [http://www.ich.org/cache/compo/475–272–1.html#E14].

Jagadheesan K and Muihead D., Possible manic potential of buprenorphine [letter]. Australian and New Zealand Journal of Psychiatry 37*8):560–1, 2004.

Katchman AN, McGroary KA, Kilborn MJ, et al., Influence of opioid agonists on cardiac human ether–a–go–go–related gene K(+) currents, 2002. J Pharmacol Exp Ther 303:688–94.

Kolloch RE, Mehlburger L, Schumacher H, Göbel BO. Efficacy and safety of two different galenic formulations of a transdermal clonidine system in the treatment of hypertension. Clin Auton Res. 1993;3:373–378.

Kosten T, et al., Depression Predicts Higher Rates of Heroin Use on Desipramine with Buprenorphine than with Methadone. The American Journal of Addictions 13:191–201, 2004.

Krantz, M.J. et al., Effects of buprenorphine on cardiac repolarization in a patient with methadone–related torsade de pointes. Pharmacotherapy 2005; 25(4):611–614.

Landau, C.J. et al., The safety and tolerability of buprenorphine 7–day transdermal system in patients with nonmalignant pain syndromes responsive to opioids. Presented at the 11th World Congress on Pain, Sydney Australia, Aug. 21–26, 2005; Abstr. 690–P296 (Study sponsored by Purdue Pharma L.P.)

McCance–Katz EF. Interactions between buprenorphine and antiretrovirals. II. The protease inhibitors nelfinavir, lopinavir/ritonavir, and ritonavir. Clinical infectious Diseases 2006; 43 (Suppl 4):S235–S246.

McCance–Katz EF. Interactions between buprenorphine and antiretrovirals. I. The nonnucleoside reserve–transcriptase inhibitors efavirenz and delavirdine. Clinical infectious Diseases 2006; 43 (Suppl 4):S224–S234.

McMahon FG, Jain AK, Vargas R, Fillingim J. A double–blind comparison of transdermal clonidine and oral captopril is essential hypertension. Clin. Ther. 1990; 12:88–100.

Muriel, C. et al., Effectiveness and tolerability of the buprenorphine transdermal system in patients with moderate to severe chronic pain: a multicenter, open–lable, uncontrolled, prospective, observational clinical study. Clinical Therapeutics 2005; 27(4):451–462. (Study sponsored by Grunenthal GmbH).

Neri, S. et al., Randomized clinical trial to compare the effects of methadone and buprenorphine on the immune system in drug abusers. Psychopharmacology 2005; 179(3): 700–704.

Nielsen, S.; Taylor, D.A. The effect of buprenorphine and benzodiazepine on respiration in the rat. Drug and Alcohol Dependence 2005;79:95–101.

Noveck, R. et al., Lack of effect of inhibitor ketoconazole on transdermally administered buprenorphine. Presented at the 106th Annual Meeting of the American Society for Clinical Pharmacology and Therapeutics, Orlando, FL., Mar. 2–5, 2005. (Study sponsored by Purdue Pharma L.P.).

Opana® ER ((Oxymorphone Hydrochloride) Extended Release Tablets)) Package Insert.

Patterson S, Agin M, Anziano R, et al., Investigating drug–induced QT and QTc prolongation in the clinic: a review of statistical design and analysis considerations. Report from the pharmaceutical research and manufacturers of American QT statistics expert team. Drug Information Journal 2003:39:243–265.

Philipz, J. et al., Pharmacokinetics of transdermal buprenorphine (Transtec®) in patients with renal insufficiency. Presented at the 9th Congress of the European Association for Palliative Care, Aachen, Germany, Apr. 8–10, 2005. (Study sponsored by Grünenthal GmbH).

Pimay S, et al., A critical review of the causes of death among post–mortem toxicological investigations: analysis of 34 buprenorphine–associated and 35 methadone–associated deaths. Addiction 99: 978–88, 2004.

Quang–Cantagrel N.D., Wallace M.S., Magnuson S.K. Opioid Sunstitution to Improve the Effectiveness of Chronic Noncancer Pain Control: A Chart Review. Anest Anag 2000; 90:933–937.

Raja SN, Haythornthwaite, JA, Pappagallo M, Clark MR, Travison TG, Sabeen S, Royall RM, and Max MB. Opioids versus antidepressants in postherpetic neuralgia: A randomized, placcebo–controlled trial. Neurology. 59: 1015–1021, 2002.

Rozenbaum H, Birkhauser M, DeNooyer C, et al., Comparison of two estradiol transdermal systems (Oesclim® 50 and Estraderm TTS® 50). II. Local skin tolerability. Maturitas. 1996; 25:175–185.

Schmid–Grendelmeier P. A comparison of the skin irritation potential of transdermal fentanyl versus transdermal buprenorphine in middle–aged to elderly healthy volunteers. Current Medical Research and Opinion 2006;22(3):501–9.

Sittl, R. et al., Equipotent doses of transdermal fentanyl and transdermal buprenorphine in patients with cancer and noncancer pain: Results of a retrospective cohort study. Clinical Therapeutics 2005; 27(2):225–237. (Study sponsored by Grünenthal GmbH).

Soyka, M. et al., Less impairment on one of portion of a driving–relevant psychomotor battery in buprenorphine–maintained that in methadone–maintained patients: results of a randomized clinical trial. Journal of Clinical Psychopharmacology 2005; 25(5): 490–493.

Sporer KA, Buprenorphine: A Primer for Emergency Physicians. Annals of Emergency Medicine 43(5):580–4, 2004.

Turk DC, Melzack R. The measurement of pain and the assessment of people experiencing pain. In: Turk DC, Melzack R, eds. Handbook of Pain Assessment. New York, NY: The Guilford Press; 1992:3–12.

World Medical Association Declaration of Helsinki. Ethical Principals for Medical Research Involving Human Subjects. 2004.

Yassen A. Mechanisms–based PK/PD modeling of the respiratory depressant effect of buprenorphine and fentanyl in healthy volunteers. Clinical Pharmacology & Therapeutics 2007:81(1):50–8.

Wallenstein, "Crossover Trials in Clinical Analgesic Assays: Studies of Buprenorphine and Morphine" Pharmacotherapy 6(5):228–235 (1986).

Johnson RE, Fudala PJ, Payne R. Buprenorphine: considerations for pain management. *JPain Symptom Manage* 2005:29:297–326.

Lemens HJM, Wada DR, Munera C, El–Tahtawy A, Stanski DR. Enriched analgesic efficacy studies: an assessment by clinical trial simulation. *Contemp Clin Trials*, 2006:27; 165–173.

Cranmer K, Landau CJ, Friedman My Turner NG, Ripa SR. The safety and tolerability 0 of 7–day buprenorphine.TDS in the analgesic management of pain in the elderly—a 6–month evaluation. www.ASCP.com/education/postersandpapersam05.com. Poster 34. (Study BUP 3002S).

D'Ambrosio P, McCarberg By Landau CJ, Hsu Y, Colucci R, Ripa S. Conversion from Vicodin® to buprenorphine transdermal system in subjects with osteoarthritis pain. *J Pain* 2006; 7(4) (Suppl 2): S5 1. Abstract 801. (Study BUP3018).

Harris S, Hoelscher D, Kristensen A, O'Keefe S, Schemera A. Effects of buprenorphine transdermal system 10 mg and 2×20 mg on QT intervals in healthy subjects. *Clin Pharmacol ner* 2006; 79(2):P35. (Study BUP1011).

Razzetti AJ, Carr W, Landau CJ, Munera C, Ripa SR, Sessler N. Effectiveness of 7–day buprenorphine transdermal system in the management of chronic nonmalignant pain syndromes. *J Pain* 2005; 6(3): Suppl 1:542. (Study BUP 3201).

Schnoll SH, Smith MY, Colucci RD, Munoz A. Development of a denominator for calculating rates of opioid abuse. CPDD Annual Meeting Abstractcs. 2004. (Study BUP3018 and non BTDS studies).

Shannon MJ, Kivitz A, Landau CJ, Sessler NE, Xia Y, Ripa SR. Buprenorphine transdermal system in chronic pain due to osteoarthitis. *Arch Phys Med Rehabil* 2005; 86(9):e32. (Study BUP3012).

Spyker DA, Hale ME, Lederman My Creanga DL, Coles C, Reder RF, Long–term use of buprenorphine transdermal system (BTDS) in patients with chronic pain. *JAm Geriatr Soc* 2002; 50(4 suppl):S66. Abstract P162. (Study BP96–0103).

Spyker DA, Hale ME, Munera CL, Wright C. Treatment of patients with chronic low back pain with buprenorphine transdermal system (BTDS) compared with hydrocodone/acetaminophen. *Pain Mgmt* 2001 :PF2001–85. (Study BP98–1201z).

Wright C, Zalman M–A, Haddox JD, Kramer ED, Colucci RD, D'Ambrosio P., Systematic assessment of abuse or diversion in a clinical trail of analgesics. CPDD Annual Meeting Abstracts. 2006. (Study BUP3018).

Barry, "Reflections on Transdermal Drug Delivery", *Pharmaceutical Science & Technology Today* 2(2):41–43 (1999).

Catapres TTS® Product Information, Physicians' Desk Reference 1998, pp. 610–612.

Climara® Product Information, Physicians' Desk Reference 1998, pp. 672–6.

Kuhlman, Jr., et al., Human pharmacokinetics of intravenous, sublingual, and buccal buprenorphine. J Anal Toxicol. Oct. 1996;20(6):369–78.

McQuinn, R.L. et al., Sustained oral mucosal delivery in human volunteers of buprenorphine from a thin non–eroding mucoadhesive polymeric disk. Journal of Controlled Release 1995, 34:243–50.

Roy et al., Transdermal delivery of buprenorphine through cadaver skin. J Pharma Sci 1994, 83(2):126–30.

Sadee et al., Buprenorphine: Differential interaction with opiate receptor subtypes in vivo. The Journal of Pharmacology and Experimental Therapeutics, Copyright © 1982, 223(1):157–62.

Van Buskirk et al, Scale–up of adhesive transdermal drug delivery systems. Pharmaceutical Research 1997, 14(7).

Wilding et al., Pharmacokinetic evaluation of transdermal buprenorphine in man. International Journal of Pharmaceutics 1996, 132:81–7.

Ashcroft et al., Buprenorphine TDS: Comparison with sublingual buprenorphine in osteoarthritic pain. 10$^{th}$ World Congress on Pain, Aug. 19, 2002 Abstract 510–P144.

Becker et al., Transdermal buprenorphine: Abuse potential assessment in non–opioid–dependent volunteers. CPDD Jun. 16–21, 2001 Abstract 40 (w/ PowerPoint presentation).

Boas et al., Clinical actions of fentanyl and buprenorphine the significance of receptor binding. Br. J. Anaesth. 1985, 57:192–6.

Buprenorphine Product Photo, Norspan™ 5, 10 & 20.

Capurso et al., Matrix transdermal technology: focus on a buprenorphine transdermal system. ASHP Midyear Clinical Meeting, Dec. 2001, p. 231D Abstract (w/ PowerPoint presentation).

Colucci, History of Buprenorphine. PowerPoint presentation presented in Dec. 2002.

El–Tahtawy et al., 7–Day bioavailability of buprenorphine from a novel transdermal system in demographic subgroups. 13$^{th}$ Annual ACCP Meeting Abstracts, Sep. 23–25, 2001, p. 1027, Abstract 56 (w/ PowerPoint presentation).

Friend et al., Simple alkyl esters as skin permeation enhancers. J. Controlled Release 1988 9:33–41.

Friend et al., Transdermal delivery of levonorgestrel I: Alkanols as permeation enhancers in vitro, Controlled Release 1988 7:243–50.

Hale et al., Analgesic efficacy of buprenorphine transdermal systems vs. Oxy/APAP in patients with chronic low back pain. The Gerontologist, vol. 41, Special Issue 1, Oct. 2001, Program Abstracts from the Gerontological Society of America 54$^{th}$ Annual Scientific Meeting, Nov. 15–18, 2001, p. 25 (w/ PowerPoint presentation first presented on May 7, 2002 and revised on Oct. 30, 2002).

Hale et al., Dose proportionality and the dose response of buprenorphine transdermal system in patients with chronic pain. 13$^{th}$ Annual ACCP Meeting Abstracts, Sep. 23–25, 2001, p. 1027, Abstract 58 (w/ PowerPoint presentation).

Hale et al., Long–term use of buprenorphine transdermal system (BTDS) in patients with chronic pain. PowerPoint presentation presented May 2002.

Hale et al., Treatment of patients with chronic low back pain with buprenorphine transdermal systems (BTDS) compared with hydrocodone/acetaminophen. National Clinical Symposium of the American College of Nurse Practitioners, Oct. 20, 2001 Abstract (w/ PowerPoint presentation).

Jaffe et al., Opioid Analgesics and Antagonists. The Pharmacological Basis of Therapeutics (8$^{th}$ ed. Pergamon Press) 1990, Chap. 21, pp. 485–521.

Jeal et al., Transdermal fentanyl. A review of its pharmacological properties and therapeutic efficacy in pain control. Drugs, Jan. 1997, 53(1):109–38. Review.

Kaiko et al., Transdermal buprenorphine. Memorial Sloan Kettering Manuscript, Chapter 15 (w/ PowerPoint Final presentation presented May 2, 2003).

Lasseter et al., Systemic pharmacokinetic (PK) Study of buprenorphine (B) in mild to moderate chronic hepatic impairment (CHI). Amer. Society for Clinical Pharmacology and Therapeutics 69(2) 2 (P1–4) Feb. 2001 Abstract (w/ PowerPoint presentation presented Mar. 2001).

Marquardt et al., Fentanyl remaining in a transdermal system following three days of continuous use. Ann Pharmacother Oct. 1995, 29(10):969–71.

Müller et al., Intra—and postoperative interactions between the 2 opioids fentanyl and buprenorphine. Anaesthesist. Apr. 1986, 35(4):219–25 (in German, w/ English abstract).

Noveck et al., Pharmacokinetics of buprenorphine transdermal system (BTDS 10) employing the LPS pyrogen model. Clinical Pharmacology & Therapeutics 69(2):3 200 2001 Abstract PI–7 (w/ PowerPoint presentation).

Payne et al., Guidelines for the clinical use of transdermal fentanyl. Anticancer Drugs. Apr. 1995, 6 Suppl 3:50–3.

Peng et al., A review of the use of fentanyl analgesia in the management of acute pain in adults. Anaesthesiology 1999, 90:576–99.

Reidenberg et al., Absolute bioavailability of a novel buprenorphine transdermal system (BTDS) applied for 7 days. J. Clin Pharmacol. 2001 41(9):1014–1033, Abstract 55, p. 1026 (w/ PowerPoint presentation presented in the ACCP Meeting, Sep. 2001).

Reidenberg et al., Daily pharmacokinetic performance of a buprenorphine transdermal system (BTDS) for up to 7 days. J. Clin Pharmacol. 2001 41(9):1014–1033, Abstract 57, p. 1027 (w/ PowerPoint presentation).

Reidenberg et al., Pharmacokinetics and safety of buprenorphine transdermal system (BTDS) for 7–Day application comparing healthy elderly and young adult subjects. Am Pain Soc, 19$^{th}$ Ann. Sci. Meet., Nov. 2–5, 2000 Abstract 776 (w/ PowerPoint presentation).

Reidenberg et al., Physiologic effects of buprenorphine transdermal system (BTDS) dose escalation in the young, healthy elderly and elderly hypertensive subjects, FASEB J. 15(4), Mar. 2001 Abstract 457.3 (w/ PowerPoint presentation presented Apr. 2001).

Roy et al., "Controlled transdermal delivery of fentanyl: characterizations of pressure–sensitive adhesives for matrix patch design," J Pharm Sci. May 1996, 85(5):491–5.

Sandler et al., A Double–blind, placebo–controlled trial of transdermal fentanyl after abdominal hysterectomy. Analgesis, respiratory, and pharmacokinetic effects, Anesthesiology Nov. 1994, 81(5):1169–80; discussion 26A.

Spyker et al., Effectiveness and safety of buprenorphine transdermal system (BTDS) compared with hydrocodone/acetaminophen in the treatment of patients with chronic low back pain. J. Pain 2002 3(Suppl. 1):14 Abstract 653 (w/ PowerPoint presentation).

Spyker et al., Effectiveness of buprenorphine transdermal system (BTDS) compared with oxycodone/acetaminophen and placebo in the treatment of patients with chronic back pain. Morial Convention Center, Oct. 15, 2001 Abstract (w/ PowerPoint presentation).

Spyker et al., Transdermal buprenorphine system (BTDS) in patient–controlled Analgesia (PCA). PowerPoint presentation presented Mar. 2000.

Spyker et al., Analgesic efficacy and safety of buprenorphine transdermal system (BTDS) in patients with osteoarthritis. The Journal of Pain 3(2, Suppl. 1):12 Abstract 645(w/ PowerPoint presentation).

Spyker et al., Effect Size (ES) Meta–analysis Approach to Noninferiority Clinical Trials. Clinical Pharmacology & Therapeutics 69(2):33 Abstract PII–3 (w/ PowerPoint presentation presented Mar. 5, 2001). 0.

Transtec Summary of Product Characteristics, Oct. 2003.

* cited by examiner

AMENDED
FIG. 2
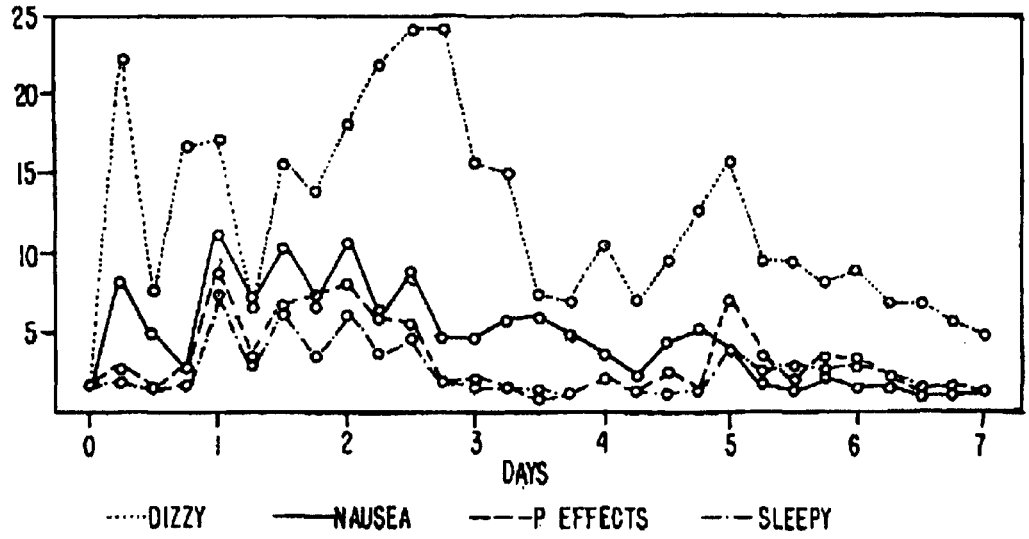

METHOD OF PROVIDING SUSTAINED ANALGESIA WITH BUPRENORPINE

Matter enclosed in heavy brackets [ ] appears in the original patent but forms no part of this reissue specification; matter printed in italics indicates the additions made by reissue.

[This application is a continuation of Ser. No. 08/939,068, filed Sep. 29, 1997 now U.S. Pat. No. 5,688,547 Provisional Application No. 60/038,919 filed Feb. 24, 1997.]

*More than one reissue application has been filed for reissue on U.S. Pat. No. 6,231,886. This application is a continuation of reissue application No. 11/033,107, filed on Jan. 11, 2005, now abandoned, which is a reissue of application Ser. No. 09/311,997, filed on May 14, 1999, now U.S. Pat. No. 6,231,886, which is a continuation of application Ser. No. 08/939,068, filed on Sep. 29, 1997, now U.S. Pat. No. 5,968,547, which claims priority to U.S. Provisional Application No. 60/038,919, filed Feb. 24, 1997.*

BACKGROUND OF THE INVENTION

It is the intent of all sustained-release pharmaceutical preparations to provide a longer period of pharmacologic effect after the administration of a drug than is ordinarily experienced after the administration of immediate release preparations of the same drug. Such longer periods of efficacy can provide many inherent therapeutic benefits that are not achieved with corresponding immediate release preparations. The benefits of prolonged analgesia afforded by sustained release oral analgesic preparations have become universally recognized and oral opioid analgesic sustained-release preparations are commercially available.

Prolonged analgesia is particularly desirable in patients suffering from moderate to severe pain, such as cancer patients. Available oral preparations provide a duration of effect lasting e.g., about twelve hours (and sometimes 24 hours) such that a drug may only have to be administered to a patient one to three times a day. For example, morphine, which has been considered to be the prototypic opioid analgesic, has been formulated into twice-daily, oral controlled release formulations (e.g., MS Contin® tablets, commercially available from The Purdue Frederick Company).

Another approach to sustained delivery of a therapeutically active agent are transdermal delivery systems, such as transdermal patches. Generally, transdermal patches contain a therapeutically active agent (e.g., an opioid analgesic), a reservoir or matrix containing the opioid or other active ingredient(s) and an adhesive which allows the transdermal device to adhere to the skin, allowing for the passage of the active agent from the device through the skin of the patient. Once the active agent has penetrated the skin layer, the drug is absorbed into the blood stream where it can exert a desired pharmacotherapeutic effect, such as analgesia.

Transdermal delivery systems in which an opioid analgesic is the active ingredient have been contemplated. For example, a commercially available opioid analgesic transdermal formulation is Dugagesic® (commercially available from Janseen Pharmaceutical; active ingredient is fentanyl). The Duragesic® patch is said to provide adequate analgesia for up to 48 to 72 hours (2 to 3 days).

Buprenorphine, a partially synthetic opiate, has also been contemplated for prolonged analgesia. Although other types of opioid analgesic transdermal formulations have been reported in the literature (such as fentanyl, discussed above), buprenorphine transdermal delivery systems are of particular interest because buprenorphine is a potent, partial agonist opioid analgesic with desirable therapeutic properties. For example, buprenorphine is 50 to 100 times more potent than morphine, but has a much safer therapeutic index than morphine (see Wallenstein S L, et al., Crossover Trials in Clinical Analgesic Assays: Studies of Buprenorphine and Morphine, Pharmacotherapy, G(5): 225–235, 1986 hereby incorporated by reference). Further, the partial agonist properties of buprenorphine are useful in the treatment of opioid addiction.

There are several types of transdermal formulations of buprenorphine reported in the literature. See, for example, U.S. Pat. No. 5,240,711 (Hille et al.), U.S. Pat. No. 5,225,199 (Hidaka et al.), U.S. Pat. No. 5,069,909 (Sharma et al.), U.S. Pat. No. 4,806,341 (Chien et al.), and U.S. Pat. No. 5,026,556 (Drust et al.), all of which are hereby incorporated by reference.

Buprenorphine has a low oral bioavailability and has been considered by certain of those skilled in the art to be like other narcotics which are habit-forming (see, e.g., U.S. Pat. No. 5,240,711 to Hille, et al.) and induce tolerance (see, e.g., U.S. Pat. No. 5,613,958 to Kochinke, et al.). As reported in Hille, et al., experts are of the opinion that the form of administration of a medicinal drug contributes to the risk of addiction, and higher than necessary blood levels created immediately after administration of a drug such as buprenorphine, followed by a drastic decrease (causing in succession euphoria and then ineffective pain treatment), cause the patient to start to long for the next dosage (referred to as an "iatrogenic" addiction). In the case of buprenorphine, Hille et al. reported that continuous infusion would be considered the most suitable mode to avoid such an iatrogenic addition by providing constant blood levels; however, continuous infusion requires physician control and insertion of a cannula (which may cause inflammation at the site). This problem is considered to be overcome by Hille, et al. by virtue of their use of a transdermal delivery system which includes buprenorphine or one of its pharmaceutically compatible salts and which releases the drug over a period of at least 24 hours in a controlled manner, and ensures that the buprenorphine does not notably decompose when the transdermal delivery system is stored, and which further ensures that the buprenorphine in-vivo penetrates through the skin at the required amount.

Kochinke et al. describes a transdermal system for the modulated administration of tolerance-inducing drugs. Buprenorphine is identified therein as such a drug. The system is designed to deliver the drug through the patient's skin via a three-phase drug delivery profile. In the first phase, which begins with patch application and ends at 2–10 hours after patch application, plasma levels of the drug are obtained. This phase is followed by a second phase in which therapeutic plasma levels of the drug are maintained. The second phase begins at about two to ten hours after patch application and ends at about 8–18 hours after patch application. In a third phase, sub-therapeutic levels of the drug are maintained, via inherent patch design and/or patch removal. The rationale behind the drug delivery profile of Kochinke et al. is that initial high blood levels may be more effective when followed by a period of decreasing dosage (down to sub-therapeutic levels), than if the blood levels are maintained either at the higher or lower level (i.e., sub-therapeutic levels) throughout the entire administration period. By virtue of this modulated profile, it is said that the onset of tolerance to the drug being administered can be prevented or greatly reduced.

Despite these advances in the art, there remains a need for methods of treating patients with buprenorphine that provide effective analgestic levels of buprenorphine for prolonged periods of time while eliminating or minimizing dependence, tolerance, and side effects, thus providing a safe and effective method of pain management.

OBJECTS AND SUMMARY OF THE INVENTION

It is an object of the present invention to provide a method which allows for reduced plasma concentrations of buprenorphine over a prolonged time period than possible according to prior art methods, while still providing effective pain management.

It is a further object of the present invention to provide a method for treating patients in pain with buprenorphine which achieves prolonged and effective pain management, while at the same time provides the opportunity to reduce side effects, dependence and tolerance which the patients may experience when subjected to prolonged treatment with a narcotic such as buprenorphine.

It is yet a further object to provide a method for the treatment of pain in patients by utilizing a transdermal delivery system which contains buprenorphine in a manner which maximizes the dosage interval, i.e., the interval during which the transdermal delivery system is maintained in contact with the skin, and minimizes the plasma concentrations in the patients during the dosage interval, while [surprisingly] maintaining effective pain management.

A further object of the invention is to provide a method for treating opioid-addicted patients in a manner which gradually reduces the plasma concentration of opioid in the patients' plasma while at the same time providing effective plasma concentrations for those patients to be detoxified.

The invention is directed in part to the [surprising] result that effective pain management is provided by providing a substantially first order rate of increase of blood plasma concentrations of buprenorphine over about a three day (e.g., 72 hours) time interval, followed by a prolonged time period of at least about two days (e.g., 48 hours) during which the plasma concentrations of buprenophine are maintained according to substantially zero order pharmacokinetics.

In accordance with the above objects and others, the invention relates in part to a method of effectively treating pain in humans, comprising administering buprenorphine to human patients in a manner such that the following mean plasma concentrations are achieved over a 72 hour dosing interval: a mean plasma concentration from about 0.3 to about 113 pg/ml at about 6 hours after initiation of the dosing interval; a mean plasma concentration from about 3 to about 296 pg/ml of about 12 hours after initiation of the dosing interval; a mean plasma concentration from about 11 to about 644 pg/ml at about 24 hours after initiation of the dosing interval; a mean plasma concentration from about 13 to about 630 pg/ml at about 30 hours after initiation of the dosing interval; a mean plasma concentration from about 15 to about 715 pg/ml at about 36 hours after initiation of the dosing interval; a mean plasma concentration from about 20 to about 984 pg/ml at about 48 hours after initiation of the dosing interval; a mean plasma concentration from about 21 to about 914 pg/ml at about 60 hours after initiation of the dosing interval; a mean plasma concentration from about 24 to about 850 pg/ml at about 72 hours after initiation of the dosing interval; and thereafter administering the buprenorphine in a manner such that the mean plasma concentrations are mntained from about 19 to about 850 pg/ml over at least the next 48 hours. In certain preferred embodiments, the dosing interval is maintained over a seven day period.

Any mode of admiration may be utilized to attain the above plasma concentrations over time. For example, the buprenorphine may be administered transdermally, parenterally, sublingually, orally, buccally, rectally, etc. Oral bioavailability of buprenorphine is very low (estimated as 15%). In order to better control plasma concentrations of buprenorphine within the concentrations desired in the herein-described inventive methods, it is preferred that the buprenorphine is administered via a transdermal delivery system or via continuous infusion.

In a further preferred embodiment of the invention, the method comprises applying a transdermal delivery system containing buprenorphine as the active ingredient onto the skin of patients which provide a release rate of buprenorphine over about a 72 hour dosing interval such that a maximum plasma concentration from about 20 pg/ml to about 850 pg/ml is attained (depending upon the dosage levels needed to maintain analgesia in the particular patients), and then maintaining the transdermal delivery systems on the skin of the patient for at least an additional 24 hour interval during which the plasma concentrations of buprenorphine in the patients are maintained above minimum effective concentrations of the drug and the patients continue to experience effective pain management during this additional dosing interval.

The invention is further directed to a method of effectively treating pain in humans, comprising administering buprenorphine transdermally to human patients such that mean relative release rates are achieved as follows: a mean relative release rate of from about 3 ug/hr to about 86 ug/hr from initiation of the dosing interval until about 72 hours thereafter; and a mean relative release rate of about 0.3 ug/hr to about 9 ug/hr from about 72 hours after the initiation of the dosing interval until at least about 120 hour hours after the initiation of the dosing interval. In certain preferred embodiments, the mean relative release rate of about 0.3 ug/hr to about 9 ug/hr is maintained from about 72 hours after the initiation of the dosing interval until at least about 168 hours after the initiation of the dosing interval.

The present invention is further related to a method of effectively treating pain in humans, comprising administering buprenorphine transdermally to human patients such that a mean relative release rate from about 3 ug/hr to about 86 ug/hr of buprenorphine is achieved until about 72 hours after the application of a transdermal delivery system, and [therafter] *thereafter* providing ([either] with the same transdermal delivery system [or upon removal of the system and replacement with a different transdermal delivery system]) a mean relative release rate of about 0.3 ug/hr to about 9 ug/hr from about 72 hours after the initiation of the dosing interval until at least about 120 hours after the initiation of the dosing interval, and preferably until at least about 168 hours after the initiation of the dosing interval.

In preferred embodiments, the [nethod] *method* comprises the application of a transdermal delivery system which is designed to [be] provide analgesia for about 72 hours, and which provides a release rate of the drug when applied to the skin which generally follows first order pharmacokinetics over than 72 hour period, and further comprises taking advantage of the fact that such transdermal delivery systems typically provide a dramatic drop-off in the release rate of buprenorphine after the first 72 hours, but nevertheless provide a relatively small but sufficient release of buprenorphine to maintain analgesia and desirable plasma concentrations in the patients over a further period of time of at least, e.g., preferably at least 48 hours, by leaving the transdermal delivery system in contact with the skin of the patient for such additional desired dosing interval, which may be as long as, e.g., an additional 96 hours or more. [Surprisingly, it] *It* has been found that such transdermal dosage systems exhibit substantially zero order release after about the initial 72 hour dosage interval, and therefore are capable of maintaining effective plasma concentrations of buprenorphine for a much longer period than previously reported in the prior art. [However, the inventive method also contemplates the possibility of utilizing a first transdermal delivery system which provides the desired substantially first order kinetics, and thereafter the removal of the first transdermal delivery system and its replacement with a second system which provides the desired substantially zero order pharmacokinetics for a prolonged period of time (e.g., at least about 24 hours, preferably at least about 48 hours, and most preferably about 96 hours). This second system may be a second transdermal delivery system which provides the afore-mentioned mean relative release rate of about 0.3 ug/hr to about 9 ug/hr. On the other hand, the second system may even utilize a different miode of administration, for example, continuous infusion].

The present invention is also related, in part, to a method of effectively treating pain in patients, comprising applying onto the skin of the patients a transdermal delivery system containing buprenorphine which transdermal delivery system delivers the buprenorphine substantially according to first order kinetics to provide a mean plasma concentration from about 24 to about 850 pg/ml about 3 days after application, and then maintaining the transdermal buprenorphine formulation in contact with the skin of the human patient for about 2 to about 6 additional days without removing the transdermal formulation, such that the patient continues to receive effective analgesia from the transdermal buprenorphine formulation.

The invention also provides, in certain preferred embodiments, an improvement in a method of treating pain in human patients by applying a 3 day transdermal delivery system containing buprenorphine onto the skin of the patient and maintaining the transdermal delivery system in contact with the skin for a 3 day dosing interval, the transdermal delivery system containing an amount of buprenorphine sufficient to provide effective analgesia in the patient for about 3 days, the improvement comprising maintaining the transdermal dosage form in contact with the patient's skin for at least 2 to about 6 additional days beyond the 3 day dosing interval.

The present invention also relates to a method of treating opioid addiction by administering buprenorphine transdermally to human patients which provides a release rate of the drug when applied to the skin which generally follows first order pharmacokinetics over a 72 hour period, such that the addict attains a buprenorphine plasma concentration from about 1000 to about 10,000 [μg/ml] *pg/ml*, and preferably from about 5000 to about 8000 [μg/ml] *pg/ml*, about 72 hours after application of a buprenorphine transdermal delivery system, and thereafter maintaining the [transdenal] *transdermal* delivery system in contact with the skin of the addict such that a mean relative release rate of buprenorphine approximating zero order kinetics over an additional dosing interval of at least about 48 hours, to provide the desired therapeutic effect (detoxification). In preferred embodiments the transdermal delivery system is maintained in contact with the addict's skin for about 7 days.

The methods of the present invention are described in further detail in the following sections. However, it should be understood that for purposes of the present invention, the following terms have the following meanings:

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain expressed versus side effects) to analgesic treatment by a physician as well as subjective evaluation of therapeutic treatment by the patient undergoing such treatment. The skilled artisan will understand that effective analgesia will vary according to many factors, including individual patient variations.

The term "breakthrough pain" means pain which the patient experiences despite the fact that the patient is being administered generally effective amounts of, e.g., an opioid analgesic such as buprenorphine.

The term "rescue" refers to a dose of an analgesic which is administered to a patient experiencing breakthrough pain.

The term "first order" pharmacokinetics is defined as plasma concentrations which increase over a specified time period. Drug release from suspension matrices according to first order kinetics may be defined as follows:

Amount released per area unit $Q=D_{eff}(2\cdot C_0-C_s)\cdot C_s\cdot t$ (First order kinetics)

$$D_{eff} = \text{apparent diffusion coefficient}\frac{M}{\sqrt{t}} = 2\cdot C_o\cdot\sqrt{D_{eff}/n}$$

$C_0$=initial drug concentration in the transdermal delivery system $C_s$=saturation concentration t=time Assumptions: perfect sink; diffusion of dissolved drug is rate controlling; therefore $$Q=\text{const}\cdot\sqrt{t}$$

Drug release from solution matrices according to first order kinetics may be defined as follows:

$$\text{Amount released per area unit } Q = \sqrt{2\cdot C_o}\left(D_{eff}\cdot\frac{t}{\pi}\right)\text{(First order kinetics)}$$

Assumptions: perfect sink; diffusion of dissolved drug is rate controlling: $M_1 \leqq 0.4M_0$ therefore $Q=\text{const}\cdot\sqrt{t}$.

The term "zero ordering" pharamacokinetics contemplates an amount of drug released from a buprenorphine formulation which substantially maintains plasma concentrations at a relatively constant level. For purposes of the present invention, a relatively constant plasma concentration is defined as a concentration which does not decrease more than about 30% over a 48 hour time period. Drug release from membrane-controlled systems may be defined as follows:

$$\text{Amount released per area unit } Q=\text{const (zero order dinetics)}$$

The term "mean relative rate" is determined from the amount of drug released per unit time from the transdermal delivery system through the skin and into the blood-stream of a human patient. Mean relative release rate may be expressed, e.g. as μg drug/cm$^2$/hr. For example, a transdermal delivery system that release 1.2 mg of buprenorphine wver a time period of 72 hours is considered to have a relative rate of 16.67 μg/hr. For purpose of the invention, it is understood that relative release rates may be change between any particular time points within a particular dosing interval, and the term therefore only reflects the overall release rate during the particular dosing interval. For purpose of the present invention, relative release rate should be considered sunonomous with the term "flux rate".

The term "sustained release" is defined for purposes of the purposes of the present as the release of the drug (opioid analgesic) from the transdermal formulation at such a rate that blood (e.g., plasma) concentration (levels) are maintained within the therapeutic range (above the minimum effective analgesic concentration or "MEAC") but below toxic levels over a period of time of about 3 days or longer.

The term "steady state" means that the blood plasma concentration curve for a given drug has been substantially repeated from dose to dose.

The term "minimum effective analgesic concentration" is defined for purposes of this invention as the minimum effective therapeutic blood plasma level of the drug at which at least some pain relief is achieved in a given patient. It will be well understood by those skilled in the medical art that pain measurement is highly subjective and great individual variations may occur among patients.

For purposes of the present invention, the term "buprenorphine" shall include buprenorphine base, pharmaceutically acceptable salts thereof, stereoisomers thereof, ethers and esters thereof, and mixtures thereof.

The term "overage" means for the purposes of the present invention the amount of buprenorphine contained in a transdermal delivery system which is not delivered to the patient. The overage is necessary for creating a concentration gradient by means of which the active agent (e.g., buprenorphine) migrates through the layers of the transdermal dosage form to the desired site on a patient's skin.

BRIEF DESCRIPTION OF THE DRAWINGS

The following drawings are illustrative of embodiments of the invention and are not meant to limit the scope of the invention as encompassed by the claims.

FIG. 2 is a graphical representation of pharmacodynamic variables wherein time (days) for Example 1;

DETAILED DESCRIPTION

Figure 1:
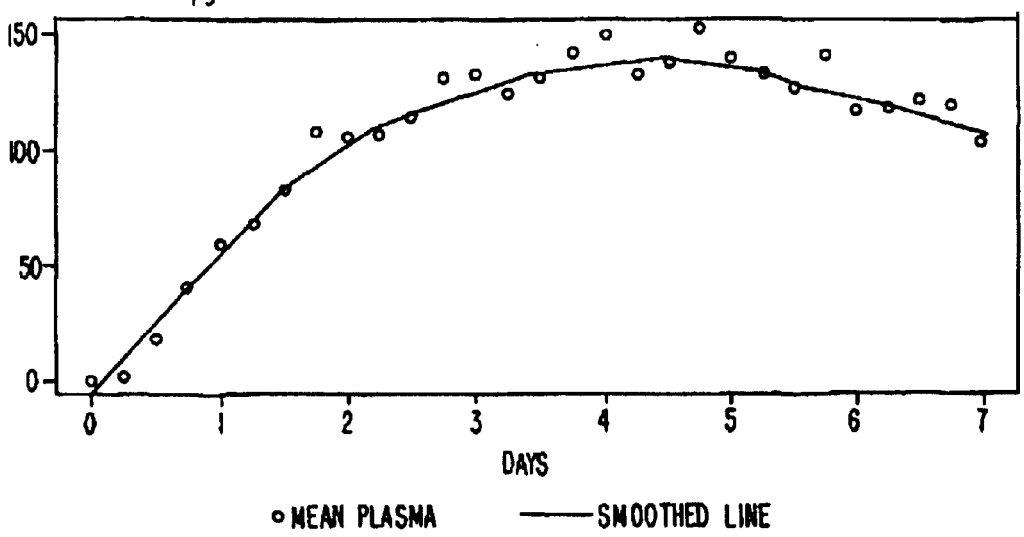
FIG. 1 is a graphical representation of the mean plasma concentration (pg/ml) versus time (days) of Example 1.

While chronic pain is often manageable with the use of the combinations of "mild" analgesics, and nonpharmacologic intervention, selected patients continue to experience unacceptably intense pain. Some patients with chronic pain cannot tolerate therapeutic doses of "mild" analgesics, while others develop pain of such severity that "strong" analgesics should be considered for subacute or chronic use.

The phrase "strong analgesics" encompasses, inter alia, several classes of opioid analgesics, including the partial agonists. Parenteral buprenorphine (a Schedule V drug under the Controlled Substances Act) is the only example of a partial agonist opioid analgesic currently marketed in the United States.

Partial agonists provide several therapeutic advantages in many patients when compared to morphine-like agonists and mixed agonists-antagonists. For example, unlike the mixed agonists-antagonists (e.g., pentazocine, butorphanol, nalbuphine), buprenorphine is derived of psychotomimetic adverse reactions; in comparison with agonists (e.g., morphine and fentanyl), the dose-responsive relationship for respiratory depression without buprenorphine is relatively low and the abuse liability of buprenorphine is less.

The chemical of name of buprenorphine is 21-cyclopropyl-7-[(S)-1-hydroxy-1,2,2-trimethylpropyl]-6,14-endo-ethano-6,7,8,14-tetrahydroorpavine. The molecular weight of buprenorphine base is 467,7; the empirical formula is $C_{29}H_41NO_4$.

The structural formula of buprenorphine is shown below:

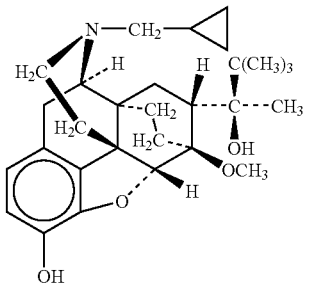

Buprenophine is an opioid partial agonist and shares many of the actions, such as analgesia, of opioid agonists. A "ceiling effect" to analgesia (i.e., no additional analgesia with increasing dose) is well documented with respect to buprenorphine in many animal models. It is highly lipophilic and dissociates slowly from opioid receptors. Buprenorphine is considered in the art to be a partial agonists at μ opioid receptors in the central nervous system ("CNS") and peripheral tissues. It is further thought that buprenorphine binds with high affinity to μ and $\kappa_1$ receptors, and, with lower affinity, to δ receptors. The intrinsic agonist activity at the κ receptor seems to be limited and most evidence suggests that buprenorphine has antagonist activity at κ receptors. The lack of κ agonism accounts for buprenorphine's freedom from the dysphoric acid and psychotomimetic effects often seen with agonistlantagonist drugs. Other studies suggest that the opioid antagonist effects of buprenorphine may be mediated via an interaction with δ opioid receptors.

It is known in the art that buprenorphine binds slowly with, and dissociates slowly from, the μ receptor. The high affinity of buprenorphine for the μ receptor and its slow binding to, and dissociates from, the receptor is thought to possibly account for the prolonged duration of analgesia, and in part, for the limited physical dependence potential observed with the drug. The high affinity binding may also account for the fact that buprenorphine can block the μ agonist effects of other administered opioids.

Like other opioid agonists, buprenorphine produces dose-related analgesia. The exact mechanism has not been fully explained, but analgesia appears to result from a high affinity of buprenorphine for μ and possibly κ opioid receptors in the CNS. The drug may also alter the pain threshold (threshold of afferent nerve endings to noxious stimuli). On a weight basis, the analgesic potency of parenteral buprenorphine appears to be about 25 to about 50 times that of parenteral morphine, about 200 times that of pentazocine, and about 600 times that of meperidine. Buprenorphine may produce sex-related differences in analgesia, with females requiring substantially less drug than males to produce adequate analgesia.

For a study of transdermal delivery of buprenorphine through cadaver skin, see Roy, Samir D. et al., "Transdermal Delivery of Buprenorphine Through Cadaver Skin",Journal of Pharmaceutical Sciences, Vol. 83, No. 2, pp 126–130, (1994), hereby incorporated by reference. For a discussion of buprenorphine pharmacokinetics resulting from application of a fillable transdermal therapeutic system, see Wilding, I. R. et al., "Pharmacokinetic evaluation of transdermal buprenorphine in man," International Journal of Pharmaceutics, 132 (1996) pp. 81–87, hereby incorporated by reference. For a discussion of the permeation of buprenorphine and alkyl esters thereof, see Imoto, et al., "Transdermal Prodrug Concepts: Permeation of Buprenorphine and its Alkyl Esters Through Hairless Mouse Skin and Influence of Vehicles," Biol. Pharm. Bull., 19(2)263–267 (1996), hereby incorporated by reference.

Buprenorphine has a low abuse liability compared to fill agonist opioids. Although infrequent, however, buprenorphine may also produce limited physical dependence, and signs and symptoms of mild withdrawal may appear following discontinuance of prolonged therapy with the drug alone. Due to buprenorphine's slow binding with the slow dissociation from the μ receptor, elimination of the drug from the CNS is prolonged following abrupt discontinuance; consequently, signs and symptoms of acute withdrawal are less intense than those produced by morphine and are delayed in appearance.

In patients physically dependent on opioids, buprenorphine produces many of the subjective and objective effects of opioids; however, the drug may not be a satisfactory substitute for opioid agonists in all patients physically dependent on opioids. Tolerance to the opioid agonist activity of the drug reportedly develops rarely, if at all.

Buprenorphine may produce psychological dependence. Buprenorphine is a partial opioid agonist with behavioral and psychic effects similar to morpholine. Unlike pentazocine, however, buprenorphine rarely causes psychotomimetic effects. Like other opioid agonists, buprenorphine may produce increases in cerebrospinal fluid pressure.

The pharmacokinetics of buprenorphine administered parenterally and sublingually are known. Intravenous administration of a single dose of about 0.3 mg of buprenorphine has been shown to provide mean peak plasma drug concentrations of about 18 ng/ml which occur within about 2 minutes; plasma concentrations declined to about 9 and about 0.4 ng/ml after about 5 minutes and about 3 hours, respectively. Following intramuscular administration of a second 0.3-mg dose 3 hours after the initial intravenous dose, mean peak plasma buprenorphine concentrations of about 3.6 ng/ml occur within about 2 to about 5 minutes and decline to about 0.4 ng/ml after about 3 hours. Approximately 10 minutes after administration, plasma concentrations of buprenorphine are similar following intravenous or intramuscular injection.

A parenteral solution of buprenorphine hydrochloride (0.3 mg buprenorphine/ml) is commercially available as Buprenex® (Reckitt & Colman) for intramuscular and intravenous administration. The usual adult dose (over age 13) is 0.3 mg IM or IV every 6 to 8 hours as needed for moderate to severe pain. The pediatric dose in patients age 2 to 12 is 2–6 mcg/kg of body weight every 4–6 hours. The increased frequency of administration in the pediatric population is believed to be caused by increased clearance of buprenorphine compared to the adult population. The mean duration of analgesia generally is six hours following single intramuscular or intravenous doses of 0.2 to 0.3 mg or 2 to 4 μg/kg; however, in some studies, the mean duration of analgesia reportedly range from 4 to 10 hours following single intramuscular doses of 0.2 to 0.6 mg and 2 to 24 hours following single intravenous doses of 0.3 mg or 2 to 15 μg/kg.

For reference, the mean peak plasma buprenorphine concentration, time to peak concentration, and systemic availability for a 0.4 mg and 0.8 mg single-dose sublingual dose of buprenorphine has been reportedly by Cowan, Alan and Lewis John, W., Buprenorphine; Combating Drug Abuse With a Unique Opioids, Wiley-Liss, Inc., New York, pp. 137–147 (1995), hereby incorporated by reference in its entirety. For a 0.4 mg sublingual dose, the Cmax was reported as 0.50±0.06 ng/ml; the Tmax was reported 210±40 minutes; and a systemic availability of 57.7%±6. For a 0.8 mg sublingual dose, the Cmax was reported as 1.04±1.27 ng/ml; the Tmax was reported 192±49 minutes; and a systemic availability of 54.1%±12.7.

It has previously been reported that a usual sublingual analgesic dose of buprenorphine is 0.2 to 0.4 mg every 8 ours (e.g., Kuhlman, J J et al. J Analyt Toxicol 1996; 20(10)). For transdermal patch watch might provide a nominal delivery rate of about 12.5 ug/hr, the total buprenorphine administered over a 24 our period would be about 0.3 mg, and the sublingual equivalent dose over the same period would be about 0.6 mg. For a transdermal delivery system (e.g., a transdermal patch) which might provide a nominal delivery rate of about 25 ug/hr, the total buprenorphine administered over a 24 hour period would be about 0.6 mg, and the sublingual equivalent dose over the same period would be about 1.2 mg. For a transdermal patch which might provide a nominal delivery rate of about 50 ug/hr, the total buprenorphine administered over a 24 hour period would be about 1.2 mg, and the sublingual equivalent dose over the same period would be about 2.4 mg. It is contemplated that one of ordinary skill in the art will appreciate that by simple pharmaceutical calculations, the equivalent doses for achieving the inventive buprenorphine plasma concentration set forth herein can be determined regardless of the mode of administration. In the present discussion, the comparison is made between transdermal dose and sublingual dose.

Distribution of buptenorphine into human body tissues ad fluids has not been well characterized. Following oral or intramuscular administration in rats, buprenorphine distributes into the liver, brain, placenta, and GI tract; highest concentrations were attained in the liver within 10 or 40 minutes following oral or intramuscular administration, respectively. The hepatic extraction ratio of buprenorphine is approximately 1. The drug and its metabolites are distributed into bile. Following intravenous administration in humans, the drug rapidly distributes into cerebro spinal fluid ("CSF") (within several minutes). CSF buprenorphine concentration appear to be approximately 15% to 25% of concurrent plasma concentrations. Buprenorphine is approximately 96% bound to plasma proteins, mainly to and β globulins; the drug does not appear to bind substantially to albumin.

Buprenorphine is almost completely metabolized in the liver, principally by N-dealkylation, to form norbuprenorphine (N-dealkylbuprenorphine); buprenorphine and norbuprenorphine also undergo conjugation with glucuronic acid. Like the metabolites of other opioid agonists, norbuprenorphine may have weak analgesic activity; however, studies to determine the analgesic activity of the metabolites of buprenorphine have not been performed. Buprenorphine and its metabolites are excreted principally in feces via biliary elimination and also in urine. Buprenorphine is excreted in feces mainly as unchanged drug; small amounts of norbuprenorphine are also excreted in feces. The drug and its metabolites are believed to undergo enterohepatic circulation. Norbuprenorphine appears to be excreted principally in urine at a slower rate than the parent drug. Total plasma clearance of buprenorphine reportedly is approximately 1.28 l/minute in conscious postoperative patients. Limited data indicate that there is considerable interindividual variability in buprenorphine pharmacokinetics in children; however, clearance of the drug appears to be increased in children (e.g., those 5 to 7 years of age) compared with that in adults. Optimal dosing interval of buprenorphine may have to be decreased in pediatric patients.

Achieving effective analgesic plasma opioid concentrations in patients is very complicated and involves a host of considerations, including the inherent chemical and physical properties of the opioid itself. Further considerations include in-vivo metabolism, individual patient response and tolerance. Generally, however, there is a "minimally effective analgesic concentration" (MEAC) in plasma for a particular opioid below which no analgesia is provided. There is relationship between plasma opioid levels and analgesia. Higher plasma levels are generally associated with greater pain relief, and (possibly) greater incidence and severity of side effects.

In preferred embodiments of the present invention where the patient(s) is being treated for moderate to severe pain, the buprenorphine is administered in a manner such that the following mean plasma concentrations are achieved over a 72 hour dosing interval: a mean plasma concentration from about 0.3 to about 113 pg/ml at about 6 hours after initiation of the dosing interval; a mean plasma concentration from about 3 to about 296 pg/ml at about 12 hours after initiation of the dosing interval; a mean plasma concentration from about 7 to about 644 pg/ml at about 24 hours after initiation of the dosing interval; a mean plasma concentration from about 13 to about 753 pg/ml at about 36 hours after initiation of the dosing interval; a mean plasma concentration from about 16 to about 984 pg/ml at about 48 hours after initiation of the dosing interval; a mean plasma concentration from about 20 to about 984 pg/ml at about 60 hours after initiation of the dosing interval; a mean plasma concentration from about 21 to about 1052 pg/ml at about 72 hours after initiation of the dosing interval. Thereafter, the buprenorphine is administered in a manner such that the mean plasma concentrations are maintained from about 19 to about 1052 pg/ml over at least the next 48 hours. In further preferred embodiments, this method further comprises maintaining the dosing of buprenorphine during the at least next 48 hours in accordance with zero order kinetics. Preferably, the mean plasma concentrations are maintained after the 72 hour dosing interval as follows: a mean plasma concentration from about 23 to about 1052 pg/ml at about 96 hours after initiation of the dosing interval; a mean plasma concentration from about 25 to about 1052 pg/ml at about 120 hours after initiation of the dosing interval; a mean plasma concentration from about 22 to about 970 pg/ml at about 144 hours after initiation of the dosing interval; and a mean plasma concentration form about 19 to about 841 pg/ml at about 168 hours after initiation of the dosing interval (for a seven day dosing interval). In this embodiment where a transde rmal delivery system is used, a mean relative release rate from about 3 ug/hr to about 86 ug/hr is preferably maintained from the initiation of the dosing interval until about 72 hours after the initiation of the dosing interval; and a mean relative release rate is preferably maintained from about 0.3 ug/hr to about 9 ug/hr from about 72 hours after the initiation of the dosing interval until the end of the dosing interval.

Preferably, the administration of buprenorphine is accomplished via a mode selected from the group consisting of transdermally, continuous infusion, and a mixture of transdermally and continuous infusion. Most preferably, the administration is accomplished by applying a transdermal delivery system to the skin of a patient, and maintaining said transdermal delivery system in contact with the patient's skin for at least 5 days.

In a further preferred embodiment of the invention, buprenorphine is administered to human patients in a manner such that the following mean plasma concentrations are achieved over a 72 hour dosing interval; a mean plasma concentration from about 1 to about 28 pg/ml at about 6 hours after initiation of the dosing interval; a mean plasma concentration from about 14 to about 74 pg/ml at about 12 hours after initiation of the dosing interval; a mean plasma concentration from about 30 to about 161 pg/mg at about 24 hours after initiation of the dosing interval; a mean plasma concentration from about 51 to about 188 pg/mg at about 36 hours after initiation of the dosing interval; a mean plasma concentration from about 62 to about 246 pg/ml at about 48 hours after incubation of the dosing interval; a mean plasma concentration from about 79 to about 246 pg/ml at about 60 hours after incubation of the dosing interval; a mean plasma concentration from about 85 to about 263 pg/ml at about 72 hours after initiation of the dosing interval. Thereafter, buprenorphine is administered in a manner such that the mean plasma concentrations are maintained from about 77 to about 263 pg/ml over at least the next 48 hours. Preferably, the plasma concentrations are maintained after the 72 hour dosing interval as follows: a mean plasma concentration from about 92 to about 263 g/ml at about 96 hours after initiating of the dosing interval; a mean plasma concentration from about 94 to about 263 pg/ml at about 120 hours after initiating of the dosing interval; a mean plasma concentration from about 86 to about 243 pg/ml at about 144 hours after initiation of the dosing interval; and a mean plasma concentration from about 77 to about 210 pg/ml at about 168 hours after initiation of the dosing interval (for a seven day dosing interval). In this embodiment wherein a transdermal delivery system is used, it is preferred that a mean relative release rate of from about 13 ug/hr to about 21 ug/hr is maintained from the initiation of the dosing interval until about 72 hours after the initiation of the dosing interval; and that a mean relative release rate of about 1 ug/hr to about 2 ug/hr from about 72 hours after the initiation of the dosing interval until the end of the dosing interval is maintained (e.g., to about 168 hours after initiation for a seven-day dosing interval).

In a further preferred embodiment of the invention, buprenorphine is administered to human patients in a manner such that the following mean plasma concentrations are achieved over a 72 hour dosing interval: a mean plasma concentration from about 0.3 to about 7 pg/ml at about 6 hours after initiation of the dosing interval; a mean plasma concentration from about 4 to about 19 pg/ml at about 12 hours after initiation of the dosing interval; a mean plasma concentration from about 7 to about 40 pg/ml at about 24 hours after initiation of the dosing interval; a mean plasma concentration from about 13 to about 47 pg/ml at about 36 hours after initiation of the dosing interval; a mean plasma concentration from about 16 to about 62 pg/ml at about 48 hours after initiation of the dosing interval; a mean plasma concentration from about 21 to about 62 pg/ml at about 60 hours after initiation of the dosing interval; a mean plasma concentration from about 20 to about 66 pg/ml at about 72 hours after initiation of the dosing interval. Thereafter, the buprenorphine is administered in a manner such that the mean plasma concentrations are maintained from about 19 to about 66 pg/ml over at least the next 48 hours. Preferably, the buprenorphine is administered in a manner such that the mean plasma concentrations are maintained as follows: a mean plasma concentration from about 23 to about 66 pg/ml at about 96 hours after initiation of the dosing interval; a mean plasma concentration from about 23 to about 66 pg/ml at about 120 hours after initiation of the dosing interval; a mean plasma concentration from about 22 to about 61 pg/ml at about 144 hours after initiation of the dosing interval; and a mean plasma concentration from about 19 to about 53 pg/ml at about 168 hours after initiation of the dosing interval (for a seven day dosing interval). In embodiments where a transdermal delivery system is used, a mean relative release rate is maintained from about 3 ug/hr to about 5 ug/hr from the initiation of the dosing interval until about 72 hours after the initiation of the dosing interval; and a mean relative release rate of about 0.3 ug/hr to about 0.6 ug/hr from about 72 hours after the initiation of the dosing interval until the end of the dosing interval (e.g., about 168 hours after initiation of a seven-day dosing interval).

In a further preferred embodiment of the invention, buprenorphine is administered to human patients in a manner such that the following mean plasma concentrations are achieved over a 72 hour dosing interval; a mean plasma concentration from about 0.7 to about 14 pg/ml at about 6 hours after initiation of the dosing interval; a mean plasma concentration from about 7 to about 37 pg/ml at about 12 hours after initiation of the dosing interval; a mean plasma concentration from about 15 to about 80 pg/ml at about 24 hours after initiation of the dosing material; a mean plasma concentration from about 25 to about 94 pg/ml at about 36 hours after initiation of the dosing interval; a mean plasma concentration from about 31 to about 123 pg/ml at about 48 hours after initiation of the dosing interval; a mean plasma concentration from about 40 to about 123 pg/ml at about 60 hours after initiation of the dosing interval; a mean plasma concentration from about 42 to about 132 pg/ml at about 72 hours after initiation of the dosing interval. Thereafter, the buprenorphine is administered in a manner such that the mean plasma concentrations are maintained from about 38 to about 132 pg/ml over at least the next 48 hours. Preferably, the buprenorphine is further administered in a manner such that the mean plasma concentrations are maintained as follows: a mean plasma concentration from about 46 to about 132 pg/ml at about 96 hours after initiation of the dosing interval; a mean plasma concentration from about 47 to about 132 pg/ml at about 120 hours after initiation of the dosing interval; a mean plasma concentration from about 43 to about 121 pg/ml at about 144 hours after initiation of the dosing interval; and a mean plasma concentration from about 38 to about 105 pg/ml at about 168 hours after initiation of the dosing interval (for a seven day dosing interval). In embodiments where a transdermal delivery system is used, a mean relative release rate from about 6 ug/hr to about 11 ug/hr is maintained from the initiation of the dosing interval until about 72 hours after the initiation of the dosing interval; and a mean relative release rate of about 0.7 ug/hr to about 1 ug/hr is maintained from about 72 hours after the initiation of the dosing interval until the end of the dosing interval (e.g., about 168 hours after initiation of a seven day dosing interval).

In a further preferred embodiment of the invention, buprenorphine is administered to human patients in a manner such that the following mean plasma concentrations are achieved over a 72 hour dosing interval; a mean plasma concentration from about 3 to about 57 pg/ml at about 6 hours after initiation of the dosing interval; a mean plasma concentration from about 28 to about 148 pg/ml at about 12 hours after initiation of the dosing interval; a mean plasma concentration from about 59 to about 322 pg/ml at about 24 hours after initiation of the dosing interval; a mean plasma concentration from about 102 to about 377 pg/ml at about 36 hours after initiation of the dosing interval; a mean plasma concentration from about 124 to about 492 pg/ml at about 48 hours after initiation of the dosing interval; a mean plasma concentration from about 159 to about 492 ml at about 60 hours; after initiation of the dosing interval; a mean plasma concentration from about 169 to about 526 pg/ml at about 72 hours after initiation of the dosing interval. Thereafter, the buprenorphine is administered in a manner such that the mean plasma concentrations are maintained from about 153 to about 526 pg/ml over at least the next 48 hours. Preferably, the buprenorphine is administered in a manner such that the mean plasma concentrations are maintained as follows: a mean plasma concentration from about 174 to about 526 pg/ml at about 96 hours after initiation of the dosing interval; a mean plasma concentration from about 187 to about 526 pg/ml at about 120 hours after initiation of the dosing interval; a mean plasma concentration from about 173 to about 485 pg/ml at about 144 hours after initiation of the dosing interval; a mean plasma concentration from about 153 to about 420 pg/ml at about 168 hours after initiation of the dosing interval (for a seven day dosing interval). In embodiments where a transdermal delivery system is used, a mean relative release rate from about 26 ug/hr to about 43 ug/hr is maintained from the initiation of the dosing interval until about 72 hours after the initiation of the dosing interval; and a mean relative release rate of about 2 ug/hr to about 4 ug/hr is maintained from about 72 hours after the initiation of the dosing interval until the end of the dosing interval (e.g., about 168 hours after initiation of a seven-day dosing interval).

In a further preferred embodiment of the invention, buprenorphine is administered to human patients in a manner such that the following mean plasma concentrations are achieved over a 72 hour dosing interval: a mean plasma concentration from about 4 to about 85 pg/ml at about 6 hours after initiation of the dosing interval; a mean plasma concentration from about 42 to about 222 pg/ml at about 12 hours after initiation of the dosing interval; a mean plasma concentration from about 89 to about 483 pg/ml at about 24 hours after initiation of the dosing interval; a mean plasma concentration from about 152 to about 565 pg/ml at about 36 hours after initiation of the dosing interval; a mean plasma concentration from about 186 to about 738 pg/ml at about 48 hours after initiation of the dosing interval; a mean plasma concentration from about 238 to about 738 pg/ml at 60 hours after initiation of the dosing interval; a means plasma concentration from about 254 to about 789 pg/ml at about 72 hours after initiation of the dosing interval. Thereafter, the buprenorphine is administered in a manner such that the mean plasma concentrations are maintained from about 230 to about 738 pg/ml over at least the next 48 hours. Preferably, the buprenorphine is administered in a manner such that the mean plasma concentrations are maintained as follows: a mean plasma concentration from about 276 to about 789 pg/ml at about 96 hours after initiation of the dosing interval; a mean plasma concentration from about 281 to about 789 pg/ml at about 120 hours after initiation of the dosing interval; a mean plasma concentration from about 259 to about 727 pg/ml at about 144 hours after initiation of the dosing interval; a mean plasma concentration from about 230 to about 630 pg/ml at about 168 hours a after initiation of the dosing interval (for a seven day dosing interval). In embodiments where a transdermal delivery system is used, a mean relative release rate of from about 38 ug/hr to about 64 ug/hr is maintained from the initiation of the dosing interval until about 72 hours after the initiation of the dosing interval; and a mean relative release rate of about 4 ug/hr to about 7 ug/hr is maintained from about 72 hours after the initiation of the dosing interval until the end of the dosing interval (e.g., about 168 hours after the initiation of a seven-day dosing interval).

In a further preferred embodiment of the invention, buprenorphine is administered to human patients in a manner such that the following mean plasma concentrations are achieved over a 72 hour dosing interval; a mean plasma concentration from about 5 to about 113 pg/ml at about 6 hours after initiation of the dosing interval; a mean plasma concentration from about 55 to about 296 pg/ml at about 12 hours after initiation of the dosing interval; a mean plasma concentration from about 118 to about 644 pg/ml at about 24 hours after initiation of the dosing interval; a mean plasma concentration from about 203 to about 753 pg/ml at about 36 hours after initiation of the dosing interval; a mean plasma concentration from about 247 to about 984 pg/ml at about 48 hours after initiation of the dosing interval; a mean plasma concentration from about 317 to about 984 pg/ml at about 60 hours after initiation of the dosing interval; a mean plasma concentration from about 339 to about 1052 pg/ml at about 72 hours after initiation of the dosing interval. Thereafter, the buprenorphine is administered in a manner such that the mean plasma concentrations are maintained from about 306 to about 1052 pg/ml over at least the next 48 hours. Preferably, the buprenorphine is administered in a manner such that the mean plasma concentrations are maintained as follows: a mean plasma concentration from about 369 to about 1052 pg/ml at about 96 hours after in initiation of the dosing interval; a mean plasma concentration from about 374 to about 1052 pg/ml at about 120 hours after initiation of the dosing interval; a mean plasma concentration from about 346 to about 970 pg/mil at about 144 hours after initiation of the dosing interval; a mean plasma concentration from about 306 to about 841 pg/ml at about 168 hours after initiation of the dosing interval (for a seven day dosing interval). In embodiments where a transdermal delivery system is used, a mean relative release rate of from about 51 ug/hr to about 86 ug/hr is maintained from the initiation of the dosing interval until about 72 hours after the initiation of the, e.g., dosing interval; and a mean relative release rate of about 5 ug/hr to about 9 ug/hr is maintained from about 72 hours after the initiation of the dosing interval until the end of the dosing interval, e.g., about 168 hours after the initiation of a seven-day dosing interval (e.g., about 168 hours after the initiation of a seven-day dosing internal).

In further embodiments of the invention, the method comprises the administration of buprenorphine transdermally to human patients according to very different relative release rates for the first 3 day portion of the dosing interval (indicative of substantially first order release), and the additional at least 2 day long portion of the dosing interval (substantially zero order release) such that mean relative release rates are achieved over the dosing interval as follows: a mean relative release rate of from about 3 ug/hr to about 86 ug/hr from the initiation of the dosing interval until about 72 hours after the initiation of the dosing interval; and a mean relative release rate of about 0.3 ug/hr to about 9 ug/hr from about 72 hours after the initiation of the dosing interval until the end of the dosing interval (e.g., about 168 hours after the initiation of a seven-day dosing interval).

In one preferred embodiment, the mean relative release rates achieved over the dosing interval are as follows: a mean relative release rate of from about 3 ug/hr to about 5 ug/hr from the initiation of the dosing interval until about 72 hours after the initiation of the dosing interval; and a mean relative release rate of about 0.3 ug/hr to about 0.6 ug/hr from about 72 hours after the initiation of the dosing interval until the end of the dosing interval (e.g., about 168 hours after initiation of a seven-day dosing interval).

In another preferred embodiment, the mean relative release rates achieved over the dosing interval are as follows: a mean relative release rate of from about 6 ug/hr to about 11 ug/hr from the initiation of the dosing interval until about 72 hours after the initiation of dosing interval; and a mean relative release rate of about 0.7 ug/hr to about 1 ur/hr from about 72 hours after the initiation of the dosing interval until the end of the dosing interval (e.g., about 168 hours after initiation of a seven-day dosing interval).

In another preferred embodiment, the mean relative release rates achieved over the dosing interval are as follows: a mean relative release rate of from about 13 ug/hr to about 21 ug/hr from the initiation of the dosing interval until about 72 hours after the initiation of the dosing interval; and a mean relative release rate of about 1 ug/hr to about 2 ug/hr from about 72 hours after the initiation of the dosing interval until the end of the dosing interval (e.g., about 168 hours after initiation of a seven-day dosing interval).

In yet another preferred embodiment, the mean relative release rates achieved over the dosing interval are as follows: a mean relative release rate of from about 26 ug/hr to about 43 ug/hr from the initiation of the dosing interval until about 72 hours after the initiation of the dosing interval; and a mean relative release rate of about 3 ug/hr to about 4 ug/hr from about 72 hours after the initiation of the dosing interval until the end of the dosing interval (e.g., about 168 hours after the initiation of a seven-day dosing interval).

In yet a further preferred embodiment, the mean relative release rates achieved over the dosing interval are as follows:

a mean relative release rate of from about 30 ug/hr to about 64 ug/hr from the initiation of the dosing interval until about 72 hours after the initiation of the dosing interval; and a mean relative release rate of about 4 ug/hr to about 7 ug/hr from about 72 hours after the initiation of the dosing interval until the end of the dosing interval (e.g., about 168 hours after the initiation of a seven-day dosing interval).

In yet a further preferred embodiment, the mean relative release rates achieved over the dosing interval are as follows: a mean relative release rate of from about 51 ug/hr to about 86 ug/hr from the initiation of the dosing interval until about 72 hours after the initiation of the dosing interval; and a mean relative release rate of about 5 ug/hr to about 9 ug/hr from about 72 hours after the initiation of the dosing interval until the end of the dosing interval, e.g., about 168 hours after the initiation of the dosing interval.

The method of the present invention may be accomplished by any mode of administration useful for buprenorphine known to those slilled in the art. However, certain modes of administration are more practical than others. Preferably, the mode of administration is via continuous infusion, through the oral mucosa, or most preferably, transdermally.

In embodiments of the invention where the plasma concentrations described herein are accomplished intravenous infusion, the pattern of plasma concentrations seen through time in this invention can be achieved by using the injectable, parenteral form of, e.g., buprenorphine hydrochloride suitably diluted in an intravenous infusion solution. The infusion rate would be controlled by a programmable infusion pump, to provide the desired plasma profile.

In preferred embodiments of the invention, the mode of administration of the buprenorphine is transdermal. Transdermal delivery of active agents is measured in terms of "relative release rate" or "flux", i.e., the rate of penetration of the active agent through the skin of an individual. Skin flux may be generally determined from the following equation:

$$dM/dt=J=P*C$$

where J is the skin flux, P is the permeability coefficient and C is the concentration gradient across the membrane, assumed to be the same as the donor concentration. M represents the cumulative amount of drug entering the blood stream. The variables dM and dt represent the change in cumulative amount of drug entering the blood stream and change in time, respectively.

It is well understood in the art of transdermal delivery systems that in order to maintain a desired flux rate for a desired dosing period, it is necessary to include an overage of active agent in the transdermal delivery system in an amount that is substantially greater than the amount to be delivered to the patient over the desired time period. For example, to maintain the desired flux rate for a three day time period, it is considered necessary to include much greater than 100% of a three day dose of an active agent in a transdermal delivery system. This overage is necessary for creating a concentration gradient by means of which the active agent migrates through the layers of the transdermal delivery system to the desired site on a patient's skin. The remainder of the active agent remains in the transdermal delivery system. It is only the portion of active agent that exits the transdermal delivery system that becomes available for absorption into the skin. The total amount of active agent absorbed into the patient's blood stream is less than the total amount available. The amount of overage to be included in a transdermal delivery system is dependent on these and other factors known to the skilled artisan.

[Surprisingly, it] *It* has been found that it is possible to treat pain according to the present invention by providing a transdermal delivery system containing a sufficient amount of opioid, e.g. buprenorphine, to provide a desired relative release rate for up to 3 days, and after single administration (application) of the transdermal dosage form, leaving the dosage form on the skin for approximately a 5 to 8 day time period, thereby resulting in the flux being maintained over the prolonged period and effective blood plasma levels and pain management being maintained over the prolonged period. Preferably, the desired flux is maintained at least about 5, preferably at least about 8 days after application of the transdermal delivery system. If the transdermal delivery system is removed 3 days after its administration, no analgesia is present a short time after removal. [Surprisingly however] *However*, if the same transdermal delivery system is maintained in contact with the skin for an about 5 to about 8 day period, analgesia is maintained over the prolonged period of contact, but the patient continues to experience analgesia. In other words, inclusion of the aforementioned overage of buprenorphine provides analgesia for at least about twice the expected 3 days dosing interval.

Any type of transdermal delivery system may be used in accordance with the methods of the present invention so long as the desired pharmacokinetic and pharmacodynamic response(s) are attained over at least 3 day s, e.g., from about 5 to about 8 days. Preferable transdermal delivery systems include e.g., transdermal patches, transdermal plasters, transdermal discs, iontophoretic transdermal devices and the like.

Transdermal dosage forms used in accordance with the invention preferably include a backing layer made of pharmaceutically acceptable material which is impermeable to the buprenorphine. The backing layer preferably serves as a protective cover for the active agent, e.g. buprenorphine and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof).

Preferred materials for inclusion in the polymer matrix layer are silicone elastomers of the general polydimethylsiloxane structures, (e.g., silicon polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxy silane.

Preferred transdermal delivery systems used in accordance with the methods of the present invention include an adhesive layer to affix the dosage form to the skin of the patient for a desired period of administration, e.g., about 5 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g, surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the buprenorphine into the blood stream of the patient. A non-limiting list of permeation enhancing agents includes polyethylene glycols, surfactants, and the like.

Alternatively, permeation of buprenorphine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of buprenorphine such as the use of iontophoretic means are also contemplated to be within the scope of the present invention.

A preferred transdermal dosage form which may be used in accordance with the present invention includes a non-permeable backing layer made, for example, of polyester, an adhesive layer made, for example of a polyacrylate; and a matrix containing the buprenorphine and other desirable pharm acetucial acids such as softeners, permeability enhancers, viscosity agents and the like.

The active agent may be included in the device in a drug reservoir, drug matrix or drug/adhesive layer. Preferably, the active agent is buprenorphine or a pharmaceutically acceptable salt thereof.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxyric acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, coeprylic acids glycerol and 1,2-propanediol which can also be etherified by polyethylene glycols.

A buprenorphine solvent may also be included in the transdermal delivery systems of the present invention. Preferably, the solvents dissolve the buprenorphine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the material used for the production of the backing layer described above provided that they are rendered removable, for example, by a silicone treatment. Other removable protective layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage form used in accordance with the invention and the type of device used are not considered critical to the method of the invention, provided that the device delivers the active agent, e.g. buprenorphine, for the desired time period and at the desired flux rate and/or the desired activity rate of the transdermal dosage form.

Certain preferred transdermal dosage forms for use in accordance with the present invention are described in U.S. Pat. No. 5,240,711 (Hille, et al.; assigned to LTS Lohmann Therapie-Systeme GmbH & Co.), hereby incorporated by reference. Such buprenorphine transdermal delivery systems may be a laminated composite having an impermeable backing layer containing buprenorphine, and optionally, a permeation enhancer combined with a pressure-sensitive adhesive. A preferred transdermal dosage form in accordance with the '711 patent includes: (i) a polyester backing layer which is impermeable to buprenorphine; (ii) a polyacrylate adhesive layer; (iii) a separating polyester layer; and (iv) a matrix containing buprenorphine, a solvent for the buprenorphine, a softener and a polyacrylate adhesive. The buprenorphine solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95%-wt polymeric material, about 0.1 to about 40%-wt softener, about 0.1 to about 30%-wt buprenorphine. A solvent for the buprenorphine base or pharmaceutically acceptable salt thereof may be included as about 0.1 to about 30%-wt.

In a preferred embodiment, the transdermal delivery system is prepared in accordance with Example 1 appended hereto. In this example, the transdermal delivery system was prepared in accordance with the disclosure of International Patent Application No. WO 96/19975 (Hille, et al.; assigned to LTS Lohmann Therapie-Systeme GMBH), hereby incorporated by reference. In this device, the buprenorphine transdermal delivery device contains resorption-promoting auxiliary substances. The resorption-promoting auxiliary substance forms an undercooled mass. The delivery system contains 10% buprenorphine base, 10–15% acid (such as levulinic acid), about 10% softener (such as oleyoleate); 55–70% polyacrylate; and 0–10% polyvinylpyrollidone (PVP).

In embodiments of the present invention wherein the buprenorphine plasma concentrations described herein are achieved via the use of a transdermal delivery device prepared in accordance with WO 96/19975, it is contemplated for example that the nominal delivery rate of buprenorphine from such patches will be, e.g., from about 12.5 to about 100 ug/hr. In certain preferred embodiments, in order to achieve a nominal delivery rate of 12.5 ug/hr, the total of buprenorphine included in the transdermal patch is about 5 mg, the active surface area is about 6.25 $cm^2$ and the patch size may be, e.g., about 19.4 $cm^2$. In certain preferred embodiments, in order to achieve a nominal delivery rate of 25 ug/hr, the total of buprenorphine included in the transdermal patch is about 10 mg, the active surface area is about 12.5 $cm^2$ and the patch size may be, e.g., about 30.6 $cm^2$. In certain preferred embodiments, in order to achieve a nominal delivery rate of 50 ug/hr, the total of buprenorphine included in the transdermal patch is about 20 mg, the active surface area is about 25 $cm^2$ and the patch size may be, e.g., about 51.8 $cm^2$. In certain preferred embodiments, in order to achieve a nominal delivery rate of 75 ug/hr, the total of buprenorphine included in the transdermal patch is about 30 mg, the active surface area is about 37.5 $cm^2$ and the patch size may be, e.g., about 69.8 $cm^2$. In certain preferred embodiments, in order to achieve a nominal delivery rate of 100 ug/hr, the total of buprenorphine included in the transdermal patch is about 40 mg, the active surface area is about 50 $cm^2$ and the patch size may be, e.g., about 87.8 $cm^2$.

[In accordance with a method of the invention, the] *The* above-described transdermal delivery system has been designed to be adhered to the patient for only three days and is expected to release analgetically effective doses of buprenorphine for only about 3 days. Instead, in accordance with the present invention, the transdermal delivery device is maintained in contact with the skin of the patient for a much longer time period, e.g., from about 5 to about 8 days, without any change in the formulation of the transdermal device itself. It has [surprisingly] been found that analgesia is maintained for this extended period of time (the time beyond the useful life designed for the transdermal formulation).

In other embodiments, the buprenorphine transdermal delivery system may be a plaster such as that described in U.S. Pat. No. 5,225,199 to Hidaka et al., hereby incorporated by reference. Such plasters include a film layer including a polyester film of about 0.5 to about 4.9 μm thickness, about 8 to about 85 g/mm strength, respectively in the two directions intersecting substantially at right angles, about 30 to about 150% elongation, in the two directions intersecting substantially at right angles and an elongation ratio of A to B of about 1.0 to about 5.0, wherein A and B represent data in two directions intersecting at right angles, and A is greater than B and wherein said polyester film includes about 0.01 to about 1.0% by weight, based on the total weight of the polyester film, of solid fine particles in which the average particle size is about 0.001 to about 3.0 μm and an adhesive layer which is composed of an adhesive containing transdermally absorbable drugs; wherein the adhesive layer is laminated on said film layer over the surface in about 2 to about 60 μm thickness. The average particle size is substantially not more than 1.5 times the thickness of the polyester film.

The transdermal delivery system used in the present invention may also be prepared in accordance with U.S. Pat. No. 5,069,909 (Sharma et al.), hereby incorporated by reference. This patent describes a laminated composite for administering buprenorphine transdermally to treat pain. The composite includes an impermeable backing layer providing a protective covering for the composite which may be made from an alastomeric polymer such as polyurethane, polyether amide, or copolyester and may be about 15–250 microns in thickness. The composite further includes a reservoir lamina composed of buprenorphine (base or HCl) in an amount of 1–12% by weight and a pressure-sensitive adhesive, e.g., polyisobutylene, or a silicone adhesive such as silastic, or an acrylate adhesive, and 2–35% permeation enhancer (comprising propylene glycol monolaurate in combination with capric acid or oleic acid). The amounts of buprenorphine and permeation enhancer are sufficient to cause the buprenorphine to pass through the skin at a rate of about 1 to 100 $kg/g^2/hr$.

The transdermal delivery system used in the present invention may also be prepared in accordance with U.S. Pat. No. 4,806,341 (Chien et al.), hereby incorporated by reference. This patent describes a transdermal morphinan narcotic analgesic or antagonist (including Buprenorphine) pharmaceutical polymer matrix dosage unit having a backing layer which is substantially impervious to the buprenorphine, and a polyester matrix disc layer which is adhered to the backing layer and which has microdispersed therein effective dosage amounts of the buprenorphine. The polymer matrix may be a silicon polymer or copolymer, such as methyl silicone polymer or copolymer, or methylvinyl silicone polymer or copolymer. The polymer matrix layer preferably has dispersed therein a skin permeation enhancing agent such as isopropyl myristate, azone, or a combination of ethyl caprylate and capryl alcohol.

The transdermal delivery system used in the present invention may also be that described in U.S. Patent No. 5,025,556 (Drust et al.), hereby incorporated by reference. Therein, compositions for the transdermal delivery of buprenorphine comprise buprenorphine in a carrier of a polar solvent material selected from the group consisting of $C_3$–$C_4$ diols, $C_3$–$C_6$ triols, and mixtures thereof, and a polar lipid material selected from the group consisting of fatty alcohol esters, fatty acid esters, and mixtures thereof; wherein the polar solvent material and the lipid material are present in a weight ratio of solvent material:lipid material of from 60:40 to about 99:1.

The transdermal delivery system used in the present invention may also be that described in U.S. Pat. No. 4,588,580 (Gale, et al.), hereby incorporated by reference. That system comprises a reservoir for the drug having a skin proximal, material releasing surface area in the range of about 5–100 $cm^2$ and containing between 0.1 and 50% by weight of a skin permeable form of the buprenorphine. The reservoir contains an aqueous gel comprising up to about 47–95% ethanol, 1–10% gelling agent, 0.1–10% buprenorphine, and release rate controlling means disposed in the flow path of the drug to the skin which limits the flux of the buprenorphine from the system through the skin. The release rate controlling means is more permeable to the buprenorphine than to the ethanol, and may be for example low density polyethylene (LDPE), ehtylene-vinyl acetate (EVA) copolymers, heat sealable polyesters, and elastomeric polyester block copolymers, such as HYTREL® from DuPont. This system is said to be capable of providing an administration rate of about 10–300% μg/hr. It is contemplated that each of the transdermal delivery systems described herein (other than the system exemplified in Example 1 appended hereto) would require minor manipulation i order to achieve the methods of the invention. Such modifications are within the abilities of one skilled in the art of formulating such transdermal delivery systems.

The present invention may also be accomplished via the use of a sustained oral muscosal delivery system. Such a system is described by McQuinn, R. L. et al., "Sustained Oral Mucosal Delivery in Human Volunteers J. Controlled Release; (34) 1995 (243–250). Therein, oral mucosal patches were prepared by homogeneously mixing buprenorphine free base (8%), Carbopol 934 (52%), polyisobutylene (35%) and polyisoprene (5%, w/w) via a two-roll mill and then compressing the mixtures to the appropriate thickness. A membrane backing (ethylcellulose) was applied to one side of the compressed material and then circular disks (0.5 $cm^2$) were purchased from the material. The backing was included in order to retard drug release from one side of the disk and to prohibit adhesion to opposing side tissues. Each soft, flexible disk was approximately 0.6 mm thick and contained 2.9 mg buprenorphine. These patches were worn by the subjects for 12 hours. Gum and lip application was tested, although adhesion at the gum site was considered superior. After the initial appearance of serum buprenorphine (≧25 pg/ml), levels generally increased relatively rapidly and persisted until the patch was removed. After the patch was removed, buprenorphine levels fell promptly and were at a relatively low (but measurable) level by 24 hours post-dose. It was estimated that 0.42±0.18 mg were delivered via the gum treatment. From this discussion, it is apparent that an oral mucosal patch can be prepared which will provide plasma concentrations considered desirable according to the present invention.

A significantly higher increase in side effects such as nausea, vomiting, or drowsiness would normally be expected when high blood levels of opioid analgesics are administered. The present invention, by maintaining a lower blood level of drug over the 7 day dosing period while maintaining effective pain management, has a lower incidence of side effects. In comparison, a much higher plasma concentration is seen in patients over the same period of time when a new transdermal delivery device of the same strength is put on every three days, and therefore increased side effects are expected with each new 3 day transdermal application.

[In general upon administration of an opioid analgesic, there is a lag time or "hysteresis", between the pharmacodynamic effects and the time course of opioid plasma concentration levels. Generally, peak plasma level concentrations are often attained prior to exhibition of the maximum pharmacotherapeutic or side effect response. It has been surprisingly discovered that the method according to the present invention provides a "reverse hysteresis," i.e. The rise in plasma concentrations follow the appearance and rise of certain of the pharmacodynamic events and side effects.]

DETAILED DESCRIPTION OF PREFERRED EMBODIMENTS

The following examples illustrative various aspects of the present invention. They are not to be construed to limit the claims in any manner whatsoever.

A seven day pharmacolkinetic/pharmacodynamic study was conducted on 24 healthy human patients. The subjects were comprised of approximately an equal number of male and female subjects. In this study, the buprenorphine was administered via a transdermal patch which is described in WO 96/19975.

The transdermal patch is prepared in accordance with the disclosure of WO 96/19975 for Example 1 therein as follows:

1.139 g of a 47.83 w/% polyacrylate solution with a self-netting acrylate copolymers containing 2-ethylhexylacrylates, vinyl acetates, acrylic acid (dissolving agent:ethylacetate:heptan:isopropanol:toluene:acetylacetonate in the ratio of 37:26:26:4:1), 100 g laevulinic acid, 150 g oleyloleate, 100 g polyvinylpyrollidone, 150 g ethanol, 200 g ethyl acetate and 100 g buprenorphine base are homogenized. The mixture is stirred for about 2 hours and then examined visually to determine if all solid substances have been dissolved. One has to control the evaporation loss by method of weighing back and makes up for the solvent with the help of ethylacetate, if necessary. Thereafter, the mixture is put onto a 420 mm wide, transparent polyester foil, since the surface weight of the dried layer of paste is 80 g per $m^2$. The polyester foil which can be dissolved again with treatment of silicone serves as a protective layer. The solvent is removed by drying with heated air which is led over a moist lane. With this treatment of warmth not only do solvents evaporate but the the laevulinic acid melts as well. Thereafter, the sealing films is covered with a polyester foil 15 μab. A surface of about 16 $cm^2$ is cut with the help of the appropriate cutting tool, and the rims that have been left between the individual systems are removed.

The formulation utilized in Example 1 is substantially the same as that described in Example 3 of WO 96/19975, which is preparing in accordance with Example 1 and is stated therein to include 10% buprenorphine, 10% levulinic acid, 10% polyvinylpyrollidone, 10% oleyloeate, and 60% polyacrylate.

In order to achieve the nominal delivery rate of 25 ug/hr expected for the formulation of Example 1, the total of buprenorphine included in the transdermal patch is about 10 mg, the active surface area is about 12.5 $cm^2$ and the patch size may be, e.g., about 30.6 $cm^2$.

The dosing regimen was one (1) patch containing 10 mg buprenorphine base/patch reservoir applied to the subject's skin and maintained in contact with the skin for a time period of seven (7) days.

The adhesive patch with the medication being tested was placed on the right midaxillary line at the level of the 5th intercostal space at approximately 0800 hr on day 1. For patch application, the skin was washed with lukewarm soapy water, then rinsed with clear water and left to air dry. The skin was not rubbed while it was being washed. The application site was relatively hairless. Hair was not clipped or shaven. The patches were removed by approximately 0800 hr on day 8. Following patch removal, the patch site was not washed or rubbed until the last blood collection for that treatment period was over. Each patch was placed unfolded onto its release liner and the patch/release liner unit was placed back in the correct pouch, which was then sent to a bioanalytical laboratory for residual buprenorphine assay.

Blood sampling (10 ml at each time point) started on day 1, and continued thereafter at the following times: 1 hr (pre-dose) and at regular intervals thereafter during the 7 day dosing interval.

Patch site skin observations of the patch sites were performed by the investigator/staff rating the quality of the skin at the site of the actual medication reservoir of the patch at 0 hr (prior to patch placement) and 30 minutes after patch removal. The rating scale was as follows:

Erythema: 0=No visible redness; 1=Very slight redness (just perceptible); 2=Slight but well-defined redness; 3=Moderately intense redness; 4=Severe erythema (dark red discoloration of the skin).

Edema: 0=No visible reactions; 1=Very mild edema (just perceptible); 2=Mild edema (corners of the area are well defined due to noticeable swelling); 3=Moderate edema (up to 1 mm swelling in diameter); 4=Severe edema (more than 1 mm swelling in diameter, protruding over the edges of the patch).

The following pharmacokinetic parameters were estimated: $AUC_{(o\text{-}last)}$ (pg.hr/ml)—the area under the curve from time zero to the time of last non-zero plasma buprenorphine concentration, calculated by the linear trapezoidal method: $C_{max}$ (pg/ml)—maximum observed plasma buprenorphine concentration over the dosing interval; if $C_{max}$ occurs at more than one time point, $T_{max}$ is defined as the time point for the first $C_{max}$; residual=buprenorphine remaining in used patches (mg/patch).

A summary of the plasma buprenorphine concentrations (provided in picograms per milliliter, or pg/ml), is set forth in Table 1 below:

TABLE 1

| HOURS[1] | MEAN[2] | STD. DEV.[3] | CV %[4] |
|---|---|---|---|
| 6 | 1.76 | 6.20 | 352.77 |
| 12 | 18.47 | 26.00 | 140.78 |
| 18 | 37.45 | 36.16 | 91.67 |
| 24 | 58.94 | 44.66 | 75.76 |
| 30 | 67.69 | 48.78 | 72.06 |
| 36 | 82.44 | 53.02 | 64.32 |
| 42 | 107.61 | 65.43 | 60.81 |
| 48 | 104.69 | 60.69 | 57.97 |
| 54 | 105.81 | 66.68 | 63.02 |
| 60 | 112.93 | 63.02 | 55.81 |
| 66 | 129.25 | 64.37 | 49.80 |
| 72 | 130.55 | 64.16 | 49.14 |
| 78 | 122.83 | 54.97 | 44.75 |
| 84 | 129.03 | 51.50 | 39.92 |
| 90 | 139.50 | 68.26 | 48.93 |
| 96 | 146.70 | 62.76 | 42.78 |
| 102 | 130.19 | 57.68 | 44.31 |
| 108 | 135.49 | 67.72 | 49.98 |
| 114 | 150.24 | 71.69 | 47.72 |
| 120 | 136.22 | 63.62 | 46.70 |
| 126 | 130.25 | 57.77 | 44.35 |
| 132 | 124.78 | 52.82 | 42.34 |
| 138 | 138.55 | 58.34 | 42.11 |
| 144 | 115.23 | 48.30 | 41.92 |
| 150 | 116.30 | 49.04 | 42.16 |
| 156 | 120.07 | 50.88 | 42.38 |
| 162 | 117.66 | 52.71 | 44.80 |
| 168 | 102.00 | 49.92 | 48.94 |

[1]hours after administration of close (e.g., application of patch)
[2]mean blood plasma concentration for the 24 test subjects (pg/ml)
[3]standard deviation of mean blood plasma concentrations
[4]coefficient of variation (%)

The mean plasma concentrations are further depicted in FIG. 1 (concentration pg/ml vs. time (days)). It is apparent from the pharmacokinetic results obtained with respect to Example 1 that the mean blood plasma concentrations rose steadily and peaked at about the 3-day time point during the dosing interval (e.g., about 72 hours after application of the patch), and thereafter [surprisingly] remained relatively steady throughout the remaining portion of the dosing interval (e.g., to about the 7-day time point, 168 hours after initiation of the dosing interval). Further, it is apparent from the buprenorphine plasma concentrations that first order kinetics were present during the first 72 hours of the dosing interval, and substantially zero order kinetics were present thereafter.

A summary of the pharmacokinetic parameters obtained for Example 1 are set forth in Table 2 below:

TABLE 2

| | MEAN | STD. DEV. | GEOMETRIC MEAN | CV % |
|---|---|---|---|---|
| AUC (0-168 hrs) | 17740.68 | 7503.50 | 16263.88 | 42.30 |
| Cmax (pg/ml) | 184.80 | 68.84 | 171.78 | 37.25 |
| Tmax (hrs) | 110.50 | 26.48 | | 23.96 |

The following pharmacodynamic parameters were assessed 5 minutes prior to each blood collection by having each patient respond to several questions by placing a vertical mark at the approximate spot on a 100 mm visual analog scale ("VAS") anchored on one end by "not at all" and on the other end by "an awful lot". The first question asked to the subjects was "Do you feel any effect of the drug"" After the patient marked his/her response on the VAS to this question, responses were obtained via the VAS as to whether the subjects had experienced (i) nausea, (ii) dizziness, and (iii) sleepiness. The results are set forth in Table 3. All pharmacodynamic parameters were sumrized and tabulated. Then a mixed (linear or nonlinear) effect was used to model the pharmacokinetic and pharmacodynamic relationships. The results concerning pharmacodynamic parameters (VAS) are set forth in FIG. 2.

TABLE 3

SUMMARY OF SEVERITY FOR THE MOST COMMONLY REPORTED (>=10% OF SUBJECTS) ADVERSE EVENTS (RELATED TO TREATMENT) (N = 24)

| | MILD | | MODERATE | | SEVERE | | TOTAL | |
|---|---|---|---|---|---|---|---|---|
| | N | (%) | N | (%) | N | (%) | N | (%) |
| CONSTIPATION | 3 | 12.5 | 0 | 0.0 | 0 | 0.0 | 3 | 12.5 |
| DIZZINESS | 8 | 33.3 | 0 | 0.0 | 0 | 0.0 | 8 | 33.3 |
| HEADACHE | 7 | 29.2 | 0 | 0.0 | 0 | 0.0 | 7 | 29.2 |
| NAUSEA | 6 | 25.0 | 0 | 0.0 | 0 | 0.0 | 6 | 25.0 |
| RASH | 20 | 83.3 | 0 | 0.0 | 0 | 0.0 | 20 | 83.3 |
| SOMNOLENCE | 11 | 45.8 | 0 | 0.0 | 0 | 0.0 | 11 | 45.8 |
| VOMITING | 2 | 8.3 | 1 | 4.2 | 0 | 0.0 | 3 | 12.5 |

As can be seen from the results set forth in Table 3, there was only one incident of a moderate adverse event, and no incidents of severe adverse events reported by the test subjects during the application interval. Further, turning to FIG. 2, it can be seen that the level of dizziness, nausea and sleepiness significantly decreased after day 3 of the dosage interval. Other side effects such as headache, vomiting and constipation were also low in occurrence.

Table 4 provides a summary of the amount of drug which was measured as remaining in the patches which were removed from the subjects after 7 days.

TABLE 4

| AMOUNT LEFT IN PATCH (mg) | |
|---|---|
| MEAN | 8.59 |
| SE | 0.11 |
| % RELEASED (ASSAY) | |
| MEAN | 14.02 |
| SE | 1.08 |

Comparative Examples A–C

A three (3) treatment, randomized, crossover study was conducted in normal volunteers. The treatments consisted of Comparative Example A (a single application buprenorphine transdermal delivery system); Comparative Example B (a single dose of buprenorphine administered intravenously) and Comparative Example C (3 sequential applications, every three days, of the buprenorphine transdermal delivery system used in Comparative Example A). A 10–14 day washout period intervened between the first dosing (application) day of each treatment. For the buprenorphine transdermal delivery system, the wash-out started when the third sequential patch was removed. This study was not analytically blinded due to analytical chemistry considerations and different sampling times.

The buprenorphine transdermal delivery system (patch) used in Comparative Examples A and C contained 250 mg buprenorphine base, and is prepared in accordance with Example 1. It was contemplated that the buprenorphine patch of Comparative Examples A and C would provide approximately double the dose and approximately double the relative release rate as compared to the buprenorphine patch of Example 1. For Comparative Examples A and C, it would be released from the patch per day, which is equivalent to an intravenous dose of 0.3 mg every 6 hours. The reference buprenorphine intravenous injection (Comparative Example B) was 0.3 mg (Temgesic®) Injectable 0.3 mg/ml, [1 ml/vial]).

In Comparative Example A, the buprenorphine transdermal delivery system (single dose) was adhered to a relatively hairless area of a subject's right thorax at the level of the fifth intercostal space in the midaxillary line at approximately 8 am on day 1 and removed at approximately 8 am on day 4. For Comparative Example A (buprenorphine transdermal delivery system single dose), blood sampling was conducted as follows: Day 1: 0, (buprenorphine transdermal delivery system adhered) 2, 3, 4, 6, 8, 10, 12, and 16 hr; Day 2: 0, 6, 12 hr; Day 3: 0, 12 hr; Day 4: 0 (prior to removal), 0.25, 0.5, 0.75, 1, 2, 3, 6, 12 hr post-removal; Day 5: 0, 12 hr; Day 6: 0, 12 hr; Day 7: 0 hr With respect to Comparative Example B, buprenorphine intravenous (IV) injection, 0.3 mg was infused over 2 minutes at approximately 8 am on day 1 through an in-dwelling cannula in the right anticubital vein. The buprenorphine intravenous 0.3 mg blood sampling was conducted as follows: Day 1: 0, 1, 2, 3, 5, 10, 15, 20, 25, 30, 45 minutes and 1, 1.5, 2, 3, 4, 5, 6, 10, 12, 24 hr; arterial blood sampling (left radial artery) for the first 4 hours; venous blood sampling from 2 hours post-dose to 24 hours post-dose. Therefore arterial and venous blood sampling occurred simultaneously 2, 3 and 4 hours post-dose.

With respect to Comparative Example C, the buprenorphine transdermal delivery system (3 sequential applications), was adhered to a relatively hairless area of a subject's right thorax at the level of the fifth intercostal space in the midaxillary line at approximately 8 am on day 1 and removed at approximately 8 am on day 4. The second buprenorphine transdermal delivery system 50 μg/hr was placed just adjacent to the first patch after the first was removed on day 4 at approximately 8 am and removed on day 7 at approximately 8 am. The third buprenorphine transdermal delivery system 50 μg/hr was placed just adjacent to the second patch but not in the same place as the first patch after the second patch is removed on day 7 at approximately 8 am and removed on day 10 at approximately 8 am. Blood samples for Comparative Example C, buprenorphine transdermal delivery system 3 sequential applications, were obtained as follows: Day 1: 0, (buprenorphine transdermal delivery system adhered), 2, 3, 4, 6, 8, 10, 12, and 16 hr; Day 2: 0, 6, 12 hr; Day 3: 0, 12 hr; Day 4: 0 (prior to removal), and 2, 3, 4, 6, 8, 10, 12, 16 hrs (after second buprenorphine transdermal delivery system adhered); Day 5: 0, 6, 12 hr; Day 6: 0, 12 hr; Day 7: 0 (prior to removal), and 2, 3, 4, 6, 8, 10, 12, 16 hrs (after third buprenorphine transdermal delivery system adhered); Day 8: 0, 6, 12 hr; Day 9: 0, 12 hr; Day 10: 0 (prior to buprenorphine transdermal delivery system removal), and 0.25, 0.5, 0.75, 1, 2, 3, 6, 12 hr (post-removal); the wash-out period started after patch removal on Day 10; Day 11: 0, 12 hr; Day 12: 0, 12 hr; and Day 13: 0.

The pharmacokinetic variables determined for Comparative Examples A–C were as follows:

$AUC_{(0\text{-}last)}$: pg-hr/ml—The area under the curve, as calculated by the linear trapezoidal method, up to the last observed value;

$AUC_{inf}$: pg-hr/ml—The area under the curve, calculated using the linear trapezoidal method;

$C_{max}$: pg/ml—Maximum measured plasma buprenorphine over the time span specified;

$T_{max}$: hrs—Time of the maximum measured plasma buprenorphine; when the maximum value occurs in more than one time point, $T_{max}$ is defined as the first time point with this value;

$T_{(1/2)c/m}$: The plasma half life of buprenorphine elimination, defined as $\ln 2/K_{clm}$, where $K_{clm}$ is the apparent first order elimination constant. The elimination rate constant was obtained from the slope of the terminal portion of the plasma-concentration time curved determined by regression analysis techniques;

$T_{(1/2)abs}$: The absorption half life of transdermal buprenorphine elimination, defined as $\ln 2/K_{abs}$, where $K_{abs}$ is the apparent first order absorption constant. Absorption rate was calculated only for the transdermal buprenorphine;

Cl: ml/min or 1/hr—Total clearance characterizes the clearing of the hypothetical plasma volume of drug per unit time;

$V_d$: 1 or 1 kg—Hypothetical volumes in which the drug is distributed in the body; and Absorption Rate: μg/hr—The rate at which buprenorphine enters the systemic circulation.

Plasma concentration data was analyzed using standard noncompartmental and compartmental techniques to derive pharmacokinetic parameters. In addition, various exploratory methods including fitting the intravenous data to pharmacokinetic models to determine which model best describes the data, and deconvolution analysis to determine the absorption rate was employed. Other parameters such as clearance, volumes of distribution, absorption rate, amount absorbed and bioavailability were determined by either standard noncompartmental or compartmental analysis or exploratory methods. The intravenous data was also analyzed utilizing compartmental modeling techniques.

A summary of plasma buprenorphine concentrations for Comparative Example A is provided in Table 5 below.

TABLE 5

| Comparative Example A | | | |
|---|---|---|---|
| HOUR | MEAN PLASMA CONC. (pg/ml) | STD. DEV | CV % |
| 2 | 2.04 | 5.87 | 287.10 |
| 3 | 7.96 | 16.28 | 204.47 |
| 4 | 14.84 | 18.63 | 125.51 |
| 6 | 23.49 | 25.81 | 109.85 |
| 8 | 42.34 | 37.91 | 89.52 |
| 10 | 72.03 | 71.36 | 99.07 |
| 12 | 85.96 | 68.69 | 79.90 |
| 16 | 133.89 | 103.43 | 77.25 |
| 24 | 175.58 | 120.17 | 68.44 |
| 30 | 169.15 | 108.65 | 64.23 |
| 36 | 200.16 | 134.45 | 67.17 |
| 48 | 251.10 | 156.66 | 62.39 |
| 60 | 250.11 | 125.01 | 49.98 |
| 72 | 286.50 | 131.58 | 45.92 |
| 78 | 168.73 | 61.26 | 36.30 |
| 84 | 114.68 | 52.72 | 45.97 |
| 96 | 90.75 | 39.12 | 43.11 |
| 108 | 56.82 | 25.66 | 45.17 |
| 120 | 44.85 | 23.80 | 53.06 |
| 132 | 30.40 | 21.87 | 71.95 |
| 144 | 29.14 | 20.27 | 69.58 |

A summary of plasma buprenorphine concentration (pg/ml) for Comparative Example C at each sampling time is set forth in Table 6 below:

TABLE 6

| Comparative Example C | | | |
|---|---|---|---|
| HOUR | MEAN PLASMA CONC. (pg/ml) | STD. DEV | CV % |
| 2 | 0.54 | 2.63 | 489.90 |
| 3 | 5.70 | 13.18 | 231.23 |
| 4 | 10.33 | 14.64 | 141.71 |
| 6 | 28.84 | 31.19 | 108.31 |
| 8 | 54.62 | 65.83 | 120.52 |
| 10 | 78.92 | 81.23 | 102.93 |
| 12 | 95.14 | 75.70 | 79.57 |
| 16 | 162.26 | 114.80 | 70.75 |
| 24 | 218.57 | 153.58 | 70.27 |
| 30 | 206.10 | 141.70 | 68.75 |
| 36 | 205.08 | 110.76 | 54.01 |
| 48 | 265.04 | 123.66 | 46.66 |
| 60 | 256.18 | 133.48 | 52.11 |
| 72 | 306.02 | 152.77 | 49.92 |
| 74 | 278.22 | 135.14 | 48.57 |
| 75 | 245.91 | 112.66 | 45.82 |
| 76 | 237.01 | 83.41 | 35.19 |
| 78 | 213.54 | 94.42 | 44.22 |
| 80 | 215.45 | 103.75 | 48.15 |
| 82 | 216.00 | 107.68 | 49.85 |
| 84 | 210.52 | 107.67 | 51.14 |
| 88 | 219.77 | 110.46 | 50.26 |
| 96 | 269.91 | 134.61 | 49.87 |
| 102 | 205.54 | 102.03 | 49.64 |
| 108 | 225.11 | 87.97 | 39.08 |
| 120 | 310.27 | 153.57 | 49.50 |
| 132 | 300.34 | 157.05 | 52.29 |
| 144 | 305.99 | 159.75 | 52.21 |
| 146 | 301.39 | 141.37 | 46.91 |
| 147 | 289.96 | 132.91 | 45.84 |
| 148 | 287.68 | 151.93 | 52.81 |
| 150 | 260.04 | 130.19 | 50.07 |
| 152 | 236.61 | 119.77 | 50.62 |
| 154 | 284.15 | 158.84 | 55.90 |

TABLE 6-continued

| Comparative Example C | | | |
|---|---|---|---|
| HOUR | MEAN PLASMA CONC. (pg/ml) | STD. DEV | CV % |
| 156 | 271.83 | 145.11 | 53.38 |
| 160 | 303.46 | 182.37 | 60.10 |
| 168 | 340.71 | 209.87 | 61.60 |
| 174 | 302.22 | 179.74 | 59.47 |
| 180 | 322.67 | 183.63 | 56.91 |
| 192 | 395.95 | 220.27 | 55.63 |
| 204 | 344.83 | 201.90 | 58.55 |
| 216 | 415.33 | 229.92 | 55.36 |
| 216.25 | 388.64 | 186.67 | 43.03 |
| 216.50 | 390.97 | 208.34 | 53.29 |
| 216.75 | 392.63 | 188.89 | 48.11 |
| 217 | 399.51 | 197.86 | 49.53 |
| 218 | 312.65 | 173.12 | 55.37 |
| 219 | 295.17 | 148.13 | 50.18 |
| 222 | 201.37 | 85.54 | 42.48 |
| 228 | 173.89 | 75.96 | 43.68 |
| 240 | 119.13 | 48.99 | 41.13 |
| 252 | 84.21 | 49.61 | 58.91 |
| 264 | 72.33 | 37.86 | 52.42 |
| 276 | 50.18 | 25.83 | 51.47 |
| 288 | 43.06 | 26.61 | 61.79 |

A summary of mean plasma buprenorphine concentrations (pg/ml) at each sampling time for Comparative Example B (buprenorphine intravenous 0.3 mg single dose) is provided in Table 7 below:

TABLE 7

| Comparative Example B | | | |
|---|---|---|---|
| HOUR | MEAN PLASMA CONC. (pg/ml) | STD. DEV | CV % |
| 0.02 | 14812.04 | 11319.10 | 76.42 |
| 0.03 | 31052.04 | 16156.81 | 52.03 |
| 0.05 | 24547.00 | 16461.86 | 67.06 |
| 0.08 | 6418.80 | 1976.26 | 30.79 |
| 0.17 | 3360.76 | 2457.58 | 73.13 |
| 0.25 | 1747.96 | 465.81 | 26.65 |
| 0.33 | 1210.08 | 219.28 | 18.12 |
| 0.42 | 1050.00 | 242.10 | 23.06 |
| 0.50 | 931.52 | 207.25 | 22.25 |
| 0.75 | 692.92 | 175.29 | 25.30 |
| 1.00 | 584.40 | 148.93 | 25.48 |
| 1.50 | 457.44 | 131.44 | 28.73 |
| 2.00 | 335.12 | 79.36 | 23.68 |
| 3.00 | 238.80 | 63.03 | 26.39 |
| 4.00 | 170.87 | 49.84 | 29.17 |

A summary of the mean maximum concentration (Cmax) for Comparative Examples A–C measured in pg/ml is set forth in Table 8 below:

TABLE 8

| $C_{max}$ Values for Comparative Examples A-C | | | |
|---|---|---|---|
| | Comparative Example A | Comparative Example C | Cmax (pg/ml) · Comparative Example B |
| Mean | 318.20 | 477.33 | 38635.56 |
| Std. Dev. | 151.24 | 216.92 | 14499.55 |
| Geometric Mean | 291.13 | 435.50 | 35251.92 |
| CV % | 47.53 | 45.44 | 37.53 |

A summary of mean Tmax values obtained for Comparative Examples A–C is set forth in Table 9 below:

TABLE 9

| | Tmax Prior to Patch Removal (hrs) | | Tmax (hrs) |
|---|---|---|---|
| | Comparative Example A | Comparative Example C | Comparative Example B |
| Mean | 61.92 (out of72hrstotal) | 168.39 (out of260hrstotal) | 0.04 |
| Std. Dev. | 13.27 | 42.68 | 0.01 |
| CV % | 21.43 | 25.35 | 26.26 |

Table 10 provides a summary of the area under the curve (AUC) (0-t) for Comparative Examples A–C:

TABLE 10

| | Comparative Example A | Comparative Example C | Comparative Example B |
|---|---|---|---|
| Mean | 18,829.13 | 65,217.25 | 3,699.91 |
| Std. Dev. | 9,136.12 | 31,124.37 | 526.64 |
| Geometric Mean | 16,760.39 | 57,794.90 | 3,666.65 |
| CV % | 48.52 | 47.72 | 14.23 |

The pharmacodynamics were determined via VAS "drug effect" observations. The subject was asked "do you feel any of the drug?". the subject then rated the item by placing a vertical mark along a 100 mm visual analog scale (VAS) anchored on one end by "not at all" and on the other end by "an awful lot". The "drug effect" question was assessed just prior to each blood sample during the study. The following adverse effects were elicited just prior to blood sampling using the VAS: nausea; dizziness; and sleepiness. Asymmetric blood sampling was used in this study due to the number of sampling times.

Figure 3:
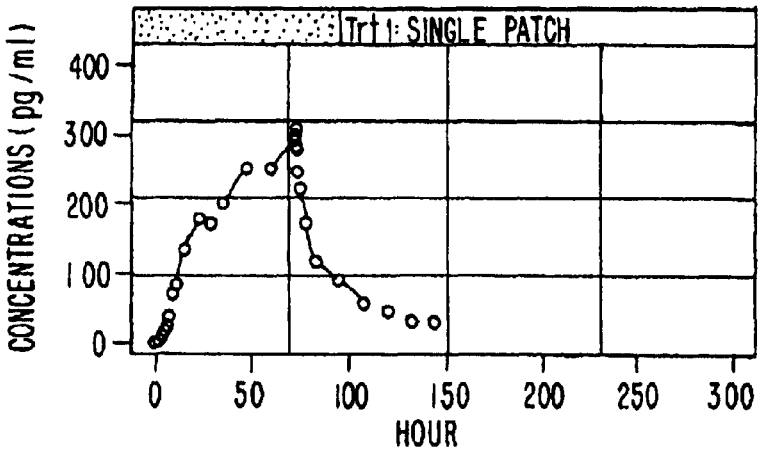
FIG. 3 is a graphical representation of the plasma concentration (pg/ml) over time (hours) for Comparative Example A.
Figure 4:
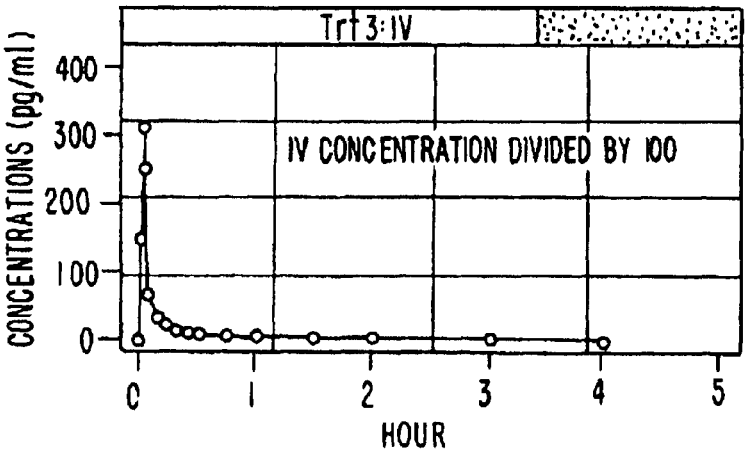
FIG. 4 is a graphical representation of the plasma concentration (pg/ml) over time (hours) for Comparative Example B (intravenous concentrations divided by 100)
Figure 5:
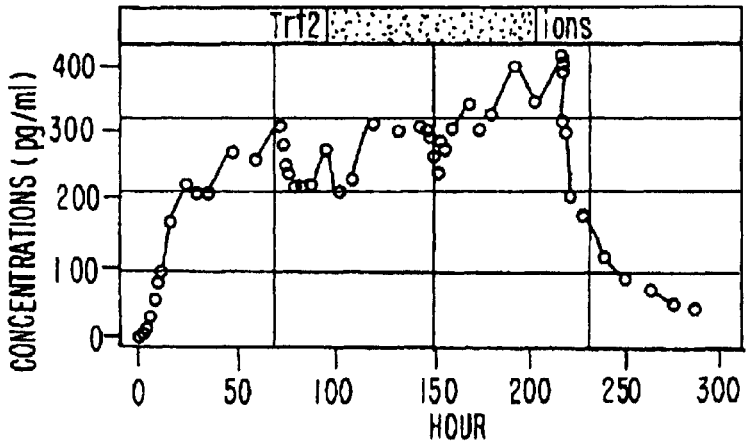
FIG. 5 is a graphical representation of the plasma concentration (pg/ml) over time (hours) for Comparative Example C.
Figure 6:
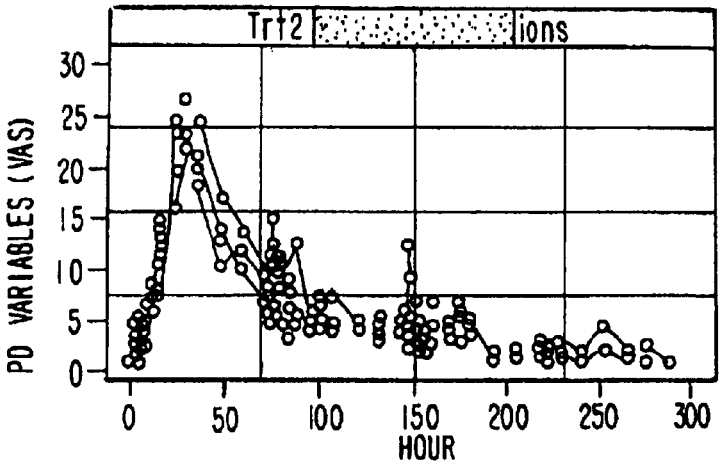
FIG. 6 is a graphical representation pharmacodynamic variables versus time (hours) for Comparative Example A.
Figure 7:
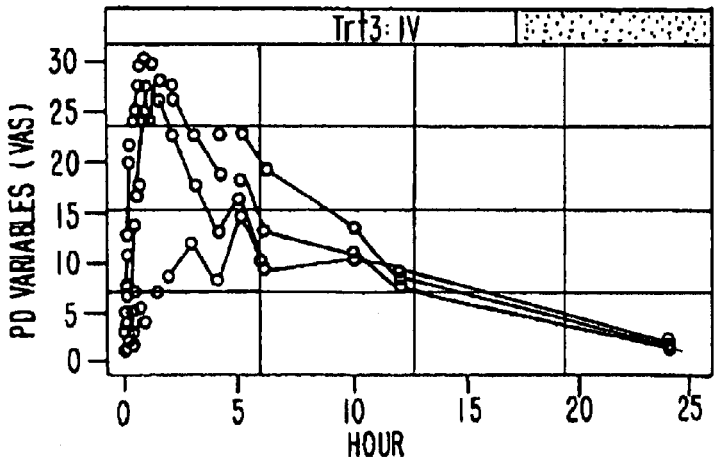
FIG. 7 is a graphical representation pharmacodynamic variables versus time (hours) for Comparative Example B.
Figure 8:
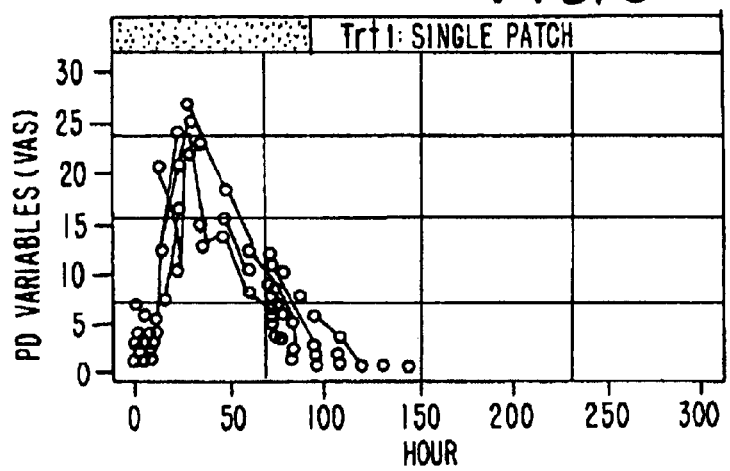
FIG. 8 is a graphical representation pharmacodynamic variables versus time (hours) for Comparative Example C.

The pharmacokinetic results (concentration in pg/ml vs. hours) for Comparative Examples A–C are depicted in FIGS. 3–5, respectively. FIG. 4 depicts the plasma concentration obtained divided by 100. The pharmacodynamic results (PD variables (VAS)) for Comparative Examples [A–C] *C, B, A* are depicted in FIGS. [6–8] *6, 7, 8*, respectively.

Comparative Examples D–F

The bioequivalence between a buprenorphine transdermal delivery system in accordance with Example 1 is compared to identically prepared patches having different sizes and therefore different amounts of buprenorphine contained therein.

Comparative Example D utilizing a patch identical in size and contaiing the same amount of buprenorphine as Example 1. The total of buprenorphine included in the transdel patch is 10 mg, the active surface area is 12.5 $cm^2$ and the patch size is 30.6 $cm^2$. In Comparative Example E, two patches are utilized, each patch including total of buprenorphine of about 5 mg, and having an active surface area of 6.25 $cm^2$ and a patch size of 19.4 $cm^2$. Comparative Example F allows for the determination area of the dose proportionality of a buprenorphine transdermal delivery system (patch) having twice the dose as compared to Example 1. In Comparative Example F, the total of buprenorphine include in the transdermal patch is 20 mg, the active surface area is 25 $cm^2$ and the patch size is 51.8 $cm^2$. The study was conducted via a 3-way cross-over design. The patches were left in place for 72 hours and then removed.

Table 11 provides a summary of mean plasma buprenorphine concentrations (pg/ml) at each sampling time for Comparative Example D:

TABLE 11

| HOURS | MEAN PLASMA CONC. (pg/ml) | STD. DEV. | CV % |
|---|---|---|---|
| 3 | 1.92 | 8.82 | 458.26 |
| 6 | 22.69 | 30.98 | 136.54 |
| 9 | 38.54 | 48.79 | 126.62 |
| 12 | 59.22 | 62.92 | 106.24 |
| 16 | 89.85 | 78.93 | 87.84 |
| 24 | 128.70 | 72.79 | 56.55 |
| 30 | 125.99 | 84.68 | 67.21 |
| 36 | 143.07 | 78.40 | 54.80 |
| 48 | 196.72 | 101.50 | 51.59 |
| 60 | 182.72 | 82.61 | 45.21 |
| 72 | 169.95 | 65.04 | 38.27 |
| 84 | 122.19 | 41.69 | 34.12 |
| 96 | 83.30 | 35.56 | 42.69 |
| 108 | 55.09 | 30.82 | 55.94 |
| 120 | 41.63 | 20.74 | 49.82 |
| 132 | 27.14 | 25.47 | 93.84 |
| 144 | 17.54 | 20.09 | 114.51 |

Table 12 provides a summary of the pharmacokinetic parameters for Comparative Example D:

TABLE 12

| PARAMETER | ARITHMETIC MEAN (SE) | GEOMETRIC MEAN (SE) |
|---|---|---|
| AUC (0-Infinity) | 16278.05 (1246.6) | 15255.84 (1272.5) |
| AUC (0-Last) | 14446.10 (1292.0) | 13162.96 (1340.6) |
| Cmax (pg/ml) | 229.87 (19.29) | 214.47 (17.92) |
| T ½ Elim. (hrs) | 30.53 (2.80) | |
| Tmax (hrs) | 67.02 (3.14) | |

Table 13 provides a summary of means plasma buprenorphine concentrations for Comparative Example E:

TABLE 13

| HOURS | MEAN PLASMA CONC. (pg/ml) | STD. DEV. | CV % |
|---|---|---|---|
| 3 | 1.63 | 7.29 | 447.21 |
| 6 | 19.61 | 33.28 | 169.70 |
| 9 | 29.09 | 44.04 | 151.40 |
| 12 | 44.43 | 56.91 | 128.09 |
| 16 | 59.77 | 66.25 | 110.86 |
| 24 | 110.49 | 98.86 | 89.48 |
| 30 | 107.58 | 86.83 | 80.71 |
| 36 | 116.36 | 83.01 | 71.34 |
| 48 | 154.35 | 83.40 | 54.03 |
| 60 | 151.22 | 90.70 | 59.98 |
| 72 | 145.20 | 62.84 | 43.28 |
| 84 | 106.91 | 38.86 | 36.35 |
| 96 | 82.61 | 64.87 | 42.21 |
| 108 | 44.83 | 26.74 | 59.65 |
| 120 | 29.68 | 24.26 | 81.73 |
| 132 | 22.52 | 24.42 | 108.44 |
| 144 | 9.24 | 17.28 | 186.93 |

Table 14 provides a summary of the pharmacokinetic parameters for Comparative Example E:

TABLE 14

| PARAMETER | ARITHMETIC MEAN (SE) | GEOMETRIC MEAN (SE) |
|---|---|---|
| AUC (0-Infinity) | 13450.96 (1326.8) | 12315.56 (1142.0) |
| AUC (0-Last) | 12026.65 (1318.7) | 10796.23 (1110.3) |

TABLE 14-continued

| PARAMETER | ARITHMETIC MEAN (SE) | GEOMETRIC MEAN (SE) |
|---|---|---|
| Cmax (pg/ml) | 199.10 (17.50) | 186.49 (14.69) |
| T ½ Elim. (hrs) | 25.82 (1.51) | |
| Tmax (hrs) | 68.26 (3.18) | |

Table 15 provides a summary of mean plasma buprenorphine concentrations for Comparative Example F:

TABLE 15

| HOURS | MEAN PLASMA CONC. (pg/ml) | STD. DEV. | CV % |
|---|---|---|---|
| 3 | 5.23 | 13.21 | 252.44 |
| 6 | 34.49 | 55.11 | 159.80 |
| 9 | 58.67 | 91.17 | 155.40 |
| 12 | 94.52 | 111.07 | 117.51 |
| 16 | 137.07 | 118.65 | 86.56 |
| 24 | 195.58 | 148.53 | 75.94 |
| 30 | 201.51 | 142.24 | 70.59 |
| 36 | 229.52 | 154.25 | 67.20 |
| 48 | 283.35 | 124.06 | 43.78 |
| 60 | 314.17 | 173.81 | 55.32 |
| 72 | 306.60 | 124.57 | 40.63 |
| 84 | 209.66 | 62.84 | 29.97 |
| 96 | 143.30 | 43.88 | 30.62 |
| 108 | 113.53 | 70.33 | 61.95 |
| 120 | 78.71 | 37.46 | 47.59 |
| 132 | 75.29 | 47.92 | 63.64 |
| 144 | 44.45 | 32.26 | 72.57 |

Table 16 provides a summary of the dose-corrected pharmacoldnetic parameters for Comparative Example F. The values are calculated based on a Cmax value which is one-half the actual reported value:

TABLE 16

| PARAMETER | ARITHMETIC MEAN (SE) | GEOMETRIC MEAN (SE) |
|---|---|---|
| AUC (0-Infinity) | 14761.59 (1469.7) | 13540.78 (1228.3) |
| AUC (0-Last) | 12558.04 (1313.9) | 11456.76 (1067.0) |
| Cmax (pg/ml) | 191.84 (16.93) | 179.60 (14.23) |
| T ½ Elim. (hrs) | 26.59 (1.52) | |
| Tmax (hrs) | 72.37 (1.89) | |

Table 17 provides a summary of the buprenorphine patch residuals for each of Comparative Examples D–F:

TABLE 17

SUMMARY OF BUPRENORPHINE PATCH RESIDUALS

| | Ex. D | Ex. F | Ex. E |
|---|---|---|---|
| AMOUNT LEFT IN PATCH (mg) | | | |
| N | 27 | 27 | 52 |
| MEAN | 8.76 | 18.31 | 4.75 |
| SE | 0.07 | 0.15 | 0.03 |
| % RELEASED (ASSAY) | | | |
| N | 27 | 27 | 52 |
| MEAN | 12.31 | 10.84 | 8.43 |
| SE | 0.67 | 0.73 | 0.53 |

Figure 9:
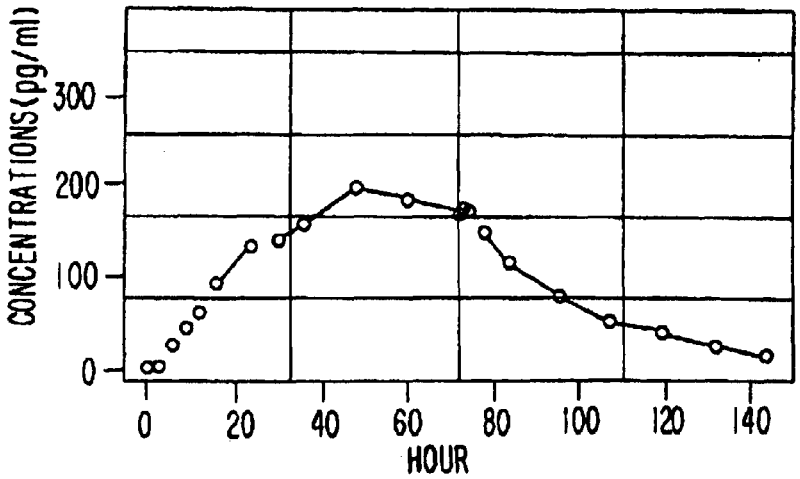
FIG. 9 is a graphical representation of the plasma concentration (pg/ml) over time (hours) for Comparative Example D.
Figure 10:
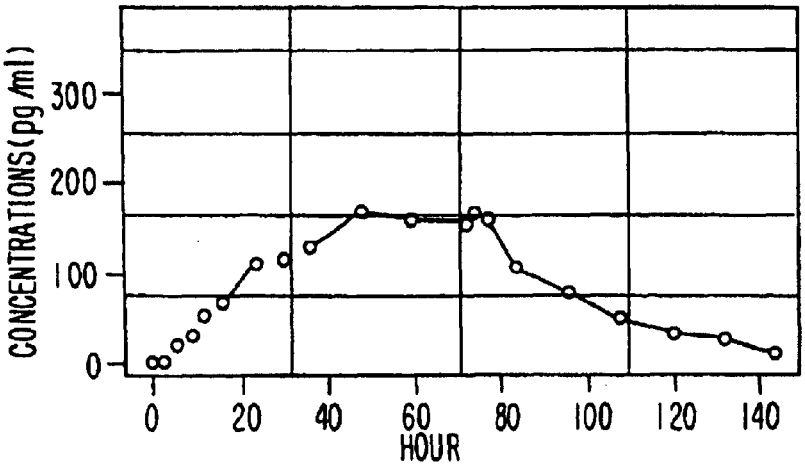
FIG. 10 is a graphical representation of the plasma concentration (pg/ml) over time (hours) for Comparative Example E.
Figure 11:
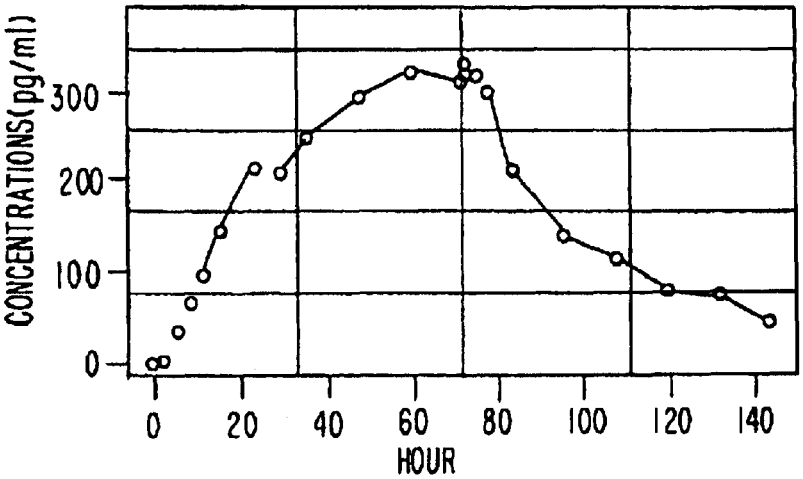
FIG. 11 is a graphical representation of the plasma concentration (pg/ml) over time (hours) for Comparative Example F.
Figure 12:
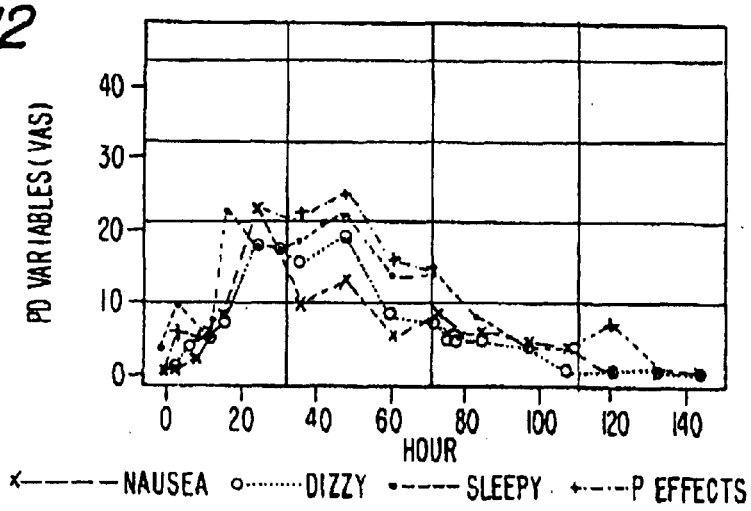
FIG. 12 is a graphical representation pharmacodynamic variables versus time (hours) for Comparative Example D.
Figure 13:
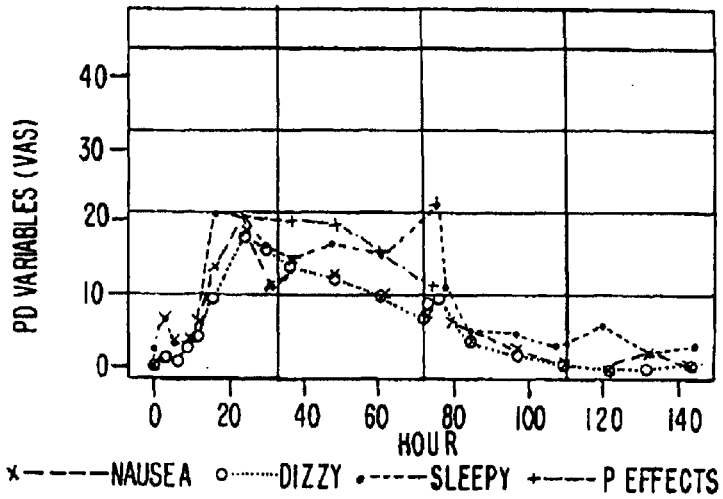
FIG. 13 is a graphical representation pharmacodynamic variables versus time (hours) for Comparative Example E.
Figure 14:
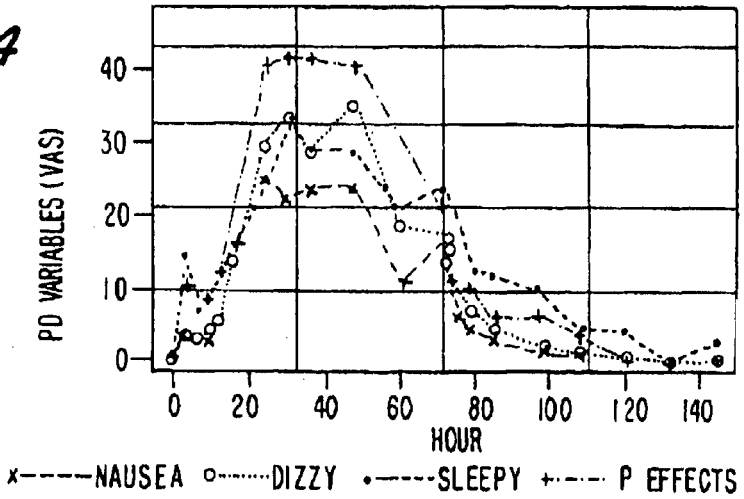
FIG. 14 is a graphical representation pharmacodynamic variables versus time (hours) for Comparative Example F.

The pharmacokinetic results (concentration in pg/ml vs. hours) for Comparative Examples D–F are depicted in FIGS. 9–11, respectively. The pharmacodynamic results (PD variables (VAS)) for Comparative Examples [A–C] *D–F* are depicted in FIGS. 12–14, respectively.

Conclusions

In order to readily consider the results obtained comparing the method of the present invention to the Comparative Examples, the following tables are provided.

Table 18 provides a direct comparison of the plasma concentrations obtained from Example 1 (a 10 mg buprenorphine patch maintained in contact with the subject's skin for 7 days) to Comparative Example A (20 mg buprenorphine patch left on the subjects' skin for only 3 days, then removed) to Comparative Example C (three sequential applications of a 20 mg buprenorphine patch left on the subjects' skin for only 3 days, then removed). In order to compare the plasma concentrations, the plasma concentrations of Comparative Examples A and C are also presented at 50% concentrations for each time interval:

TABLE 18

COMPARISON OF PLASMA CONCENTRATIONS

| HOUR/ (DAY) | Ex. 1 MEAN | COMPARATIVE EXAMPLE C MEAN | COMPARATIVE EXAMPLE C MEAN (½ DOSE) | COMPARATIVE EXAMPLE A MEAN | COMPARATIVE EXAMPLE A MEAN (½ DOSE) |
|---|---|---|---|---|---|
| 24 (1) | 58.94 | 218.57 | 109.29 | 175.58 | 87.79 |
| 48 (2) | 104.69 | 265.04 | 132.52 | 251.10 | 125.55 |
| 72 (3) | 130.55 | 306.02 | 153.01 | 286.50 | 143.25 |
| 96 (4) | 146.70 | 269.91 | 134.96 | 90.75 | 45.38 |
| 120 (5) | 136.22 | 310.27 | 155.14 | 44.85 | 22.43 |
| 144 (6) | 115.23 | 305.99 | 153.00 | 29.14 | 14.57 |
| 168 (7) | 102.00 | 340.71 | 170.36 | | |
| 192 (8) | | 395.95 | 197.98 | | |

The data presented in Table 18 shows that [, surprisingly,] plasma levels effective to provide analgesia were present in Example 1 (patch remained on skin for 7 days) even 7 days after application of the patch; whereas in Comparative Example A (patch removed after 3 days), blood levels fell dramatically once the patch was removed, such that plasma levels which would be indicative of ineffective treatment for the dosage of buprenorphine occurred not long after patch removal. On the other hand, turning to Comparative Example C, it is apparent that the plasma levels obtained from 3-day sequential administration of the buprenorphine patch resulted in significant increases in Cmax levels during each day dosing interval. This fact is confirmed by the graph of plasma concentration over time for Comparative Example C provided in FIG. 3. In contrast, the plasma level for Example 1 remained substantially level over the time-frame of 72 hours–168 hours after patch application. [The results indicate that the method of the present invention has the surprising benefit of reducing plasma concentrations of buprenorphine required to allow patients to experience effective analgesia.] Furthermore, comparing the VAS results graphically depicted for Example 1 to Comparative Example C, it is apparent that side effects were significantly reduced according to the method of Example 1, during the 7-day dosage interval. Further benefits are obtained from the invention respect to modes of administration other than [trasdermally] *transdermally* where the large plasma concentration peaks obtained in the prior art, e.g., through intravenous dosing, can be avoided. For example, in Comparative Example B, a Cmax in excess of about 30,000 pg/ml was obtained.

Table 19 provides a direct comparison of the plasma concentrations of Example 1 (a 10 mg buprenorphine patch maintained in contact with the subjects' skin for 7 days) to Comparative Example D (same 10 mg buprenorphine patch left on the subjects' skin for only 3 days, then removed) to Comparative Example E (two 5 mg buprenorphine patches left on the subjects' skin for 3 days, then removed):

TABLE 19

COMPARISON OF PLASMA CONCENTRATIONS (PG/ML)

| Hours (Post-Application) | Ex. 1 MEAN CONC. | Ex. D MEAN CONC. | Ex. E MEAN CONC. |
|---|---|---|---|
| 3 | | 1.92 | 1.63 |
| 6 | 1.76 | 22.69 | 19.61 |
| 9 | | 38.54 | 29.09 |
| 12 | 18.47 | 59.22 | 44.43 |
| 16 | | 89.85 | 59.77 |
| 24 | 58.94 | 128.70 | 110.49 |
| 30 | 67.69 | 125.99 | 107.58 |
| 36 | 82.44 | 143.07 | 116.36 |
| 48 | 104.69 | 196.72 | 154.35 |
| 60 | 112.93 | 182.72 | 151.22 |
| 72 | 130.55 | 169.95 | 145.20 |
| 84 | 129.03 | 122.19 | 106.91 |
| 96 | 146.70 | 83.30 | 82.61 |
| 108 | 135.49 | 55.09 | 44.83 |
| 120 | 136.22 | 43.63 | 29.68 |
| 132 | 124.78 | 27.14 | 22.52 |
| 144 | 115.23 | 17.54 | 9.24 |

The results depicted in Table 19 confirm that the method according to the present invention provides effective plasma levels over the 7-day period; whereas if the patch (or patches) containing the same dose is removed after 3 days, the buprenorphine plasma levels fall precipitously over the next 24 hour interval to levels which would be indicative of ineffective treatment for the dosage of buprenorphine. [This result is surprising in view of the fact that the patches are designed to provide effective analgetic levels of buprenorphine only for a three day period—these patches are not designed to provide effective plasma levels of buprenorphine over a substantially longer period of time.] (It must be noted that the absolute mean plasma levels of Example 1 and the Comparative Examples are not directly comparable because these results are taken from different studies involving different subjects, etc.).

[Further surprising results are apparent from the data provided in] Table 20 below[, which] compares the amount of buprenorphine retained in the transdermal delivery systems in Example 1 to certain Comparative Examples, as well as their relative release rates:

TABLE 20

BUPRENORPHINE PATCH RELEASE RATES

| Patch strength | Example | cum. amt. released [mg] | RR [mg/patch/day] 3 days appl. | RR [mg/patch/day] 7 days appl. | $RR_{norm}$ [mg/$cm^2$/day] |
|---|---|---|---|---|---|
| 5 MG | E | 0.44 mg | 0.146 | — | 0.0234 |
| 10 MG | D | 1.23 mg | 0.410 | — | 0.0328 |
| 20 MG | F | 2.52 mg | 0.742 | — | 0.0297 |
| 20 MG | A, C | 3.21 mg | 1.090 | — | 0.0437 |
| 10 MG | 1 | 1.40 mg | — | 0.200 | 0.160 |

RR = relative release rate

The total amount of buprenorphine released for Example 1 (1.40 mg) may be expressed as 0.2 mg buprenorphine administered per day, when averaged over the seven day dosing interval. In contrast, Comparative Example [E] *D* (same patch over 3 days) released a total of 1.23 mg, which may be expressed as 0.41 mg buprenorphine administered per day. [Comparing the cumulative amount released for Example 1 as compared to Comparative Example D, it can be seen that the present invention results in one-half the dose (mg/patch/day) which would be administered based on prior art methodology. Further, it is apparent that almost all of the buprenorphine dose for Example 1 is released over the first 72 hours (3 days)—1.23 mg released from the 10 mg patch over 3 days is 87.86% of the 1.4 mg released from the same patch over 7 days. It is surprising that analgesia can be maintained given the very low amount of buprenorphine released from the 10 mg patch over the 72–168 hour dosing interval.]

Further, the results indicate that over the first 72 hours the buprenorphine is released substantially according to first order kinetics, whereas during the 72–168 hour time period after administration, the buprenorphine is released substantially according to zero order kinetics. This is confirmed from the plasma concentration curve provided for Example 1 in FIG. 1. [Thus, during the first 72 hours after administration according to the invention, a relative release rate of 17.1 ug/br is obtained (1.23 mg divided by 72 hours); whereas from 72–168 hours after administration according to the invention, the relative release rate maybe lowered to only 1.77 ug/hr 1.40 mg minus 1.23 mg=0.17 mg divided by 96 hours) while maintaining effective analgetic levels of buprenorphine in human patients.]

EXAMPLE 2

In Example 2, the method of the present invention is accomplished via a different mode of administration, i.e., intravenous infusion. The pattern of plasma concentrations seen through time in this invention can be achieved by using an intravenous infusion using the injectable, parenteral form of, e.g., buprenorphine hydrochloride suitably diluted in an intravenous infusion solution. The infusion rate would be controlled by a programable infusion pump, to provide the desired plasma concentration profile. The rate of infusion through time can be determined and adjusted based upon pharmacodynamic parameters such as pupil size (pupilometry) or pain relief (analgesia) or by the results of a suitable bioassay to determine the plasma buprenorphine concentrations at any particular point in time. In addition, it is possible to model the desired curve using pharmacokinetic modeling techniques; in this way the desired curve can be approximated without need for pharmacoldnetic or pharmacodynamic monitoring. However, perioidic plasma concentration determinations would made the model more accurate and allow further adjustment of the infusion rate.

Following the method set forth above, mean plasma concentrations are obtained as follows: a mean plasma concentration from about 1 to about 28 pg/ml at about 6 hours after initiation of dosing interval; a mean plasma concentration from about 14 to about 74 pg/ml at about 12 hours after initiation of the dosing interval; a mean plasma concentration from about 30 to about 161 pg/ml at about 24 how after initiation of the dosing integral; a mean plasma concentration from about 51 to about 188 pg/ml at about 36 hours after initiation of the dosing interval; a mean plasma concentration from about 62 to about 246 pg/ml at about 48 hours after initiation of the dosing interval; a mean plasma concentration from about 79 to about 246 pg/ml at about 60 hours after initiation of the dosing interval; a mean plasma concentration from about 85 to about 263 pg/ml at about 72 hours after initiation of the dosing interval; a mean plasma concentration from about 92 to about 263 pg/ml at about 96 hours after initiation of the dosing a mean plasma concentration from about 94 to about 263 pg/ml at about 120 hours after initiation of the dosing interval; a mean plasma concentration from about 86 to about 243 pg/ml at about 144 hours after initiation of the dosing interval; and a mean plasma concentration from about 77 to about 210 pgml at about 168 hours after initiation of the dosing interval (for a seven day dosing interval).

It will be readily apparent that various modifications to the invention may be made by those skilled in the art without departing from the scope of this invention. For example, many different transdermal delivery systems may be utilized in order to obtain the relative release rates and plasma levels described herein. Further, it is possible that mean values for plasma concentrations over a particular patient population for a particular described time point along the dosing interval may vary from the plasma concentration ranges described herein for that time point. Such obvious modifications are considered to be within the scope of the appended claims.

What is claimed is:

1. A method of treating human patients suffering from opioid addiction by applying a transdermal delivery system containing buprenorphine onto the skin of the patient and maintaining the transdermal delivery system in contact with the skin for a 3 day dosing interval, the transdermal delivery system containing an amount of buprenorphine sufficient to maintain an adequate relative release rate to provide a plasma concentration of from about 1000 pg/ml to about 10,000 pg/ml at the end of said 3 day dosing interval, and maintaining the transdermal delivery system in contact with the patient's skin for [at least 2 to about 5] *4* additional days beyond said [3:day] *3 day* dosing interval, such that the patient continues to receive effective treatment for opioid addiction from said transdermal buprenorphine delivery system over said dosing material.

2. The method of claim 1, wherein the plasma concentration attained at the end of said 3 day dosing interval is from about 5000 pg/ml to about 8000 pg/ml.

[3. The method of claim 1 wherein said patch is maintained on the skin to the patient for about 7 days.]

4. The method of claim 1 wherein said transdermal [patch] *delivery system* provides a substantially first order plasma level increase of buprenorphine from the initiation of the dosing interval until about 72 hours after the initiation of the dosing interval*, and substantially zero order plasma level fluctuation of buprenorphine from about 72 hours after the initiation of the dosing interval until the end of the seven-day dosing interval*.

[5. The method of claim 1 wherein said transdermal patch provides substantially zero order plasma level fluctuation of buprenorphine from about 72 hours after the initiation of the dosing interval until the end of at least the five-day dosing interval.]

[6. The method of claim 1 wherein said transdermal patch provides a substantially first order plasma level increase of buprenorphine from the initiation of the dosing interval until about 72 hours after the initiation of the dosing interval and provides a substantially zero order plasma level fluctuation of buprenorphine from about 72 hours after the initiation of the dosing interval until the end of at least the five-day dosing interval.]

[7. The method of claim 5 wherein the plasma level of buprenorphine at 72 hours does not decrease by more than 30% over the next 48 hours.]

8. The method of claim [5] *4* wherein said [patch] *transdermal delivery system* is maintained on the skin of the patient for about 7 days.

[9. The method of claim 8 wherein the plasma level of buprenorphine at 120 hours does not decrease by more than 30% over the next 48 hours.]

10. A method of treating pain in a human patient comprising:

administering an opioid transdermally to said human patient by applying a transdermal delivery system *comprising an opioid* to the skin of a patient, and maintaining said transdermal delivery system in contact with the skin of said patient for [at least 5] *7* days, said transdermal delivery system providing a substantially first order plasma level increase of said opioid from the initiation of the dosing interval until about 72 hours after the initiation of the dosing interval and providing a substantially zero order plasma level fluctuation of said opioid from about 72 hours after the initiation of the dosing interval until the end of [at least] the [five] *seven*-day dosing interval.

11. The method of claim 10 wherein said opioid is buprenorphine.

*12. A method of treating human patients suffering from opioid addiction by applying a transdermal delivery system containing an active ingredient, wherein the active ingredient consists essentially of buprenorphine, onto the skin of the patient and maintaining the transdermal delivery system in contact with the skin for a 3 day dosing interval, the transdermal delivery system containing an amount of buprenorphine sufficient to maintain an adequate relative release rate to provide a plasma concentration of from about 1000 pg/ml to about 10,000 pg/ml at the end of said 3 day dosing interval, and maintaining the transdermal delivery system in contact with the patient's skin for 4 additional days beyond said 3 day dosing interval, such that the patient continues to receive effective treatment for opioid addiction from said transdermal buprenorphine delivery system over said dosing interval.*

*13. The method of claim 12, wherein the plasma concentration attained at the end of said 3 day dosing interval is from about 5000 pg/ml to about 8000 pg/ml.*

*14. The method of claim 12 wherein said transdermal delivery system provides a substantially first order plasma level increase of buprenorphine from the initiation of the dosing interval until about 72 hours after the initiation of the dosing interval, and substantially zero order plasma level fluctuation of buprenorphine from about 72 hours after the initiation of the dosing interval until the end of the seven-day dosing interval.*

*15. The method of claim 14 wherein said transdermal delivery system is maintained on the skin of the patient for about 7 days.*

*16. A method of treating human patients suffering from opioid addiction by applying a transdermal delivery system containing an active ingredient, wherein the active ingredient consists of buprenorphine, onto the skin of the patient and maintaining the transdermal delivery system in contact with the skin for a 3 day dosing interval, the transdermal delivery system containing an amount of buprenorphine sufficient to maintain an adequate relative release rate to provide a plasma concentration of from about 1000 pg/ml to about 10,000 pg/ml at the end of said 3 day dosing interval, and maintaining the transdermal delivery system in contact with the patient's skin for 4 additional days beyond said 3 day dosing interval, such that the patient continues to receive effective treatment for opioid addiction from said transdermal buprenorphine delivery system over said dosing interval.*

*17. The method of claim 16, wherein the plasma concentration attained at the end of said 3 day dosing interval is from about 5000 pg/ml to about 8000 pg/ml.*

*18. The method of claim 16 wherein said transdermal delivery system provides a substantially first order plasma*

*level increase of buprenorphine from the initiation of the dosing interval until about 72 hours after the initiation of the dosing interval, and substantially zero order plasma level fluctuation of buprenorphine from about 72 hours after the initiation of the dosing interval until the end of the seven-day dosing interval.*

*19. The method of claim 18 wherein said transdermal delivery system is maintained on the skin of the patient for about 7 days.*

*20. A method of treating pain in a human patient comprising transdermally administering an active ingredient, wherein the active ingredient consists essentially of an opioid, to said human patient by applying a transdermal delivery system comprising an active ingredient, wherein the active ingredient consists essentially of an opioid to the skin of a patient, and maintaining said transdermal delivery system in contact with the skin of a patient for 7 days, said transdermal delivery system providing a substantially first order plasma level increase of said opioid from the initiation of the dosing interval until about 72 hours after the initiation of the dosing interval and providing a substantially zero order plasma level fluctuation of said opioid from about 72 hours after the initiation of the dosing interval until the end of the seven-day dosing interval.*

*21. The method of claim 20 wherein said opioid is buprenorphine.*

*22. A method of treating pain in a human patient comprising transdermally administering an active ingredient, wherein the active ingredient consists of an opioid, to said human patient by applying a transdermal delivery system comprising an active ingredient, wherein the active ingredient consists of an opioid to the skin of a patient, and maintaining said transdermal delivery system in contact with the skin of said patient for 7 days, said transdermal delivery system providing a substantially first order plasma level increase of said opioid from the initiation of the dosing interval until about 72 hours after the initiation of the dosing interval and providing a substantially zero order plasma level fluctuation of said opioid from about 72 hours after the initiation of the dosing interval until the end of the seven-day dosing interval.*

*23. The method of claim 22 wherein said opioid is buprenorphine.*

* * * * *